(12) United States Patent
Prockop et al.

(10) Patent No.: US 7,374,937 B1
(45) Date of Patent: May 20, 2008

(54) ISOLATION AND EXPANSION OF HUMAN MARROW STROMAL CELLS

(75) Inventors: Darwin J. Prockop, New Orleans, LA (US); David Colter, Philadelphia, PA (US); Carla DiGirolamo, Milford, MA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 09/695,769

(22) Filed: Oct. 25, 2000

Related U.S. Application Data

(60) Provisional application No. 60/162,474, filed on Oct. 29, 1999, provisional application No. 60/189,109, filed on Mar. 14, 2000.

(51) Int. Cl.
*C12N 5/00* (2006.01)
*C12N 5/02* (2006.01)
*C12N 5/08* (2006.01)

(52) U.S. Cl. .................. 435/378; 435/372; 435/384

(58) Field of Classification Search ............... 435/325, 435/355, 372, 373, 384, 336, 395, 405, 378
See application file for complete search history.

(56) References Cited

U.S. PATENT DOCUMENTS

| | | | |
|---|---|---|---|
| 5,766,950 A * | 6/1998 | Greenberger et al. ....... | 435/397 |
| 5,811,094 A | 9/1998 | Caplan et al. | |
| 5,849,287 A | 12/1998 | Greenberger et al. | |
| 5,942,225 A | 8/1999 | Bruder et al. | |

OTHER PUBLICATIONS

Kuznetsov et al. 1997, British Journal of Haematology, 97: 561-570.*
Huang et al., 1997, Biotechnology Letters, 19: 89-92.*
Kuznetsov et al., 1997, J. Bone and Mineral Res., 12: 1335-1347.*
Azizi et al., 1998, PNAS, USA, 95: 3908-3913.*
Prockop, 1997, Science, 276: 71-74.*
Sekiya et al., 2002, Stem Cells, 20: 530-541.*
Ankelsaria, et al., 1987, Proc. Natl. Acad. Sci. USA 84:7681-7685.
Ankelsaria, et al., 1987, Experimental Hematology 15:636-644.
Azizi, et al., 1998, Proc. Natl. Acad. Sci. USA 95:3908-3913.
Beresford, et al., 1992, J. Cell Scoi. 102:341-351.
Bhatia, et al., 1998, Bone Marrow Transplantation 22:87-90.
Bienzle, et al., 1994, Proc. Natl. Acad. Sci. USA, 91:350-354.
Bjornson, et al., 1999, Science 283:534-537.
Byers, et al., 1999, J. Pathol. 187:374-381.
Caplan, 1991, J. Ortho. Res. 9:641-650.
Carpenter, et al., 1999, Exp. Neurol. 158:265-278.
Carter, et al., 1992, Blood 79:356-364.
Castro-Malaspina, et al., 1980, Blood 56:289-301.
Cheng, et al., 1994, Endocrinology 134:277-286.
Chiang, et al., 1999, Human Gene Therapy 10:61-76.
Clark and Keating, 1995, Ann. New York Acad. Sci. 770:70-78.
Eglitis, et al., 1997, Proc. Natl. Sci. USA 94:4080-4085.
Friedenstein, et al., 1976, Experimental Hematology 4:267-274.
Friedenstein, et al., 1987, Cell and Tissue Kinetics 20:263-272.
Glimm, et al., 1999, Blood 97:2161-2168.
Goodell, et al., 1997, Nat. Med. 12:1337-1345.
Gronthos, et al., 1996, J. Hematotheerapy 5:15-23.
Gussoni, et al., 1999, Nature 401:390-393.
Horwitz, et al., 1999, "Transplantibility and therapeutic effects of bone marrow-derived mesenchymal cells in children with severe osteogenesis imperfecta," Abstracts of the 7th Intl. Meeting on Osteogenesis Imperfecta, Montreal.
Horwitz, et al., 1999, Natl. Med. 5:309-313.
Hou, et al., 1999, Proc. Natl. Acad. Sci. USA 96:7294-7299.
Howlett, et al., 1986, Clin. Orethoped. and Related Res. 213:251-263.
Hurtwitz, et al., 1997, Human Gene Therapy 8:137-156.
Jaiswal, et al., 1997, J. Cell. Bio. 64:295-312.
Joyner, et al., 1997, Bone 21:1-6.
Keating, et al., 1996, Exper. Hematol. 24:1056, Abs. 180.
Kelly, et al., 1998, Endocrinology 139:2622-2628.
Kiefer, 1991, Blood 78:2577-2582.
Kopen, et al., 1999, Proc. Natl. Acad. Sci. USA 96:10711-10716.
Kuznetsov, et al., 1997, Br. J. Haematol. 97:561-570.
Lecka-Czernik, et al., 1999, J. Cell Biochem. 74:357-371.
Long, et al., 1995, J. Clin. Invest. 95:881-887.
Matthews, et al., 1995, Meth. Mol. Biol. 48:273-280.
Mets and Verdonk, 1981, Mech. Aging. Dev. 16:81-89.
Nilsson, et al., 1997, Blood 89:4013-4020.
Nilsson, et al., 1999, J. Exp. Med. 189:729-734.
Owen and Friedenstein, 1988, In: Cell and Molecular Biology of Vertebrate Hard Tissues, pp. 42-60, Ciba Foundation Symposium, Chichester, UK.
Pereira, et al., 1995, Proc. Natl. Acad. Sci. USA 92:4857-4861.
Pereira, et al., 1998. Proc. Natl. Acad. Sci. USA 95:1142-1147.
Piersma, et al., 1985, Experimental Hematology 13:237-243.
Pittenger, et al., 1999, Science 284:143-147.
Rickard, et al., 1994, Dev. Biol. 161:218-228.
Rickard, et al., 1996, J. Bone Miner. Res. 11:312-324.
Satomura, et al., 1998, J. Cell Physiol. 177:426-438.
Simmons and Torok-Storb, 1991, Blood 78:2848-2853.
Simmons, et al., 1991, Blood 78:55-62.
Stanford, et al., 1995, J. Biol. Chem. 270:9420-9428.
Stewart, et al., 1999, J. Bone Miner. Res. 14:1345-1356.
Uzawa, et al., 1999, J. Bone Miner. Res. 14:1272-1280.
Verma, et al. 1997, Nature 389:239-242.

(Continued)

*Primary Examiner*—Anne Marie Wehbe'
*Assistant Examiner*—Joanne Hama
(74) *Attorney, Agent, or Firm*—Seed IP Law Group PLLC

(57) ABSTRACT

The invention includes in vitro methods of inducing and enhancing proliferation of human marrow stromal cells for use in, for example, gene therapy and transplantation methods. The invention also includes a method of assessing the expandability (i.e., proliferative capacity) of human marrow stromal cells. In addition, the invention includes a conditioned medium for enhancing proliferation of human marrow stromal cells.

29 Claims, 34 Drawing Sheets

OTHER PUBLICATIONS

Wakitani, et al., 1994, Muscle and Nerve 18:1417-1426.

Waller, et al., 1995, Blood 85:2422-2435.

Whyte, et al., 1999, "Marrow cell transplatation for infantile hypophosphatasia." Abstracts of the 7th Intl. Meeting on Osteogenesis Imperfecta, Montreal.

Phinney, et al., 1999, Journal of Cellular Biochemistry, 72:570-585.

Abboud, et al., 1991, vol. 88, August, 470-475.

Kuznetsov, et al., 1997, Journal of Bone and Mineral Research, 12:1335-1347.

Bruder, et al., 1997, Journal of Cellular Biochemistry 64, 278-294.

DiGirolamo, et al. 1999, British Journal of Haematology, vol. 107, No. 2, 275-281.

Colter et al., 2000, PNAS 97:3213-3218.

Javazon et al., 2001, Stem Cells. 19:219-225.

Huss, et al., 1995, Blood, 85:2414-2421.

Huang, et al., 1997, Biotechnology Letters, 19:89-92.

* cited by examiner

| DONOR 59R | TOTAL CELLS | CFU % | FOLD INCREASE | DOUBLINGS |
|---|---|---|---|---|
| ↓ | | | | |
| 20 ml aspirate | | | | |
| ↓ | | | | |
| MNCs Plated on 176 cm² | 2.69 x 10⁷ (MNCs) | | | |
| ↓ | | | | |
| Trypsin Harvest (d11) | 8.11 x 10⁵ | 39 % | | |
| ↓ | | | | |
| Plated on 176 cm² | 528 (3 cells/cm²) | | | |
| ↓ E1 | | | | |
| Trypsin Harvest (d10) | 1.85 x 10⁵ | 42 % ⟶ | 350 | 9 db |
| ↓ | | | | |
| Plated on 176 cm² | 528 | | | |
| ↓ E2 | | | | |
| Trypsin Harvest (d10) | 2.40 x 10⁵ | 29 % ⟶ | 455 | 9 db |
| ↓ | | | | |
| Plated on 176 cm² | 528 | | | |
| ↓ E3 | | | | |
| Trypsin Harvest | 7.5 x 10⁵ | ⟶ | 1420 | 11 db |

FIGURE 8

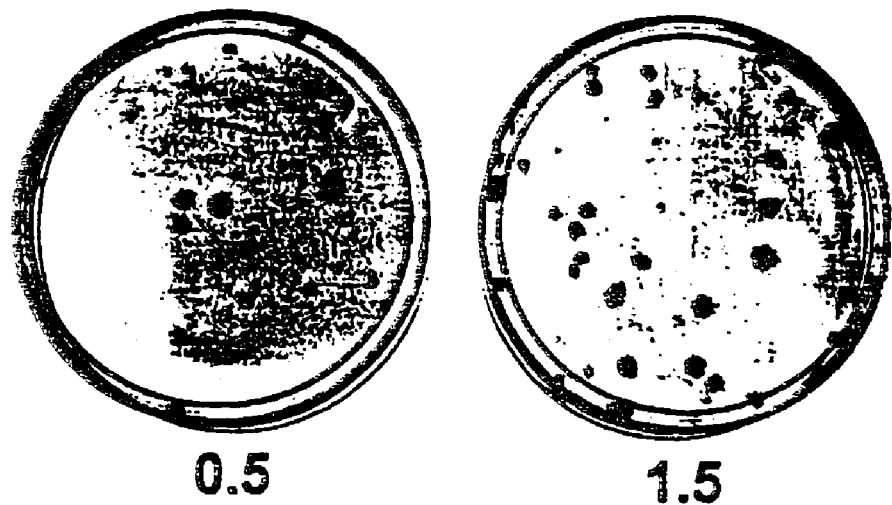
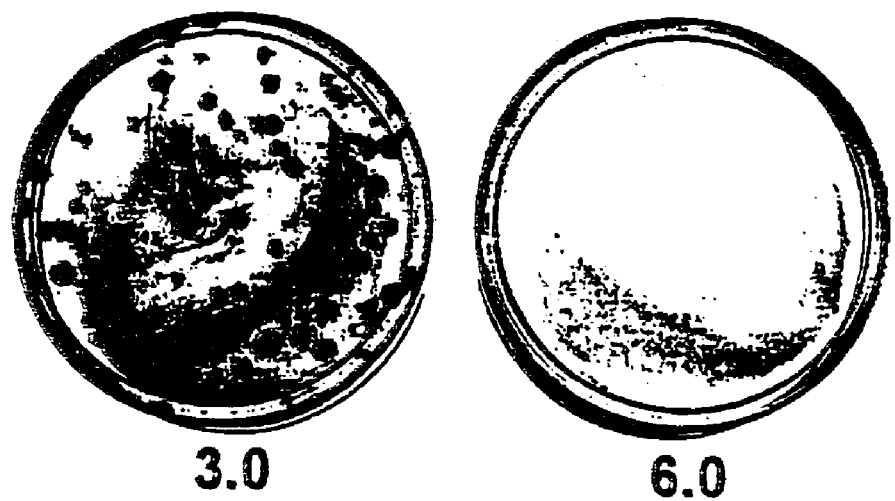
Fig. 17

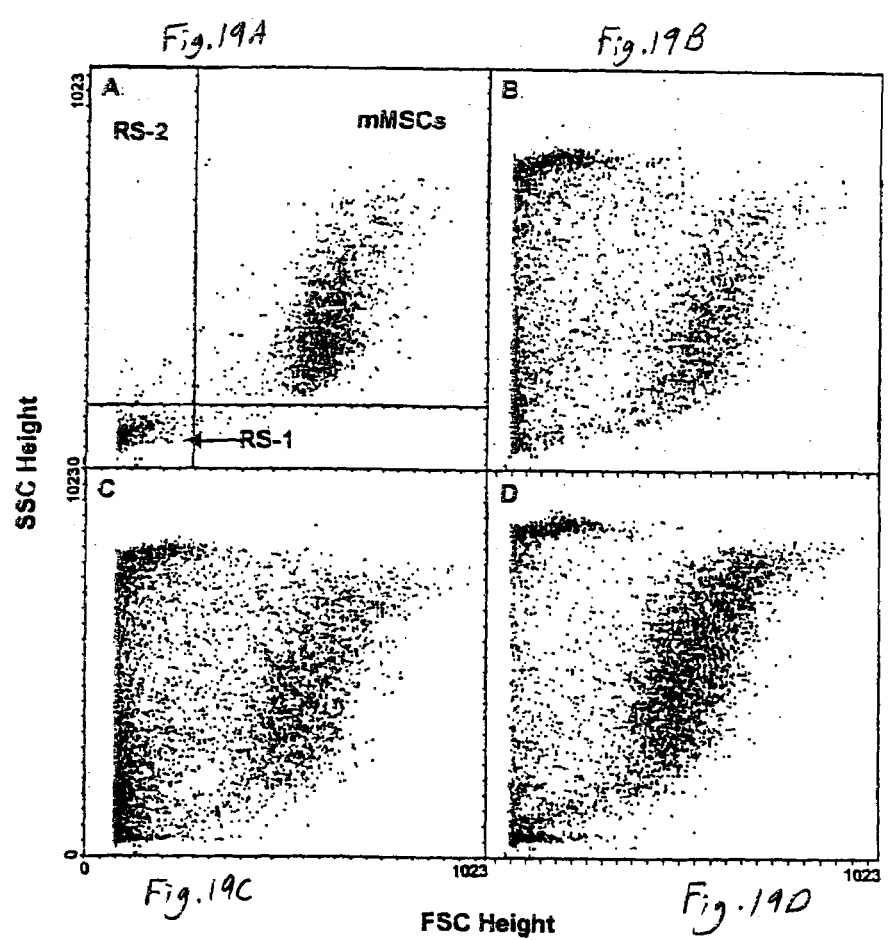

EPITOPE PROFILE OF THE CELLS

| EPITOPE | RS-1 CELLS | RS-2 CELLS | MATURE CELLS |
|---|---|---|---|
| CD34 | Negative | Negative | Negative |
| CD11b (Mac-1) | Negative | Negative | Negative |
| CD43 | Negative | Negative | Negative |
| CD45 | Negative | Negative | Negative |
| CD31 | Dim | Dim | Dim |
| CD38 | Dim | Dim | Dim |
| CD117 (c-kit) | Dim | Dim | Dim |
| STRO-1 | Negative | Negative | Dim |
| CD90 (Thy-1) | Dim | Negative | Positive |
| EMA | Dim | Negative | Negative |
| CD59 | Positive | Negative | Positive |
| HLA-1 | Negative | Negative | Negative |
| CD14 | Negative | Negative | Negative |
| CCR5 | Negative | Negative | Negative |
| PDGF-R | Negative | Negative | Dim |
| CD44 | Positive | Negative | Positive |
| CD50 | Negative | Negative | Negative |
| EGF-R | Negative | Negative | Dim |
| CD104 | Dim | Dim | Negative |
| HLA-1 | Dim | Dim | Positive |
| CD27 | Negative | Negative | Negative |
| CD53 | Negative | Negative | Negative |
| CD10 | Negative | Negative | Positive |
| CD147 | Negative | Negative | Positive |
| CD114 | Negative | Negative | Negative |
| CD81 | Dim | Negative | Positive |
| CD49e | Positive | Positive | Positive |
| Human L1 | Negative | Negative | Negative |
| CD4 | Dim | Dim | Negative |
| CD1a | Negative | Negative | Negative |
| CD109 | Negative | Negative | Negative |
| MDR | Dim | Dim | Negative |
| BFGFR | Dim | Dim | Dim |
| FLK | Dim | Dim | Negative |

Mature MSCs

FIG. 22A-B

| Identification # | Code # | Source (NCBI#, MW, pI) |
|---|---|---|
| LB2D6-80-1 Day 5 | | |
| Spot 9 | BS1-1-1 | Myosin Regulatory Light Chain 2 (5453740, 19.8, 4.67) |
| Spot 10 | BS1-1-2 | Smooth Muscle Protein 22a (3123283, 22.6, 8.87) |
| Spot 14 | BS1-1-3 | Little data |
| Spot 15 | BS1-1-4 | Thioredoxin Peroxidase 2 (4505591, 22.1, 8.27) |
| Spot 22 | BS1-1-5 | Lipocortin II (4757756, 38.6, 7.6) |
| Spot 24 | BS1-1-6 | Citrate Synthase (4758076, 51.7, 8.13) |
| Spot 17 | BS1-1-7 | Glutathione Transferase Omega (4758484, 27.6, 6.24) |
| Spot 3 | BS1-1-8 | Little data |
| Spot 25 | BS1-1-9 | Little data |
| Spot 11 | BS1-1-10 | Ribosomal Protein S12 (4506683, 14.5, 6.31) |
| LB2D6-80-2 Day 12 | | |
| Spot 5 | BS1-1-11 | Lipocortin V (4502107, 35.9, 4.9) |
| Spot 8 | BS1-1-12 | Data |
| Spot 6 | BS1-1-13 | Data |
| Spot 1 | BS1-1-14 | Little data |
| Spot 17 | BS1-1-15 | Data |
| Spot 14 | BS1-1-16 | Little data |
| Spot 12 | BS1-1-17 | Data |
| Spot 4 | BS1-1-18 | Little data |
| Spot 15 | BS1-1-19 | Little data |
| Spot 11 | BS1-1-20 | Little data |

The above table has previous identifications, and the six new ones. The peptides identified in each protein are shown on pages 5-10 in Sequest format, bold or underlined. Any amino acid differences from the database entry are noted above the sequence.

FIG. 29

ISOLATION AND EXPANSION OF HUMAN MARROW STROMAL CELLS

CROSS-REFERENCE TO RELATED APPLICATIONS

This application claims priority under 35 U.S.C. § 119(e) to U.S. Provisional Application No. 60/162,474, filed on Oct. 29, 1999, and U.S. Provisional Application No. 60/189,109, filed on Mar. 14, 2000.

STATEMENT REGARDING FEDERALLY SPONSORED RESEARCH OR DEVELOPMENT

This invention was supported in part using funds from the U.S. Government (NIH Grant No. RO1-AR44210), and the U.S. Government may therefore have certain rights in the invention.

BACKGROUND OF THE INVENTION

Most cells in adult animals are terminally differentiated, meaning that they cannot normally become cells of a different type. However, certain cells ("multipotential" cells) retain the ability to differentiate (i.e., become cells of one of several types), even in adult tissues.

Bone marrow contains various types of multipotential cells, including precursors of non-hematopoietic cells (e.g., MSCs) and stem cells which can differentiate to become various hematopoietic cells (Friedenstein et al., 1976, Experimental Hematology 4:267-274; Castro-Malaspina et al., 1980, Blood 56:289-301; Mets and Verdonk, 1981, Mech. Aging. Dev. 16:81-89; Piersma et al., 1985, Experimental Hematology 13:237-243; Friedenstein et al., 1987, Cell and Tissue Kinetics 20:263-272; Caplan, 1991, J. Ortho. Res. 9:641-650; Prockop, 1997, Science 276:71-74). Bone marrow cells that are precursors of non-hematopoietic cells and tissues have been designated "plastic-adherent cells" or "colony-forming unit fibroblasts", because they readily adhere to culture dishes and form fibroblast-like colonies (Piersma et al., 1985, Exp. Hematol. 13:237-243; Owen and Friedenstein, 1988, In: Cell and Molecular Biology of Vertebrate Hard Tissues, pp. 42-60, Ciba Foundation Symposium, Chichester, UK). MSCs are designated mesenchymal stem cells or mesenchymal progenitor cells by still others (Caplan, 1991, J. Ortho. Res. 9:641-650), owing to their ability to differentiate into a variety of non-hematopoietic cells. In addition, these cells have been designated MSCs, because they appear to arise from supporting structures found in marrow and because they can act as feeder layers for the growth of hematopoietic stem cells in culture (Prockop, 1997, Science 276:71-74; Anklesaria, 1987, Proc. Natl. Acad. Sci. USA 84:7681-7685). MSCs have also been used as a feeder layer to obtain cultures of an enriched population of hematopoietic stem cells (Kiefer, 1991, Blood 78:2577-2582).

MSCs have recently attracted renewed interest, because they appear to provide circulating progenitor cells which can repopulate non-hematopoietic tissues (Pereira et al., 1998, Proc. Natl. Acad. Sci. USA 95:1142-1147; Ferrari et al., 1998, Science 279:1456, 1528-1530), and because they can potentially serve as effective vehicles for cell and gene therapy (Caplan, 1991, J. Ortho. Res. 9:641-650; Prockop, 1997, Science 276:71-74).

The original reports of MSCs by Friedenstein et al. (1976, Exp. Hematol. 4:267-274) have been extensively replicated and extended by other investigators (Castro-Malaspina et al., 1980, Blood 56:289-301; Mets and Verdonk, 1981, Mech. Aging Dev. 16:81-89; Piersma et al., 1985, Exp. Hematol. 13:237-243; Howlett et al., 1986, Clin. Ortho. and Related Res. 213:251-263; Anklesaria et al., 1987, Exp. Hematol. 15:636-644; Owen and Friedenstein, 1988, In: Cell and Molecular Biology of Vertebrate Hard Tissues, pp. 42-60, Ciba Foundation Symposium, Chichester, UK; Beresford et al., 1992, J. Cell Sci. 102:341-351; Cheng et al., 1994, Endocrinology 134:277-286; Rickard et al., 1994, Dev. Biol. 161:218-228; Clark and Keating, 1995, Ann. New York Acad. Sci. 770:70-78). The results of those investigations establish that MSCs which are isolated by adherence to tissue culture glass and plastic surfaces are multipotential, in that they can differentiate into osteoblasts, chondrocytes, and adipocytes. Subsequently, MSCs isolated in this manner were demonstrated to differentiate into myoblasts and myotubes (Wakitani et al., 1994, Muscle and Nerve 18: 1417-1426; Prockop, 1997, Science 276:71-74).

Friedenstein et al. (1987, Cell and Tissue Kinetics 20:264-272) demonstrated that MSCs obtained from rabbits can be amplified to achieve 20 to 30 doublings in culture, and that such cells could synthesize bone following implantation in a diffusion chamber in vivo. More recently, Kuznetsov et al. (1997, J. Bone Miner. Res. 12:1335-1347) demonstrated that about 60% of single colony-derived MSCs obtained from human donors form bone when implanted into immunodeficient mice using implantation vehicles containing a hydroxyapatite and tricalcium phosphate ceramic matrix. Bruder et al. (1997, J. Cell. Biochem. 64:278-294) reported that human MSCs derived from bone marrow aspirates could be induced to undergo 38±4 doublings in culture, and that MSCs were able to differentiate into osteoblasts in vitro following such doublings.

Stromal cells are believed to strongly influence the microenvironment within bone marrow in vivo. When isolated, MSCs are initially quiescent, but eventually begin dividing. Thus, MSCs can be cultured in vitro. MSCs have been used to generate colonies of fibroblastic adipocytic and osteogenic cells, when maintained in culture under appropriate conditions. MSCs can also be made to differentiate into cartilage cells and myoblasts. If plastic- or glass-adherent MSCs are cultured in the presence of hydrocortisone or other selective conditions, cell populations enriched for hematopoietic precursor cells or osteogenic cells can be obtained (Carter et al., 1992, Blood 79:356-364 and Bienzle et al., 1994, Proc. Natl. Acad. Sci. USA, 91:350-354).

The potential of MSCs to differentiate into cells of various lineages in cell culture has been described (e.g. Rickard et al., 1996, J. Bone Miner. Res. 11:312-324; Stanford et al., 1995, J. Biol. Chem. 270:9420-9428; Kuznetsov et al., 1997, J. Bone Miner. Res. 12:1335-1347; Kelly et al., 1998, Endocrinology 139:2622-2628; Lecka-Czernik et al., 1999, J. Cell Biochem. 74:357-371; Uzawa et al., 1999, J. Bone Miner. Res. 14:1272-1280). Others have also described the potential of MSCs and related cells obtained from bone marrow to differentiate into multi-cellular lineages in vivo. Infusion of MSCs into lethally irradiated mice resulted in appearance in the mice of progeny of the MSCs in a variety of tissues, including bone, cartilage, and lung tissues (Pereira et al., 1998, Proc. Natl. Acad. Sci. USA 95:1142-1147). The progeny MSCs expressed a marker type I procollagen gene in bone (a tissue which normally contains type I collagen), but did not express the same gene in collagen (a tissue which does not normally contain type I collagen). Infusion of male MSCs into irradiated female mice led to the presence of Y chromosome-containing cells in primary cultures of fibroblasts derived from a number of different tissues. Nilsson et al. (1999, J. Exp. Med. 189:729-734) demonstrated the presence of donor marked cells as osteoblasts and osteocytes in mice into which large numbers of MSCs were infused, but which did not undergo marrow ablation. Hou et al. (1999, Proc. Natl. Acad. Sci. USA 96:7294-7299) detected donor MSCs as osteoblasts and osteocytes in the bone of lethally irradiated mice. In those MSCs, expression of a marker CAT gene was driven by an osteocalcin promoter.

Engraftment of MSCs or related bone marrow-derived cells into muscle has been reported. Ferrari et al. (1998, Science 279:1456, 1528-1530) reported engraftment of donor MSCs into muscle following either local injection or systemic injection. Gussoni et al., (1999, Nature 401:390-393) examined incorporation into muscle of a rare marrow cell defined as "side population" (SP) cells. SP cells were originally identified in marrow by Goodell et al. (1997, Nat. Med. 12:1337-1345) as rare cells that are small in size and rapidly secrete a series of labeling dyes, because they contain a large amount of a multi-drug-resistant protein. SP cells are CD34-negative, but are precursors of CD34-positive hematopoietic stem cells and other hematopoietic cells. Gussoni et al. infused small numbers of SP cells into lethally irradiated mdx mice that have a mutation in the dystrophin gene. These investigators observed that about 4% of the muscle fibers in the mdx mice contained dystrophin derived from the donor cells. In addition, muscle SP cells could be isolated from skeletal muscle of the mdx mice, and these cells could be used to re-populate marrow and to rescue the mice from marrow ablation.

These and other reports demonstrate that systemic administration of MSCs to marrow-ablated mice leads to appearance of progeny of the MSCs in marrow, lung, liver, bone, cartilage, and muscle tissues. These results indicate that MSCs can differentiate into cells of different lineages, and thus can be used to supplement tissues of various types by systemic or local administration of MSCs. Thus, MSCs (i.e. MSCs obtained from a donor or expanded from a patient's own complement of MSCs) can be used to treat diseases of at least marrow, lung, liver, bone, cartilage, and muscle tissues by replacing or supplementing diseased tissue. Furthermore, recombinantly-constructed MSCs (i.e. harboring an exogenous gene or a normal gene) can be used to deliver a gene product to any of these tissues (e.g. to deliver dystrophin to muscle tissue).

The potential of MSCs and related marrow-derived cells to engraft into the central nervous system has been described. Eglitis et al., (1997, Proc. Natl. Acad. Sci. USA 94:4080-4085) described the presence of donor-derived astrocytes following infusion of whole marrow into recipient immuno-deficient mice. Significant shortcomings of prior attempts to use bone marrow-derived cells to treat central nervous system disorders include that cells infused into nervous system tissues have not behaved appropriately following infusion, and that it has been difficult to obtain cells for infusion.

Azizi et al. (1998, Proc. Natl. Acad. Sci. USA 95:3908-3913) reported that either rat or human MSCs infused into the basal ganglia of adult rats integrated and migrated in a manner similar to paraventricular astrocytes that have many of the properties of neural stem cells. Kopen et al. (1999, Proc. Natl. Acad. Sci. USA 96:10711-10716) demonstrated that murine MSCs infused into the paraventricular region of newborn mice integrated and migrated in a manner similar to neural stem cells. The cells appeared to increase in number as the mouse brains enlarged. Some of the cells differentiated into astrocytes. Other cells appeared in large numbers in neuron-rich regions and may have differentiated into neurons. Use of MSCs for treatment of disorders of the central nervous system has also been described in PCT application publication number WO99/43286. The potential for inter-convertibility of cells between bone marrow and central nervous system tissues was also emphasized by a recent report in which it was demonstrated that neural stem cells can reconstitute the hematopoietic system in mice that have undergone marrow ablation (Bjornson et al., 1999, Science 283:534-537).

Clinical trials involving administration of MSCs and related cells have been carried out. For example, a trial has been initiated in which children afflicted with severe osteogenesis imperfecta (type III) underwent marrow ablation, followed by transfusion of allogeneic marrow from an HLA-compatible brother or sister (Horwitz et al., 1999, Nat. Med. 5:309-313; Horwitz et al., 1999, "Transplantability and therapeutic effects of bone marrow-derived mesenchymal cells in children with severe osteogenesis imperfecta," Abstracts of the 7th Intl. Meeting on Osteogenesis Imperfecta, Montreal). In this trial, it was hypothesized that whole bone marrow may contain significant numbers of MSCs and related osteoblast precursors that can replace the recipient's osteoblasts and thereby convert a severe form of osteogenesis imperfecta into a milder form of the disease. Five children in the trial exhibited significant improvement, as assessed, for example, by decreased fracture rate and increased total body mineral content. However, donor cells accounted for only 1.3 to 2% of the osteoblasts in three of four patients from whom bone marrow biopsies were obtained. Thus, these results can be interpreted in various ways. For example, it may be that the whole bone marrow transfusions contained only a small number of late progenitors of osteoblasts, and that these cells provide only a temporary improvement in the status of bone in these patients. Other possibilities are that marrow ablation alone produced an undefined benefit, even though bone marrow transplants have, in general, led to osteopenia in children (e.g. Bhatia et al., 1998 Bone Marrow Transplantation 22:87-90).

In another clinical trial, White et al., (1999, "Marrow cell transplantation for infantile hypophosphatasia," Abstracts of the 7th Intl. Meeting on Osteogenesis Imperfecta, 1999) treated an eight-month-old child afflicted with infantile hypophosphatasia, a genetic deficiency of the alkaline phosphatase that occurs in osteoblasts. The child underwent bone marrow ablation, and then received a bone marrow transplant from an HLA-compatible sister. One hundred days following the transplant, the child demonstrated a remarkable reversal of her worsening skeletal disease and other improvements. However, the beneficial effects were no longer present six months later. The child was then given a non-T-cell depleted boost with MSCs which were expanded from her sister and which were administered without further marrow ablation. Radiographs nine months following the booster dose showed significant improvement that appeared to persist.

Despite the great interest in examining the biology of MSCs and their potential use for therapy, there is still no generally accepted protocol for isolating and expanding MSCs in culture. Most experiments relating to differentiation of MSCs have been performed using cultures of MSCs that have been isolated primarily by virtue of the MSCs tight adherence to tissue culture dishes, as described (Friedenstein et al., 1976, Exp. Hematol. 4:267-274; Friedenstein et al., 1987, Cell Tissue Kinet. 20:263-272). Others have attempted to prepare more homogenous MSC populations (e.g. Long et al., 1995, J. Clin. Invest. 95:881-887; Simmons et al., 1991, Blood 78, 55-62; Waller et al., 1995, Blood 85:2422-2435; Rickard et al., 1996, J. Bone Miner. Res. 11:312-324; Joyner et al., 1997, Bone 21:1-6). However, none of these protocols has gained wide acceptance. In addition, these protocols have been primarily designed to isolate osteoblast precursors. Use of these protocols has not been investigated to determine if they yield cells that are truly multipotential.

Recently, there has been renewed interest in using the Stro-1 antibody to isolate MSCs (e.g. Gronthos et al., 1996, J. Hematotherapy 5:15-23; Byers et al., 1999, J. Pathol. 187:374-381; Steart et al., 1999, J. Bone Miner. Res. 14:1345-1356). However, it may be that Stro-1 primarily stains large and granular cells in cultures of MSCs. Therefore, this antibody may be primarily useful for identifying or isolating only cells that are committed to the osteoblast lineage.

This review of the literature demonstrates that transplantation of MSCs have significant therapeutic and gene transfer uses. However, prior art methods for isolating MSCs and inducing their proliferation have practical limitations, including the extent of population expansion that can be achieved using prior art methods. There remains a critical need for methods of reliably inducing significant proliferation of MSCs in culture without inducing differentiation of the MSCs as they proliferate. The present invention satisfies this need.

BRIEF SUMMARY OF THE INVENTION

The invention relates to a method of inducing proliferation of isolated human marrow stromal cells in vitro. The method comprises providing the isolated cells and a growth medium to a growth surface such that the initial density of the isolated cells is less than about 50, 25, 12, 10 or 6, cells per square centimeter of growth surface and incubating the surface under growth-promoting conditions. The initial cell density should be at least about 0.5 or 3 cells per square centimeter of growth surface. For example, the initial density can be about 3 or about 1.5 cells per square centimeter of growth surface. The cells can be harvested from the growth surface following not more than, for example, about 10 or 14 days of incubation.

After the cells are harvested, those cells and a growth medium and be provided to a second growth surface such that the initial density of the harvested cells is less than about 50 cells per square centimeter of second growth surface. The second growth surface is incubated under growth-promoting conditions so that the cells proliferate. Those cells can be harvested from the second growth surface following not more than about 14 days of incubation, and can thereafter be provided, together with a growth medium, to a third growth surface such that the initial density of the cells harvested from the second growth surface is less than about 50 cells per square centimeter of third growth surface. The third growth surface can be incubated under growth-promoting conditions, so that the cells proliferate. Of course, further rounds of harvest and expansion can be performed.

The growth medium with which the cells are harvested can comprises a mammalian serum, such as fetal bovine serum, or a growth factor (e.g. fibroblast growth factor, platelet derived growth factor, insulin growth factor, or endothelial growth factor) can be added to the growth medium.

The invention also relates to a method of enhancing in vitro proliferation of isolated human marrow stromal cells growing on a surface in the presence of a growth medium. The method comprises supplementing the growth medium with a factor present in a conditioned medium. The conditioned medium is obtained from a culture of producer human marrow stromal cells which are grown on a second surface at an initial density of at least about 0.5 or 12 cells per square centimeter and which are incubated for at least about 3 or 6 days. The growth medium can be supplemented with the factor by supplementing the growth medium with the conditioned medium or by size-fractionating the conditioned medium and then supplementing the growth medium with a fraction of the conditioned medium containing size-fractionated molecules having a molecular weight of about 30,000 or 10,000.

The invention further relates to a conditioned medium for inducing proliferation of human marrow stromal cells. The conditioned medium is made by incubating human marrow stromal cells for at least about 3 days on a surface in the presence of a growth medium at an initial density of less than about 12 cells per square centimeter of surface. The growth medium is thereby transformed into conditioned medium.

In another aspect, the invention relates to a method of inducing proliferation of human marrow stromal cells. This method comprises isolating mononuclear cells from a bone marrow sample, incubating the mononuclear cells to yield colonies, isolating an individual colony, and incubating human marrow stromal cells obtained from the isolated colony in a container having a growth surface. The container contains a growth medium and the cells at an initial density of less than about 50 cells per square centimeter of growth surface. This induces the cells to proliferate.

The invention also relates to a method of assessing the expandability of human marrow stromal cells in vitro. The method comprises incubating the cells (e.g. for at least about 10 days) on a surface in the presence of a growth medium at an initial density of less than about 50 cells per square centimeter of surface and assessing the colony-forming efficiency of the cells. The expandability of the cells is approximately proportional to the colony-forming efficiency of the cells. The colony-forming efficiency can be compared with the colony-forming efficiency of another sample of human marrow stromal cells which have known expandability and which are incubated in the same manner. Alternatively, the colony-forming efficiency can be compared with a reference plot of colony-forming efficiency versus expandability, such as the plot of FIG. 2.

The invention also includes a method of purifying marrow stromal cells. The method comprises contacting a population of stromal cells with an antibody to Lipocortin II, and isolating from the population of stromal cell cells which bind the antibody, thereby purifying the marrow stromal cells.

Also included is an additional method of purifying marrow stromal cells wherein the method comprises providing isolated marrow stromal cells and a growth medium to a growth surface such that the initial density of the isolated cells is less than about 50 cells per square centimeter of growth surface, incubating the surface under growth-promoting conditions, whereby the cells proliferate, contacting the population of stromal cells with an antibody to Lipocortin II, and isolating from the population of stromal cell cells which bind the antibody, thereby purifying the marrow stromal cells.

BRIEF DESCRIPTION OF THE DRAWINGS

FIG. 8 is a diagram depicting cell expansion achieved by low-density subculture, as disclosed herein.

FIG. 12, comprising In FIG. 12F, the percentage of colonies in each of FIGS. 12A, 12B, and 12C which had a diameter greater than 5 millimeters is indicated.

FIG. 13, comprising

FIG. 17 is an image which depicts the size of colonies observed after plating of MSCs at a density of 0.5, 1.5, 3.0 or 6.0 cells per square centimeter. After incubation for 14 days in 79 square centimeter plates, the colonies were visualized by staining with 0.5% Crystal Violet in methanol for 5 to 10 minutes at room temperature.

FIG. 18, comprising

FIG. 19, comprising FIGS. 19A-19D, is a quartet of graphs which depict individual FACS analyses of cells for size and granularity after selected periods of incubation. Preliminary experiments indicated that the precursor-product relationships among the cell populations were more apparent in cultures that grew slowly. Therefore, the stock sample of MSCs selected for the experiment was previously shown to expand slowly in culture and have an unusually low CFU value of about 12% (see reference 41). The cells were plated at a sub-optimal density of 3 cells per square centimeter that was equivalent to 1.0 cell per square centimeter or less for samples that expanded more rapidly and had higher CFU values (see FIG. 17). FIG. 19A is a FACS analysis of cells in stationary culture at day 14. Lines indicate gating used to define RS-1 cells, RS-2 cells, and mMSCs. FIG. 19B is a FACS analysis on day 5 after initial plating. FIG. 19C is a FACS analysis on day 7 after initial plating. FIG. 19D is a FACS analysis on day 10 after initial plating. In FIG. 19, "FSC" means forward scattering of light (an assay for cell size), and "SSC" means side scattering of light (an assay for cell granularity). Values are indicated in arbitrary units.

FIG. 26 is a table depicting additional epitopes on RS-1 and RS-2 cells and mature MSCs (mMSCs). The antibodies which reacted with the cells are listed as are those that did not react.

FIGS. 28A and B is a series of images of two dimensional gels of proteins obtained from cultures that are enriched for RS cells and cultures that have considerably fewer of the RS cells and more of the mature MSCs. In FIG. 28A there are shown proteins obtained from early lag phase cultures (5 days of incubation; 60% RS-1 and RS-2 cells) and in FIG. 28B there is shown proteins obtained from late lag phase cultures (12 days of incubation; 15% RS-1 cells).

FIG. 29 is a table depicting a protein analysis of the gels shown in FIG. 28A (early lag phase culture, identification number LB2D6-80-1), and FIG. 28B (late lag phase culture, identification number LB2D6-80-7) in which proteins unique to either culture were analyzed.

DETAILED DESCRIPTION OF THE INVENTION

Figure 1:
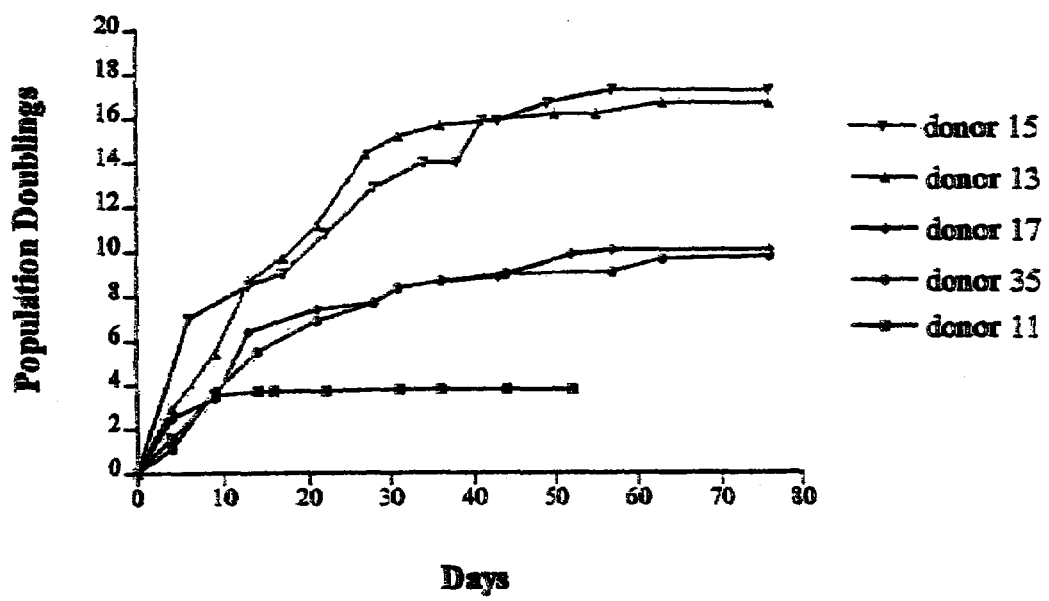
FIG. 1 is a graph depicting expandability (indicated by population doublings) of human marrow stromal cells (MSCs) in vitro using prior art (i.e. high density) culture methods. The values indicate population doublings after MSCs obtained from five different donors were twice cultured to confluence, first on a 25 square centimeter surface, and then on a 75 square centimeter surface. The MSCs were then passed by plating at high density (i.e. about 5,000 cells per square centimeter) and grown to confluence for about 14 days.

The present invention relates to methods of inducing or enhancing proliferation of human marrow stromal cells (MSCs) while preserving their multipotentiality, and also relates to assessing the expandability of MSCs obtained from a human. The terms "marrow stromal cell," "MSC," and "stromal cell" are used interchangeably herein.

The invention relates to the discovery that the expandability of human marrow stromal cells (MSCs; i.e., the capacity of MSCs to replicate themselves multiple times) can be increased by incubating the MSCs in the presence of a growth surface and a growth medium at an initial cell density that is much lower than the initial cell density used in prior art MSC culture/expansion methods. In prior art methods, MSCs are typically cultured at initial cell densities greater than about 1,000 cells per square centimeter. By contrast, according to the method of the invention, MSCs are cultured at an initial cell density of less than about 50, 25, 12, 10, 6, or 3 cells per square centimeter. Preferably initial cell densities include about 1.5 to 12 cells per square centimeter (e.g., 3 cells per square centimeter). The initial cell density should be at least about 0.5 cells per square centimeter).

In the MSC culture/expansion method of the invention, MSCs retain their multipotentiality (i.e., their capacity to differentiate into one of various cell types, such as osteoblasts, adipocytes, and the like). MSCs expanded using the method of the invention retain their ability to differentiate to a greater extent (i.e., in greater proportion) than do MSCs expanded or cultured using prior art methods.

Stem cells (of which MSCs are one type) have a tremendous potential for use in methods for cell therapy and for gene therapy for a large number of human diseases because of a unique property: A stem cell can divide into two cells such that one daughter cell remains a stem cell and the other daughter cell changes its characteristics so that it becomes or gives rise to one or more specialized (i.e., differentiated) cells that perform certain functions in an organism. One example of stem cells is hematopoietic stem cells (HSCs) that are found in bone marrow. Each HSC can divide so that one of the resulting cells remains an HSC. The other resulting cell continues to divide so as to generate cells that gradually take on specialized characteristics of red blood cells (RBCs), white blood cells (WBCs), and platelets that enter the blood stream.

The present invention relates to MSCs, which have many of the properties of stem cells, but do not give rise to hematopoietic cells (e.g., RBCs, WBCs, and platelets). Instead, MSCs give rise to non-hematopoietic precursor cells that become bone cells, cartilage cells, muscle cells, lung cells, or, under specialized circumstances, cells of the central nervous system, or other types of cells. An important advantage of MSCs for cell and gene therapy is that stem cells such as MSCs are "young cells," that can replace aging cells in the body. Moreover, if a gene defect is corrected in an MSC of a patient, the correction can persist in the patient upon reintroduction of the stem cell into the patient for as long as the patient lives. In addition, a gene may be delivered to an MSC for expression in a desired tissue in which the MSC may finally reside, thereby correcting a deficiency in the individual into which the cells are introduced.

The MSC culture/expansion methods described herein solve an essential problem in the use of stem cells for treatment of human diseases. That is, prior to the disclosure provided herein, most stem cells were difficult to isolate and to expand in culture (i.e., it was difficult to induce them to proliferate in sufficient number). For that reason, adequate numbers of multipotential cells generally could not be obtained for therapeutic uses. The results disclosed herein demonstrate that starting with a small bone marrow aspirate obtained under local anesthesia (e.g., 20 milliliters or about two-thirds of an ounce), enough MSCs can be grown and isolated to allow a large variety of therapies and manipulations to be performed using those MSCs.

Another difficulty encountered using MSCs cultured using prior art culture/expansion methods is that MSCs produced using such methods retain reduced differentiative capacity. That is, only a relatively small fraction of such cells retain the ability to differentiate to become one of a variety of cell types; many or most such cells are terminally differentiated or have proceeded along a differentiative course whereby the number of different cell types into which they can differentiate has become limited. MSCs produced by the culture/expansion methods of the invention retain their ability to differentiate into one of a variety of cells to a greater degree than MSCs produced using prior art methods.

Under prior art culture conditions, MSCs are plated at initial densities ranging from about 1,000 to 10,000 cells per square centimeter, and the cells expand in number by about 3-fold to 10-fold over the course of approximately 14 days. As demonstrated by the data disclosed herein, MSCs cultured according to the method described herein increase in number by about 300-fold to 2,000-fold over a period of about 10 to 14 days. High numbers of multipotential cells are obtained in the method of the invention, thereby providing sufficient cells for purposes of cell therapy or gene therapy, for example.

The present invention is also useful for obtaining MSCs that express an exogenous gene, so that the MSCs can be used, for example, for cell therapy or gene therapy. That is, the present invention allows production of large numbers of cells which express the exogenous gene. The exogenous gene can, for example, be an exogenous version of an endogenous gene (i.e., a wild type version of the same gene can be used to replace a defective allele comprising a deleterious mutation). The exogenous gene is usually, but not necessarily, covalently linked with (i.e., "fused with") one or more additional genes. Exemplary 'additional' genes include a gene used for "positive" selection to select cells that have incorporated the exogenous genes, and a gene used for "negative" selection to select cells that have incorporated the exogenous gene into the same chromosomal locus as the endogenous gene.

Because the present disclosure makes it possible to rapidly and extensively expand MSCs in culture while preserving their multipotentiality, skilled artisans are enabled to use MSCs generated by gene engineering protocols, even where those uses were not previously feasible using MSCs cultured/expanded by prior art methods.

Under conditions known in the art, MSCs can be induced to differentiate into fat cells, cartilage cells, lung cells, bone cells, cells of the central nervous system, and other cell types by selection of culture conditions known to lead to differentiation of MSCs into cells of a selected type. For example, either of the growth media described herein in Example 1 can be used for inducing differentiation of MSCs into osteoblasts or into adipocytes. Other conditions known in the art can be used to induce MSCs to differentiate into chondrocytes or myocytes, (e.g. methods described in Wakitani et al., 1995, Muscle and Nerve 18: 1417-1426; Prockop, 1997, Science 276:71-74; Friedenstein et al., 1987, Cell Tissue Kinet. 20:263-272; Kuznetsov et al., 1997, J. Bone Miner. Res. 12:1335-1347; Bruder et al., 1997, J. Cell Biochem. 64:278-294; Kelly et al., 1998, Endocrinology 139:2622-2628).

MSCs cultured or expanded as described in this disclosure can be used, before or following differentiation into selected cell types, to treat a variety of disorders known in the art to be treatable using MSCs (i.e., MSCs harboring an exogenous gene or MSCs which do not harbor an exogenous genes). Examples of such disorders include bone disorders (e.g., osteoporosis and fracture), joint disorders (e.g., arthritis and rheumatism), and central nervous system (CNS) disorders (e.g., brain trauma, Huntington's disease, Alzheimer's disease, Parkinson's disease, spinal cord injury, stroke, multiple sclerosis, surgical ablation, and head trauma).

The invention also includes one or more growth factors produced by MSCs at least when they are growing at low cell density. When one or more of these growth factors are present with MSCs in culture at least at a certain level, the rate of proliferation of the MSCs is increased. A growth factor can be provided as a component of a conditioned medium, in a partially purified form, or in a substantially purified form, for example. One or more of the growth factors can also inhibit proliferation of MSCs, induce differentiation of MSCs, or both. One or more of the factors can increase proliferation, inhibit differentiation of MSCs, or both.

In addition, as the data described in Example 8 demonstrate, a protein known as Lipocortin II (also known as Annexin II) has been found only in cultures expanded according to the methods of the invention described herein. Thus, the invention includes a method of using this protein to isolated and purify MSCs expanded in culture for use in therapy.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "colony-forming efficiency" and "CFU efficiency" interchangeably mean the ability of MSCs in a sample to form individual colonies in culture, expressed as a percentage or fraction of the total number of MSCs in the sample.

A "growth factor" is a substance or compound that, when present with MSCs in culture, increases the rate or extent of MSC proliferation.

A "growth surface" is any substrate capable of supporting cell growth, attachment, or both. Such term encompasses plastic, glass, fibers, gelatinous substrates, and the like.

The terms "initial density" and "initial cell density" of MSCs in culture interchangeably mean the number of cells per unit area of the growth surface in the presence of which the MSCs are cultured at the time the MSCs are first added to the container comprising the growth surface.

A "growth medium" is a composition of matter which comprises the minimal nutrients necessary to sustain proliferation of MSCs.

"Expandability" of MSCs means the capacity of the MSCs to proliferate (i.e., expand in number or undergo population doublings).

By the term "isolated," as used herein, is meant an entity (e.g., a protein or cell) which has been substantially separated from similar entities (e.g., other proteins or other cells) which naturally accompany it in its naturally-occurring form. For example, isolated MSCs are MSCs which have been separated from at least certain other bone marrow cells with which they normally occur (e.g. in bone marrow).

"Marrow stromal cells" ("MSCs") are stem-like cells that are precursors of non-hemopoietic tissues and that can be isolated from bone marrow. MSCs have been described in the prior art (e.g., Friedenstein et al., 1976 Exp. Hematol. 4:267-274; Friedenstein et al., 1987, Cell Tissue Kinetics 20:263-272; Castro-Malaspina et al., 1980, Blood 56:289-301; Mets et al., 1981, Mech. Aging Develop. 16:81-89; Piersma et al., 1985, Exp. Hematol. 13:237-243; Owen et al., 1988, Cell and Molecular Biology of Vertebrate Hard Tissues, Ciba Foundation Symposium, Chichester, U.K., 42-60; Caplan, 1991, J. Orthoped. Res. 9:641-650; Prockop, 1997, Science 276:71-74).

"Multipotentiality," "differentiability," and grammatical forms thereof refer to the capacity of an MSC to become one of a variety of cell types (i.e., to differentiate into a cell of that type).

As used herein, a "transfected MSC" or a "transduced MSC" is an MSC to which a gene construct has been provided using any technology used to introduce nucleic acid molecules into cells such as, but not limited to, classical transfection (calcium phosphate or DEAE dextran mediated transfection), electroporation, microinjection, liposome-mediated transfer, chemical-mediated transfer, ligand mediated transfer or recombinant virus vector transfer.

As used herein, the terms "heterologous nucleic acid" and "recombinant nucleic acid" are used interchangeably and mean genomic DNA, cDNA, synthetic DNA or RNA, mRNA or antisense DNA or RNA which is introduced into an MSC. The recombinant genetic material can be heterologous genetic material or can be an additional copy or copies of genetic material normally found in the individual or animal from which the MSC was obtained.

As used herein, "promoter/regulatory sequence" means a DNA sequence which is required for specific expression of a gene operably linked with the promoter/regulatory sequence. In some instances, this sequence can be the core promoter sequence and in other instances, this sequence can also include an enhancer sequence and other regulatory elements which are required for expression of the gene in a tissue-specific or otherwise inducible or constitutive manner.

By describing two nucleic acid sequences as "operably linked" as used herein, is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

"Expression construct" refers to a DNA construct comprising a recombinant polynucleotide comprising expression control sequences operatively linked to a nucleotide sequence to be expressed. An expression construct comprises sufficient cis-acting elements for expression; other elements for expression can be supplied by the host cell or in an in vitro expression system. Expression constructs include all those known in the art, such as cosmids, plasmids (e.g., naked or contained in liposomes) and viruses that incorporate the recombinant polynucleotide.

A compound, e.g., a nucleic acid, a protein or polypeptide is "substantially purified" when it is essentially free of naturally associated components or when it is separated from the native contaminants which accompany it in its natural state. Thus, a "substantially pure" preparation of a protein or a polypeptide, as used herein, refers to a protein or polypeptide which has been purified from components with which it is normally associated in its naturally occurring state.

DESCRIPTION

The invention is based on the discovery that expansion of human marrow stromal cells (MSCs) can be improved, relative to prior art culture/expansion methods, by culturing the MSCs at an initially low cell density. In prior art culture/expansion methods, very high initial cell densities (e.g. greater than about 1000 and preferably approximately 5,000 cells per square centimeter) are used for culturing cells. In contrast, in the methods of the invention, the initial cell density that is used for expansion of MSCs should not be greater than about 50 cells per square centimeter, and is preferably about 3 cells per square centimeter. Culturing MSCs at these low initial cell density values allows a greater degree of expansion of MSCs than prior art methods.

The invention includes a method of inducing proliferation of isolated human MSCs in vitro. This method comprises providing the isolated MSCs and a growth medium to a growth surface such that the initial density of the isolated MSCs is less than about 50 (25, 12, 10, 6, or 3) cells per square centimeter of growth surface, and is preferably at least about 0.5 cells per square centimeter. The MSCs can be isolated by substantially any MSC isolation method known in the art, such as that described herein in Example 1. The growth surface can be substantially any surface with which MSCs can adhere (e.g., glass or plastic surfaces), such as one or more walls of a culture vessel (e.g., a tissue culture flask or roller bottle) or a substrate (e.g., a bead, fiber, porous matrix, sponge, tube, etc.) maintained in contact with a growth medium. When the MSCs are incubated in the presence of the surface under growth-promoting conditions, the MSCs proliferate.

Growth-promoting conditions include any set of conditions (temperature, growth medium composition, atmosphere, humidity, degree of agitation, etc.) under which MSCs normally proliferate. None of these conditions are critical. The temperature should be near that of normal human body temperature (i.e., about 37° C.), but can be any temperature at which MSCs can proliferate (e.g., 30 to 43° C.). The growth medium can be any liquid medium which contains nutrients and factors sufficient to support proliferation of MSCs. Such media contain, for example, a carbon source (e.g., glucose) and minimal essential nutrients, and preferably contain one or more of a mammalian serum (e.g., fetal calf serum), an antibiotic (e.g., penicillin or streptomycin), and L-glutamine (i.e. to improve amino acid supply for protein biosynthesis). The mammalian serum can be used at a concentration of 10% to 20%, by volume, of the total growth medium. The serum is preferably pre-screened to ensure that it supports vigorous growth of MSCs; some lots, even lots provided from the same supplier, do not support vigorous growth of MSCs. Alternatively, the mammalian serum can be replaced with one or more growth factors (e.g. fibroblast growth factor, platelet derived growth factor, insulin growth factor, or endothelial growth factor). The growth medium can, for example, be Minimal Essential Medium-alpha without deoxyribonucleotides or ribonucleotides, supplemented with fetal calf serum antibiotics, and L-glutamine, as in the examples herein. Other exemplary growth media include, for example, Dulbecco's minimal essential medium, and others which have been described in the art (e.g., media disclosed in references discussed in the Background section of this disclosure). The growth medium is preferably replaced one or more times (e.g., every 3 or 4 days) during incubation of the MSCs, growth surface, and growth medium. MSCs can be grown in an air atmosphere, or an air atmosphere supplemented with 5% $CO_2$, for example.

Sources of MSCs and methods of obtaining MSCs from those sources have been described in the art (e.g., Friedenstein et al., 1976 Exp. Hematol. 4:267-274; Friedenstein et al., 1987, Cell Tissue Kinetics 20:263-272; Castro-Malaspina et al., 1980, Blood 56:289-301; Mets et al., 1981, Mech. Aging Develop. 16:81-89; Piersma et al., 1985, Exp. Hematol. 13:237-243; Owen et al., 1988, Cell and Molecular Biology of Vertebrate Hard Tissues, Ciba Foundation Symposium, Chichester, U.K., 42-60; Caplan, 1991, J. Orthoped. Res. 9:641-650; Prockop, 1997, Science 276:71-74; Beresford et al., 1992, J. Cell Sci. 102:341-351; Cheng et al., 1994, Endocrinology 134:277-286; Rickard et al., 1994, Develop. Biol. 161:218-228; Clark et al., 1995, Ann. N.Y. Acad. Sci. 770:70-78). MSCs can be obtained from substantially any bone marrow including, for example, bone marrow obtained by aspiration of the iliac crest of human donors. Methods for obtaining bone marrow from donors are well known in the art.

An important aspect of the method of inducing proliferation of isolated MSCs, as described herein, is the initial density of the isolated MSCs. The initial density should be less than about 50 cells per square centimeter of growth surface, and is preferably less than about 25, 12, 10, 6, or 3 cells per square centimeter. Preferred ranges of initial density values (in cells per square centimeter) include 0.5-1.0 and 1.5 to 3. In contrast to prior art MSC culture/expansion methods, the low initial cell density of the methods of the invention promotes rapid and extensive expansion of the MSC population seeded on the growth surface (i.e., the low cell density maintains the proliferative capacity of the MSCs at a high level). The low initial cell density allows a significant degree (e.g., at least 10-fold, 50-fold, 100-fold, 200-fold, 300-fold, or more) expansion of the MSC population. Prior art methods use much higher (1,000-10,000 cells per square centimeter) values for initial cell density, and result in a much lower degree of MSC expansion (e.g., about 3-fold).

Another important difference between the MSCs generated by expansion using the methods described herein and MSCs generated by prior art culture/expansion methods is that MSCs expanded as described in this disclosure retain a high degree of differentiability. That is, a greater proportion of MSCs expanded by culturing them at a low initial cell density retain the ability to differentiate into one of numerous cells types (e.g., osteoblasts, adipocytes, neural cells, etc.) than MSCs cultured by prior art methods. As indicated above, the initial cell density at which the MSCs are expanded is an important determinant of the differentiability of the expanded MSCs. Another important determinant of the differentiability of the expanded MSCs is the period of time that elapses between seeding the MSCs on the growth surface and harvesting the expanded MSCs. Generally, the earlier the MSCs are harvested, the greater their differentiation potential will be. MSCs expanded using the method described herein can be maintained in culture for about 3 to 10 days, and are preferably harvested after not more than about 14 days or 10 days.

The MSC expansion method can be performed once (i.e., by seeding MSCs on a growth surface in the presence of a growth medium, and then harvesting the cells after, e.g., 10 days). Alternatively, the method can be performed in series, meaning that the method is performed once, expanded MSCs are harvested, and then the expanded MSCs and a growth medium are provided to a second growth surface, where the initial density of the expanded MSCs is less than about 50 (25, 12, 10, 6, or 3) cells per square centimeter of second growth surface. After incubating the MSCs, growth medium, and second growth surface, the MSCs will be further expanded. Of course, the twice-expanded MSCs can be harvested and subjected to one or more additional rounds of expansion, using the same method. There is no theoretical limit to the number of rounds of expansion and harvest that can be performed. However, it is recognized that because each expansion/harvest cycle will significantly increase the number of MSCs available (i.e., by 10-fold, 100-fold, or more), a geometrically increasing amount of growth medium and growth surface will be required during sequential expansion/harvest cycles if all expanded MSCs are to be further expanded. Thus, it is recognized that, for most applications, no more than about 10 cycles of expansion and harvest will normally be necessary, and as few as 1, 2, 3, or 4 cycles will be sufficient for many applications (e.g., cell therapy or gene therapy).

The MSCs that are expanded using the method described herein can, for example, be MSCs that are obtained from an individual for the purpose of expanding the MSCs prior to returning the MSCs to the same individual. Alternatively, the MSCs can be obtained from a donor individual for the purpose of expanding the MSCs prior to providing them to a recipient individual. The recipient and donor are preferably genetically related, share common blood cell or other cell surface antigens, or both. The MSCs that are expanded can alternatively be MSCs that have recently (e.g., within hours, days, weeks, or months) been isolated from an individual or MSCs that have been stored (e.g., frozen in liquid nitrogen for a period of years, months, or weeks) in a metabolically depressed or dormant state prior to expansion. In some embodiments, an exogenous nucleic acid can be provided to the MSCs prior to expanding the cells according to the methods described in this disclosure. Methods of providing an exogenous nucleic acid to a MSC and methods of using such MSCs are described, for example, in co-pending U.S. application Ser. No. 09/028,395, and in International PCT Application Nos. PCT/US96/04407 and PCT/US99/03897 which are, as with all documents referenced herein, incorporated by reference.

Isolated MSCs are useful in a variety of clinical settings including, for example, all of those described in the Background section of this disclosure. For example, MSCs can be used as delivery vehicles for the administration of nucleic acid which is a therapeutic product or a nucleic acid encoding a therapeutic product (i.e., an RNA or protein molecule) to a human. For example, MSCs can be transfected or transduced using a suitable nucleic acid, preferably one operably linked with a suitable promoter/regulatory sequence. When the nucleic acid is expressed in an MSC, a therapeutic RNA or protein is produced which is of benefit to the human. Delivery of a nucleic acid to MSCs is accomplished using standard technology, such as using viral gene transfer described, for example, in Verma et al. (1997, Nature 389:239-242).

More specifically, in some aspects of the invention, an individual afflicted with a disorder that is characterized by a genetic defect can be treated by one or more of supplementing, augmenting, or replacing defective or deficient cells with cells that correctly express a normal cell gene. The cells which are to be introduced into the individual can be derived from MSCs obtained from a normal matched donor, or they can be MSCs obtained from the individual to be treated. The cells can be genetically modified to correct the defect.

An example of a disorder for which administration of MSCs is useful for treating the disorder is brain trauma. MSCs obtained from a normal matched donor can be administered to an individual who has experienced brain trauma or stroke. Following administration, the MSCs can differentiate into normal brain cells that replace or supplement the affected brain cells in the individual. The normal cells will compensate for the affected brain cells, restoring complete or partial normal function.

In another aspect, MSCs are isolated from an individual afflicted with a brain tumor, and a gene capable of killing or otherwise arresting the replication of the tumor cells is inserted into the isolated MSCs. The transfected cells are then re-introduced into the individual. One or both of growth and replication of the tumor cells can be arrested and apoptosis of the tumor cells can be induced.

In one aspect of the invention, an individual afflicted with a disorder of the central nervous system can be treated as follows. Isolated MSCs are obtained, and they are expanded and are systemically administered to the individual. Some of the isolated/expanded MSCs develop into normal cells. Thus, re-population of the central nervous system tissue with an expanded and rejuvenated population of MSCs facilitates correction of the defect in the central nervous system tissue. Also, MSCs can be differentiated into, for example, muscle cells, bone cells, cartilage cells, fat cells, and the like, using methods known in the art, prior to administration of the marrow stromal cells to the patient.

In addition to replacing defective cells with repaired cells or normal cells from matched donors, the method of the invention can also be used to facilitate expression of a desired protein that, when secreted in the human, has a beneficial effect. For example, MSCs can be isolated, expanded using the method of the invention, furnished with a gene encoding a desired protein, and introduced into the central nervous system or other tissue of an individual. Expression of the desired protein in the desired target tissue of the individual exerts a therapeutic effect in the individual. This aspect of the invention relates to gene therapy in which therapeutic proteins are administered to an individual. Alternatively, MSCs can be isolated from an individual afflicted with a disease and a mutated gene in the individual's MSCs can be inactivated or replaced in situ with a normal gene. Such manipulations usually require extensive selection for correctly modified cells, and therefore the extensive expansion of the modified MSCs that is enabled by the present invention. After the modified MSCs are isolated and expanded, they can be returned to the same individual for treatment of the disease.

MSCs are particularly useful in cell therapeutic compositions, because in addition to being suitable hosts for expressing heterologous genes and producing heterologous proteins, MSCs expanded as disclosed herein retain their multipotentiality and can repopulate a variety of different tissues. Furthermore, MSCs have a very high viability when implanted in locations that lack a direct vascular blood supply. Moreover, MSCs can be easily and readily obtained, and they rapidly expand in culture using the method of the present invention to produce large numbers of MSCs, making them a good source of an adequate supply of useful cells for cell therapeutics.

Another aspect of the invention relates to the discovery that human MSCs produce one or more soluble growth factors when they are cultured, at least when they are cultured at a low (i.e., less than 50, 25, 12, 10, 6, or 3 cells per square centimeter) initial density. At least one of these growth factors has a molecular weight of about 30,000, and can be at least partially purified from MSC culture medium using size-exclusion HPLC, for example. Addition of this growth factor to human MSC cultures enhances one or both of the rate and extent of MSC proliferation. At least one other growth factor has a molecular weight of about 10,000, and can also be at least partially purified from MSC culture medium using size-exclusion HPLC. Addition of this growth factor to human MSC cultures inhibits one or both of the rate and extent of MSC proliferation. One or more of the growth factors can induce human MSCs to differentiate into cells of various types. Also, on or more of the factors may allow the MSCs to proliferate without differentiating.

One or more of the growth factors can be added to human MSC cultures in substantially purified form, in partially purified form, or in the form of a conditioned medium. Such a conditioned medium can be generated by culturing human MSCs in a growth medium for a period of hours or days (e.g., at least about 3 or 6 days in an MSC culture having a cell density of 12-10,000 MSCs per square centimeter), during which period the MSCs secrete the growth factor into the growth medium, thereby transforming the growth medium into a conditioned medium. Conditioned medium in which MSCs are cultured for about 14 days can contain multiple growth factors produced by the MSCs including, for example, the growth factor described above having a molecular weight of about 30,000 and the growth factor described above having a molecular weight of about 10,000. One or more additional factors may also be present.

The invention therefore includes a method of enhancing in vitro proliferation of isolated human MSCs growing on a surface in the presence of a growth medium. The method comprises supplementing the growth medium with a growth factor secreted by human MSCs grown, such as at a low initial density. For example, the growth factor can be added to the growth medium by supplementing the growth medium with a conditioned medium obtained from a culture of human MSCs ("producer MSCs") which are grown on a second surface at low density (e.g., at an initial density of at least about 0.5 or 1.5 cells per square centimeter) and which are incubated for at least several hours (but preferably more than a day, such as about 3-6 days).

It is understood that the amount of growth factor produced by producer MSCs can be roughly proportional to the number of MSCs that are present. For this reason, very low producer cell densities (e.g., <0.5 cells per square centimeter) are not preferred. Instead, the producer human MSCs can be grown on the second surface at a higher initial density, such as an initial density of at least about 12 cells per square centimeter. Useful densities of producer cells for generating the growth factor include, for example, 12-10,000 cells per square centimeter.

It is also understood that the amount of growth factor produced by producer MSCs can increase during at least the first several hours or days of MSC culture. Thus, it is preferred that producer human MSCs are incubated for at least several hours, and preferably for at least a few days (preferably, 3-21 days) prior to harvesting the conditioned medium containing the growth factor.

The conditioned medium is preferably used in a form in which the producer cells have been separated from the growth medium. Growth factor produced by human MSCs obtained from one individual can be provided to a different individual, preferably after removing substantially all (e.g., >90%, >95%, >99%, or >99.9%) producer cells from the conditioned medium. Furthermore, the growth factor can be purified from the conditioned medium by standard protein purification methods. Growth factor activity can be assessed in fractionated (e.g., by liquid chromatographic methods, by precipitation methods, by centrifugation methods, etc.) conditioned medium by determining the MSC proliferation-enhancing activity of individual fractions of the fractionated medium. Fractions which exhibit significant MSC proliferation-enhancing activity can be pooled or used individually, either to enhance MSC proliferation, or as the starting material for further purification. The conditioned medium or, preferably, partially purified or substantially purified growth factor can be provided to a human patient in order to induce proliferation of MSCs in the individual. The cultured medium or growth factor is preferably administered intravenously, but can, optionally, be administered by any other method of administration which results in delivery of the factor to human MSCs in vivo (e.g., intramuscular injection, injection into marrow-containing spaces, subdermal injection, implantation of a degradable growth factor-containing mass, etc.).

It is recognized that, at least under certain circumstances, the growth factor can inhibit MSC proliferation, such as at very high concentrations of the growth factor. Thus, if a dose of growth factor administered to a human does not achieve the desired MSC proliferation-inducing effect, the dose can be modified (i.e., increased or decreased) until the desired effect is achieved. Furthermore, proliferation of human MSCs in culture can be enhanced by diluting (e.g., at discrete times or continuously) or replacing the culture medium with which the MSCs are incubated. Alternatively, purification of conditioned medium may provide several different growth factors, some of which can increase proliferation of MSCs when administered to a patient. Others of these growth factors can promote differentiation of MSCs into specific cell types, such as bone cells (osteoblasts). A factor that promoted differentiation of MSCs into osteoblasts, for example, is useful for treating a bone disorder such as osteoporosis.

As described in the examples herein, the expandability of human MSCs (i.e., their capacity to produce subsequent generations of MSCs by cell growth and division) can be accurately correlated with the ability of the MSCs to form colonies in culture. The invention thus includes a method of assessing the expandability of human MSCs in vitro, the method comprising incubating the cells on a surface in the presence of a growth medium at a low density (e.g., at an initial density of less than about 50, 25, 12, 10, 6, or 3 cells per square centimeter of surface) and thereafter assessing the colony-forming efficiency of the MSCs. The expandability of the MSCs is approximately proportional to the colony-forming efficiency of the MSCs. The MSCs can be cultured for from 1 hour to about 14 days, but are preferably cultured for several days prior to counting colonies formed by the MSCs (e.g., 5 or 6-10 days if colonies are to be counted following staining with Crystal Violet).

Colony-forming efficiency can be assessed, for example, by visual inspection of cultured MSCs coupled with counting of the number of colonies formed. The colony-forming efficiency can be expressed as a percentage of MSCs by dividing the number of colonies formed by the number of cells seeded onto the growth surface. Of course, the number of colonies formed can be assessed by any other (e.g., automated) method of colony counting.

The colony-forming efficiency of cultured MSCs obtained from a first sample or source of MSCs can be compared with the colony-forming efficiency of MSCs obtained from a second sample or source of MSCs. The sample or source which includes MSCs having the higher colony-forming efficiency will generally have the yield MSCs having greater expandability than the other sample or source. Alternatively, colony-forming efficiency of cultured MSCs obtained from a sample or source of MSCs can be compared with data generated using another source or sample of MSCs cultured under similar (or, preferably, the same) conditions. Also preferably, the expandability of MSCs obtained from the other source or sample is known. The data can be a reference curve (e.g., the plot shown herein in FIG. 2) which indicates the relationship between colony-forming efficiency and expandability of MSCs cultured under a set of similar or identical conditions.

Although the invention has been exemplified using human MSCs, the MSCs can, alternatively, be those of any animal which comprises MSCs. The present invention encompasses MSCs of other mammals, such as other primates and other mammals which can provide a convenient or plentiful supply of bone marrow (e.g., cows, sheep, pigs, etc.) for example. Also, the growth factors may be obtainable from other sources, including other biological systems or the products of genes that are isolated and then expressed in a variety of systems such as bacteria, yeast, plants, insect cells, mammalian cells, or transgenic animals.

As the data presented in Example 8 demonstrate, a protein known as Lipocortin II (also know as Annexin II) is a surface protein that has been identified in the present invention to be found only in cultures expanded as above. Thus, the invention includes a method of isolating and purifying expanded MSCs using this protein. The method comprises using antibody against this protein to isolated and purify cells using common immunologic technology available in the art.

EXAMPLES

The invention is further described in detail by reference to the following experimental examples. These examples are provided for purposes of illustration only, and are not limiting unless otherwise specified. Thus, the invention is not limited to the following examples, but rather, encompasses all variations which are evident as a result of the teaching provided herein.

Example 1

Propagation and Senescence of Human Marrow Stromal Cells in Culture

Marrow stromal cells (MSCs) were isolated from bone marrow aspirates obtained from the iliac crest of normal volunteers. The cells were isolated by virtue of their ability to adhere to plastic, passaged in culture, and stored frozen. Some samples expanded through over 15 cell doublings from frozen cell stocks. Other samples ceased replicating after about 4 cell doublings.

The data disclosed in this example demonstrate that replicative potential of the cells in culture was best predicted by a simple colony-forming assay in which samples from early passages were plated at low densities of about 10 cells per square centimeter. Samples which exhibited high colony-forming efficiency exhibited the greatest replicative potential. Colonies obtained by plating early passage cells at low density varied in size and morphology. Large colonies readily differentiated into osteoblasts and adipocytes when incubated in the appropriate medium. Thus, the data disclosed in this example demonstrate that, although MSCs obtained from bone marrow aspirates from normal volunteers vary widely in their expandability in culture, the expandability of those MSCs can be predicted by a simple assay which detects colony-forming units (CFUs).

In addition, the data disclosed in this example demonstrate that, as MSC samples were expanded in culture plated at a high initial cell density and approached senescence, the MSCs retained their ability to differentiate into osteoblasts. However, such MSCs failed to differentiate into adipocytes. The loss of multipotentiality following serial passage in culture may have important implications for the use of expanded MSCs for cell and gene therapy.

The materials and methods used in the experiments presented in this example are now described.

Isolation and Culture of MSCs by High Density Plating

Human MSCs were obtained from 20 milliliter aspirates taken from the iliac crest(s) of normal donors ranging in age from 19 to 49 years. Each 20 milliliters of aspirate was processed by first diluting the aspirated marrow with 20 milliliters Hank's balanced salt solution (HBSS; Gibco), and then washing the marrow by gently inverting the mixture several times. About 10 milliliters of ficoll (Ficoll-Paque; Pharmacia) was layered beneath 40 milliliters of sample, and the samples were centrifuged at 2500×g for 30 minutes at room temperature. The mononuclear cell (MNC) layer was removed from the gradient interface, and the cells were washed using HBSS. The cells were centrifuged at 1500×g for 15 minutes, and the cell pellets were re-suspended in complete medium. Complete medium comprised Minimum Essential Medium-alpha medium without deoxyribonucleotides or ribonucleotides (Gibco), supplemented with 20% (v/v) fetal calf serum (FCS, Atlanta Biologicals, Atlanta, Ga.), 100 units per milliliter penicillin, 100 micrograms per milliliter streptomycin (Gibco), and 2 millimolar L-glutamine (Gibco). The FCS was lot-selected for rapid growth of MSCs.

Following this treatment, the cells were plated in a 25-square centimeter tissue culture flask (Nunc) and incubated at 37° C. in the presence of a humidified 5% $CO_2$ atmosphere. After 24 hours, non-adherent cells were removed. Adherent cells were twice washed vigorously with phosphate buffered saline (PBS) and shaken to remove adherent hematopoietic precursors, after which fresh complete medium was added. The medium was replaced every three or four days, and the cells were grown to about 70 to 90% confluence.

The cells were harvested by contacting the cell layer with 0.25% (w/v) trypsin and 1 millimolar EDTA (Gibco) for 5 minutes at 37° C. The cells were re-plated in a 75-square centimeter flask, again grown to confluence, and the cells were harvested. About 8 milliliters of complete medium was mixed with the trypsinized cells to inactivate the trypsin, and the cells were counted using an automated instrument (Coulter) or a hematocytometer. Harvested cells were slowly frozen in 5% (v/v) DMSO and 30% (v/v) FCS, and were stored frozen in liquid nitrogen. To expand the cells through successive passages, the cells were plated at 5,000 cells per square centimeter (i.e., about a 1:3 dilution), grown to near confluence, and harvested using the same protocol. At the end of each passage, the cells were counted using a hematocytometer to calculate cell doublings.

CFU-F Assays

MSCs expanded in culture to about 70 to 90% confluence were harvested with trypsin-EDTA and counted using a hematocytometer. A glass Pasteur pipette was flamed at its tip to reduce its diameter, and the cells were drawn through the narrowed pipette several times to ensure cell separation. The cells were diluted in complete medium and plated at an initial density of about 10 cells per square centimeter in 100 millimeter diameter (ca. 80 square centimeter) tissue culture dishes (Falcon). After incubation for 10 to 14 days at 37° C. in the presence of a humidified 5% $CO_2$ atmosphere, the cells were washed using PBS. The cells were stained using 0.5% (w/v) Crystal Violet in methanol for 5 to 10 minutes at room temperature. The cells were washed twice with PBS and visible colonies were counted. To isolate colonies, unstained colonies were recovered using cloning cylinders and trypsin-EDTA.

Osteogenic Differentiation of MSCs

MSCs were grown to 70 to 90% confluence in wells of 12-well tissue culture plates and then incubated in osteogenic medium containing $10^{-8}$ molar dexamethasone, 0.2 millimolar ascorbic acid (Sigma Chemical Co., St. Louis, Mo.), and 10 millimolar beta-glycerolphosphate (Sigma Chemical Co., St. Louis, Mo.). The medium was replaced every three to four days, and deposition of mineral was observed after 2 to 3 weeks. To assess mineralization, cultures were washed with PBS and fixed in a solution of ice-cold 70% ethanol for 1 hour. The cultures were rinsed with water and were then stained as described in Stanford et al. (1995, J. Biol. Chem. 270:9420-9428) for 10 minutes using 1 milliliter of 40 millimolar Alizarin red (pH 4.1; Sigma Chemical Co., St. Louis, Mo.), with rotation. The cultures were rinsed two or three times with PBS to reduce non-specific staining. Because the stained mineral was uniformly distributed and obscured the cells, mineralization was assayed by examining multiple fields in order to calculate the mineralized area as a percentage of the total area of the confluent cultures.

Adipogenic Differentiation of MSCs

MSCs in 85% to 95% confluent cultures, as described (Kelly and Gimble, 1998, Endocrinology, 139:2622-2628), were incubated in complete medium supplemented with MHI (which comprises 0.5 micromolar hydrocortisone, 0.5 millimolar isobutylmethylxanthine, and 60 micromolar indomethacin). The medium was replaced every 3 or 4 days. Cells containing lipid vacuoles were observed after 2 to 3 weeks. The cells were washed using PBS and fixed in 10% formalin for 10 minutes. The cells were stained for about 10 to 15 minutes using fresh Oil red-O solution, as described (Houghton et al., 1998, Bone 22:7-16). The Oil red-O solution was prepared by vigorously mixing 3 parts stock solution (0.5% in isopropanol; Sigma Chemical Co., St. Louis, Mo.) with 2 parts water for 5 minutes, and then filtering the solution through a 0.4-micron filter. The plates were washed three times with water. The percentage of adipocytes was assayed by counting 50 to 100 cells in multiple fields.

The results of the experiments presented in this example are now described.

CFU-F Assays Predict Life Span in Culture

Nucleated cells were isolated from bone marrow aspirates of normal donors, and MSCs were isolated by virtue of their ability to adhere to plastic culture dishes. After the cells were grown to confluence, first in a 25-square centimeter flask, and then in a 75-square centimeter flask, frozen cell stocks were prepared. The total number of subsequent population doublings in samples obtained from individual donors was assessed by serial re-plating of the frozen cell stocks. Recent reports indicated that cryopreservation does not significantly alter the properties of either canine MSCs (Hurwitz et al., 1997, Hum. Gene Ther. 8:136-156) or human MSCs (Bruder et al., 1997, J. Cell. Biochem. 64:278-294). Assays by fluorescence activated cell sorting (FACS) of confluent cultures obtained by the first plating of the frozen cells (i.e., second passage) indicated that the cells were negative for CD45, a marker for hematopoietic cells (Clark and Keating, 1995, Ann. New York Acad. Sci. 770:70-78). About 8% of the cells analyzed by FACS were strongly positive for Stro-1 (a cell surface marker used by others to identify early osteogenic progenitor cells in primary human MSC cultures; Simmons and Torok-Storb, 1991, Blood 78:55-62), and the positive cells were in the largest and most granular FACS cell fraction. The remainder of the cells were weakly positive for Stro-1. Therefore, the results described in this example are not consistent with the conclusion that the Stro-1 antibody can be used to identify the earliest progenitors in cultures of MSCs.

Figure 2:
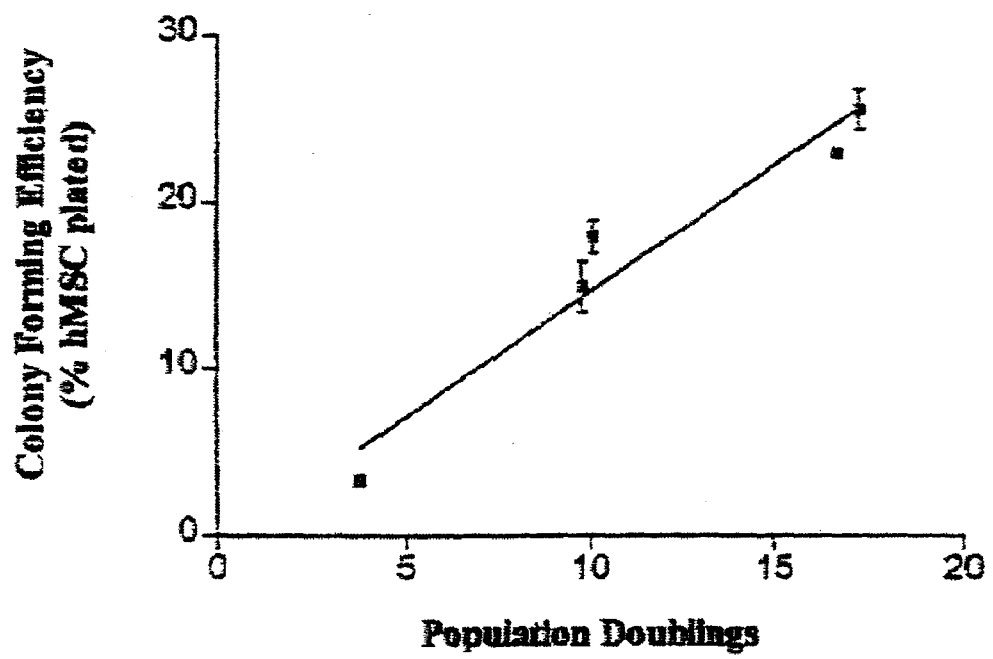
FIG. 2 is a graph depicting the correlation between population doublings and the number of colonies observed in the colony forming unit (CFU) assay described herein following the fourth passage. Bars indicate mean ±standard error of three values for each point.

As indicated in FIG. 1, there was significant variation in the number of population doublings attainable using MSC samples obtained from different donors when the cells were passed by plating at high density. Some MSC samples expanded through over 15 cell doublings from frozen cells stocks. Other MSC samples ceased replicating after about four cell doublings. The replicative potential of the cells was not reflected in their initial growth rate (e.g., compare donor 11 and donor 13 in FIG. 1). Also, the variation was not related to the gender or age of the donors. Assay of cells after the fourth passage demonstrated that there was also significant variation in the number of colonies obtained in a simple CFU assay in which the cells were plated at low density (10 cells per square centimeter). There was a positive correlation between number of mononucleated cells (MNCs) initially plated and the number of CFUs ($r^2$=0.63; n=8; p<0.011) that could be detected, but there was no correlation when duplicate samples obtained at the same time from the same individual were compared. Specifically, there was no correlation between duplicate bone marrow samples obtained from Donors 54, 56 and 57. However, the number of population doublings obtained in culture were closely correlated ($r^2$=0.9419, n=5, p=0.006) with values obtained in the CFU assay, as shown in FIG. 2.

Figure 3A:
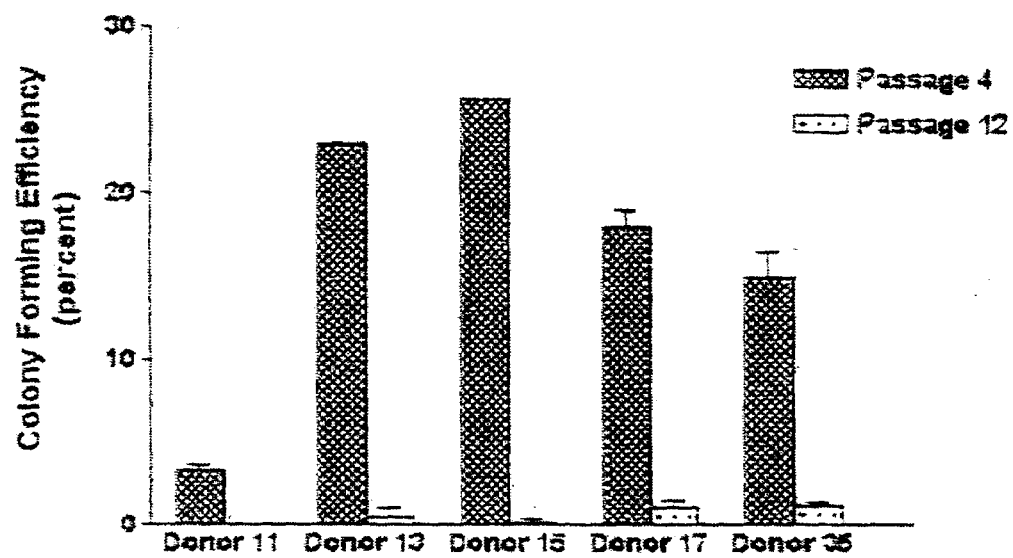
FIG. 3A is a bar graph depicting the decrease in CFUs of MSCs of passages 4 and 12.
Figure 3B:
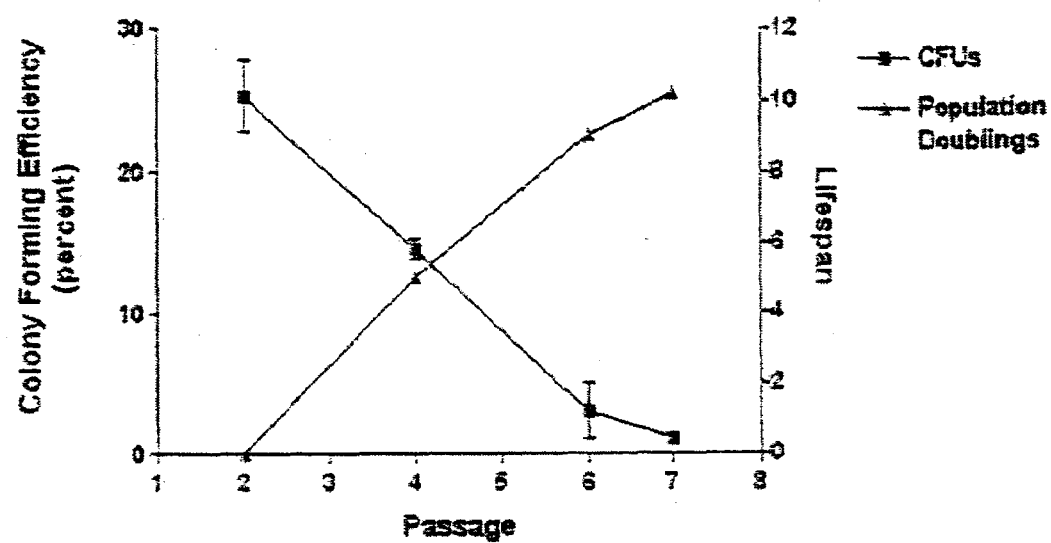
FIG. 3B is a graph depicting the relationship between CFUs and expandability of MSCs (indicated by population doublings) obtained from a single donor as the cells obtained from the donor were passaged. Each value represents the mean ±standard error for three measurements.
Figure 4:
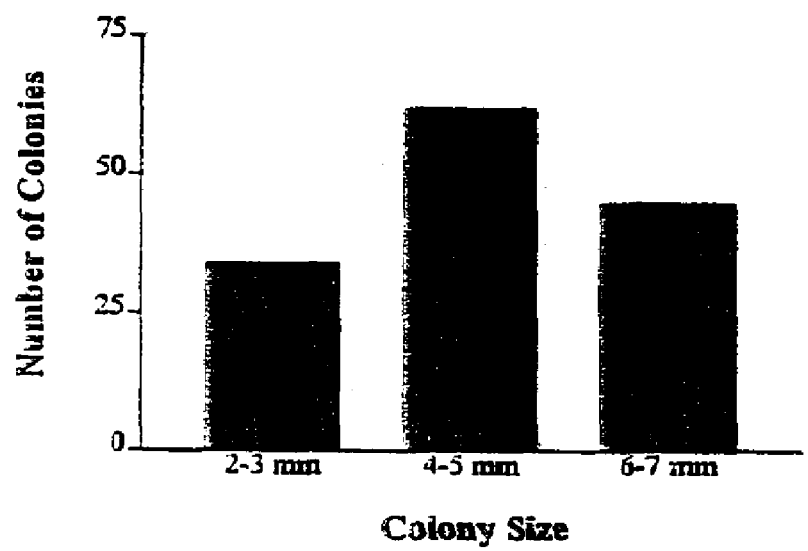
FIG. 4 is a bar graph depicting the size distribution of colonies obtained in a CFU assay. Values are from 35 colonies per plate from 4 donors at passage 2 (n=140). Values are the largest observed diameters of the colonies.

The number of CFUs declined as the MSC cell samples were expanded in culture. The decline of CFUs with passage number was apparent from assays of a single sample (i.e., as shown in FIG. 3A) and from assays of 5 samples obtained from different donors compared at passage 4 and passage 12 (i.e., as shown in FIG. 3B).

MSC CFU-Fs Vary in Size, Morphology and Growth Rate

Figure 6A:
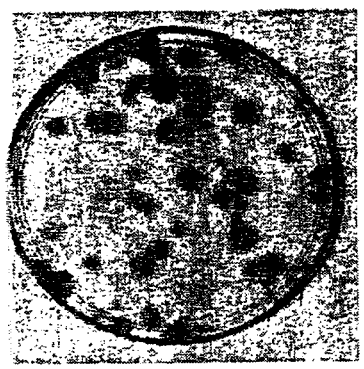
FIG. 6A is an image of a culture plate depicting a CFU assay of MSCs. The plate depicts a CFU assay of passage 4 MSCs obtained from Donor 15.
Figure 6B:
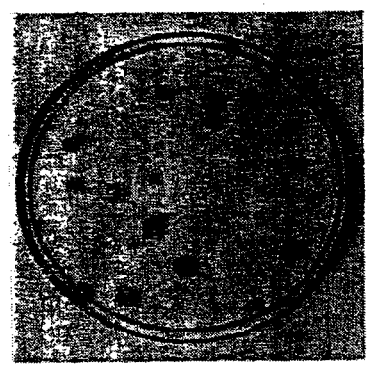
FIG. 6B is an image of a culture plate depicting a CFU assay of MSCs. The plate depicts a CFU assay from passage 4 MSCs obtained from Donor 17.
Figure 6C:
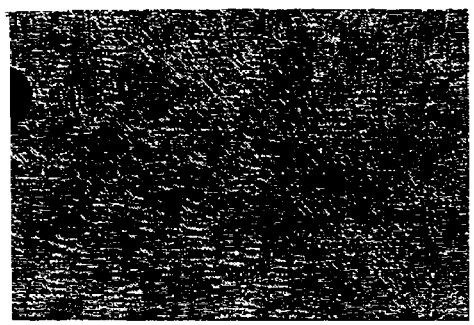
FIG. 6C is an image depicting spindle-shaped cells present in a large colony following CFU assay of passage 2 MSCs obtained from donor 52.
Figure 6D:
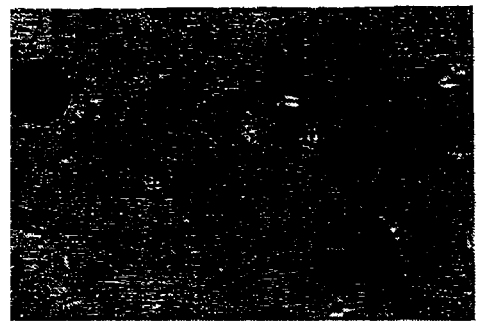
FIG. 6D is an image depicting spindle-shaped cells present in a small colony following the same CFU assay of passage 2 MSCs obtained from donor 52, as depicted in FIG. 6C.
Figure 6E:
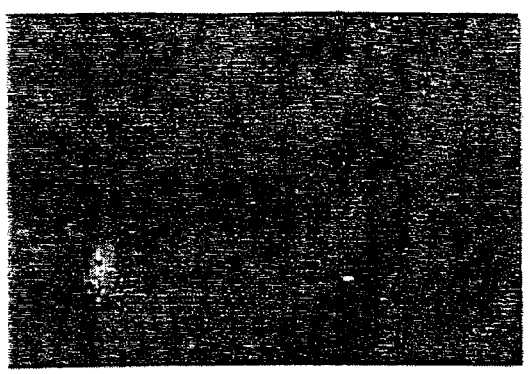
FIG. 6E is an image depicting differentiation into osteoblasts of cells of a large colony obtained from passage 2 of donor 54L, after the cells were grown to confluence and incubated in osteogenic medium for 18 days.
Figure 6F:
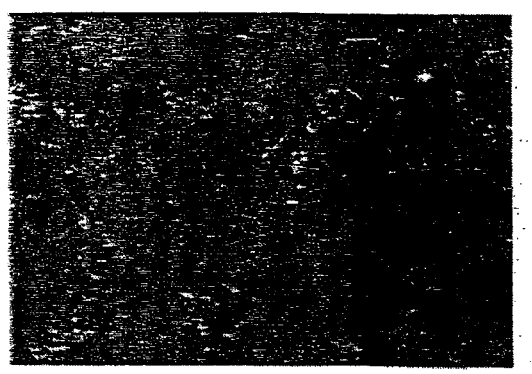
FIG. 6F is an image depicting differentiation into adipocytes of cells from a duplicate culture of cells of the same large colony as in FIG. 6E after incubating the cells in adipogenic medium for 18 days.

Colonies formed by sparsely plated MSCs in CFU assays varied in size (see also Mets and Verdonk, 1981, Mech. Aging Dev. 16:81-89; Bruder et al., 1997, J. Cell. Biochem. 64:278-294). As indicated in FIGS. 4 and 6A-D, the largest colonies were consistently 2 to 3 times the size of the smallest colonies. The larger colonies were composed of small spindle-shaped cells, as shown in FIG. 6C. The smaller colonies were composed of broad, flattened cells (see FIG. 6D), and tended to be less confluent than the larger colonies.

Assays for Differentiation into Osteoblasts and Adipocytes

Figure 5:
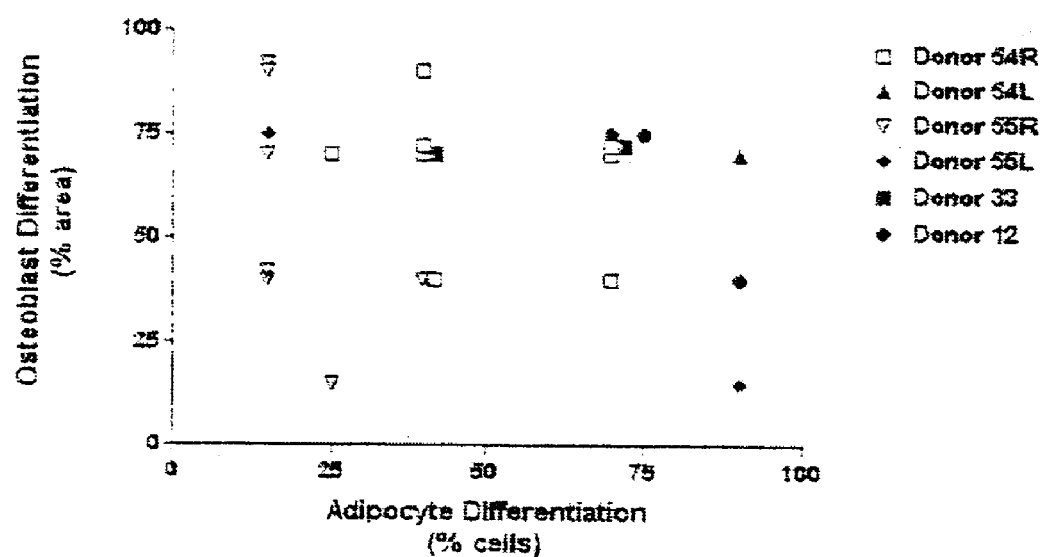
FIG. 5 is a graph depicting differentiation into osteoblasts and adipocytes of MSCs obtained from CFU assays at passage 2. R and L indicate samples from right and left iliac crest of same donor taken at the same time.

In order to assess the multipotentiality of MSCs cultured as described in this example, MSCs obtained from passage 2 were plated at low density, and individual colonies were isolated using cloning rings. Duplicate aliquots of the cells from the colonies were grown to confluence and assayed for differentiation into either osteoblasts or adipocytes. All of the clones isolated from early passage cultures differentiated into both phenotypes, as shown in FIGS. 5 and 6A-H. However, there was considerable variation in the extent of differentiation. When some colonies were sub-cultured, the plates were almost completely covered with mineral following incubation with osteogenic medium. In duplicate samples, essentially all the cells contained Oil Red-O staining vacuoles following incubation in adipogenic medium. When other colonies were sub-cultured, the cells either preferentially differentiated into one phenotype, or differentiated only poorly into either, as indicated in FIG. 5. This variation was detectable, even when large colonies isolated from the same plate from the same donor were compared.

Figure 6G:
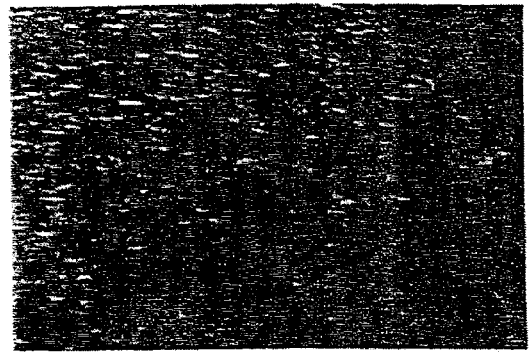
FIG. 6G is an image depicting differentiation into osteoblasts of cells obtained from passage 12 from donor 54L after the cells were grown to confluence and incubated in osteogenic medium for 18 days.
Figure 6H:
FIG. 6H is an image depicting differentiation into adipocytes of cells from a duplicate culture of cells obtained from passage 12 from donor 54L, as in FIG. 6G, after incubating the cells in adipogenic medium for 18 days.
Figure 7:
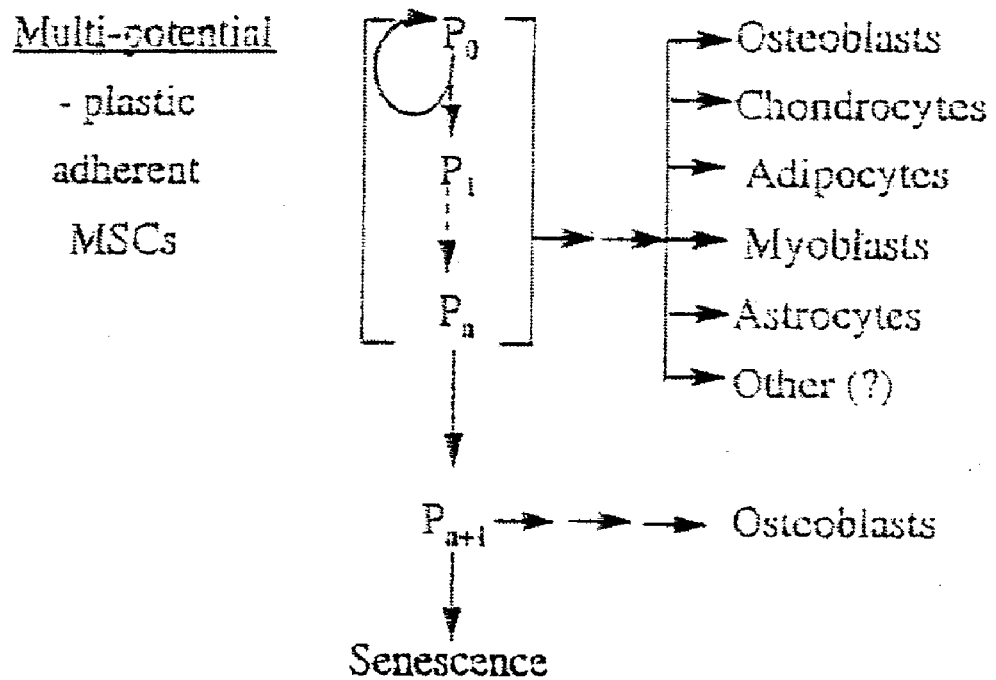
FIG. 7 is a diagram depicting loss of multipotentiality of MSCs as they are expanded in culture.

Similar differentiation assays were carried out with late passage MSCs (e.g., passage 12). Because the MSCs no longer generated colonies following sparse plating, the assays were performed in nearly confluent cultures after plating the cells at about a 1:3 dilution. MSCs of late passage cultures retained the ability to differentiate into osteoblasts, as indicated in FIG. 6G and Table 1. In fact, a few cultures spontaneously began to deposit mineral. However, the MSCs failed to differentiate into adipocytes as they lost their ability to generate CFUs, as indicated in FIG. 6H and Table 1.

TABLE 1

Differentiation of Early and Late Passage MSCs

| Donor | Passage # | CFU (%) | Adipocytes (%) | Mineralization (% area) |
|---|---|---|---|---|
| 12 | 2 | 38 | 70% | 70% |
| | 12 | 0 | 0 | 75% |
| 54L | 2 | 40 | 90% | 70% |
| | 12 | 0 | 0 | 70% |

The data in Table 1 (i.e., regarding passage 2 cells) were obtained as follows. Large colonies were isolated from a CFU assay using cloning cylinders. Duplicate aliquots of the cells were re-plated and grown to near confluence. The cultures were incubated in either adipogenic or osteogenic medium for 18 days. In experiments using passage 12 cells, the cells were grown to near confluence after plating at a 1:3 dilution, and then duplicate cultures were incubated in either adipogenic or osteogenic medium for 18 days. As depicted in FIG. 3, few, if any, CFUs were obtained using passage 12 cells from donors other than numbers 12 and 54L as disclosed herein.

MSCs isolated by virtue of their ability to adhere to plastic culture surfaces have characteristic properties that have been well-defined previously (see, e.g., Friedenstein et al., 1976, Exp. Hematol. 4:267-274; Castro-Malaspina et al., 1980, Blood 56:289-301; Mets and Verdonk, 1981, Mech. Aging. Dev. 16:81-89; Piersma et al., 1985, Exp. Hematol. 13:237-243; Friedenstein et al., 1987, Cell and Tissue Kinetics 20:263-272; Owen and Friedenstein, 1988, In: Cell and Molecular Biology of Vertebrate Hard Tissues, pp. 42-60, Ciba Foundation Symp., Chichester, UK; Caplan, 1991, J. Ortho. Res. 9:641-650; Prockop, 1997, Science 276:71-74). However, there is considerable variability in cultures prepared from different sources and under different conditions. For example, initial cultures of MSCs obtained from murine bone marrow are heavily contaminated by hematopoietic precursor cells (Clark and Keating, 1995, Ann. New York Acad. Sci. 770:70-78), and the yields of MSCs are extremely low from some inbred strains (Phinney et al., 1999, J. Cell. Biochem. 72:570-585). In contrast, hematopoietic precursor cells appear to be shed rapidly from cultures of human MSCs. However, at least two morphologically distinct cells are present (Mets and Verdonk, 1981, Mech. Aging. Dev. 16:81-89; Satomura et al., 1998, J. Cell. Physiol. 177:426-438). These two types are designated Type I cells (spindle-shaped cells which grow rapidly) and type II cells (broad, slowly growing cells). Type II cells increase in number as the cells are passed, and appear to arise from type I cells. In addition, cells with intermediate morphologies are observed.

The data disclosed in this example demonstrate that expandability in culture of human MSCs obtained from iliac crest aspirates varies significantly when the cells are initially plated at high density. This variation is not explained by the gender or the age of the donors. Also, it was not explained by the number of nucleated cells present in the sample. Instead, it can reflect a sampling variation in aspirates of marrow obtained from the iliac crest, since the variation between even two samples taken from the same volunteer at the same time was observed. MSCs arise from the complex architectural structures of perivascular cells that incompletely separate the marrow itself from capillaries (Prockop, 1997, Science 276:71-74), and the yield of MSCs can vary with the presence of such architectural structures in the aspirate.

The expandability of the MSC cultures cannot be correlated with initial growth rates in the first or second passage. However, as described in this example, expandability can be predicted on the basis of a simple assay which detected CFUs in an MSC sample. Although definitive experiments with genetic markers have not been reported, each colony in a CFU assay is assumed to arise from a single cell (Castro-Malaspina et al., 1980, Blood 56:289-301; Kuznetsov et al., 1997, J. Bone Miner. Res. 12:1335-1347; Satomura et al., 1998, J. Cell. Physiol. 177:426-438). Therefore, without wishing to be bound by any particular theory of operation, it is believed that the number of CFUs obtained from early passage cultures reflects the number of replication-competent MSCs or precursors of MSCs in a sample of marrow. In samples in which only low numbers of colony-forming MSCs can be detected, the cells may have undergone many doublings prior to reaching confluence in the first plating and, therefore, have a limited potential for further expansion.

The data disclosed in this example suggest that a simple CFU assay can be used to identify samples that are rich in type I (spindle-shaped) cells. Therefore, such an assay can be used to compare the relative expandability of MSC samples (i.e., either by comparing CFU content of the samples or by comparing the CFU content of one sample with a standard curve or other reference data correlating CFU content with expandability). A CFU assay can also be used to select samples that have the greatest potential to expand in culture from among a number of MSC samples.

Samples rich in type I cells also have greater potential for differentiation than samples which contain relatively fewer type I cells. Therefore, CFU assays in early passage MSCs can be used to identify samples that contain substantial numbers of differentiable cells, and which are therefore appropriate for extensive characterization or gene manipulation.

As recently demonstrated by Kuznetsov et al. (1997, J. Bone Miner. Res. 12:1335-1347) and Satomura (1998, J. Cell. Physiol. 177:426-438), cells of colonies obtained after sparse plating of early passage MSCs are heterogeneous in size, morphology, and potential to differentiate into osteoblasts in vivo. As disclosed in this example, clones obtained from early passage cells are also heterogeneous in their potential to differentiate into adipocytes in culture. Therefore, the cells may not be equally multipotential.

The results presented herein demonstrate that MSCs isolated by virtue of their ability to adhere to plastic culture surfaces retain the ability to differentiate into a variety of non-hematopoietic cells following a number of passages in culture. Recent reports indicate that such MSCs can differentiate into satellite cells and muscle cells following systemic infusion of the MSCs (Ferrari et al., 1998, Science 279:1456, 1528-1530) or into astrocytes following infusion into brain (Azizi et al., 1998, Proc. Natl. Acad. Sci. USA 95:3908-3913; Kopen et al., 1999, Proc. Natl. Acad. Sci. USA 96:10711-10716).

The results disclosed in this example furthermore demonstrate that as MSCs were passed in culture plated at a high initial cell density, there was could be an increasing loss of multipotentiality, the extent of the loss depending on the culture conditions used. Bruder et al. (1997, J. Cell. Biochem. 64:278-294) reported that samples of MSCs can retain their potential to differentiate into osteoblasts even after 15 passages in culture, as confirmed by the data disclosed in this example. Indeed, the data disclosed in this example demonstrate that some late passage MSCs spontaneously differentiated into osteoblasts. However, as the MSCs approached senescence in culture, they lost their ability to differentiate into adipocytes.

Example 2

Method of Isolation and Expansion of Human Marrow Stromal Cells in Culture

The data disclosed in this example demonstrate that a small sample of human bone marrow can be used as a source of stem-like cells that are progenitors of cells found in a variety of tissues, including bone, cartilage, muscle, lung, and central nervous tissue. In this example, a method of isolating and expanding human marrow stromal cells (MSCs) is described. Summarily, the method comprises removing a bone marrow sample from a donor (e.g., bone marrow obtained in an aspirate of a human iliac crest, performed under local anesthesia as an outpatient procedure). MSCs are isolated from the bone marrow, and can be cultured under conditions describe in this example in order to increase the number of cells. Using this method, very large numbers of cells can be isolated for use, for example, in a variety of cell and gene therapy applications.

The data disclosed in this example demonstrate that plating MSCs at low density (e.g., between about 0.5 to about 10 cells per square centimeter) increases, relative to prior art culture techniques, the number of population doublings which the MSCs can undergo without also undergoing differentiation. As a result, differentiable MSCs can be expanded in culture to a far greater extent than they can using prior art culture/expansion methods.

Isolation of MSCs

The procedure used to isolate MSCs was described in Example 1. Briefly, a 20 milliliter bone marrow aspirate was obtained from one or both iliac crests of human volunteers ranging from 19 to 49 years under local anesthesia. Mononuclear cells (MNCs) were isolated using a standard protocol involving centrifugation on a ficoll gradient, culturing, and removing non-adherent cells, as described in Example 1. MSCs obtained in this manner were counted using an automated instrument (Coulter) or a hematocytometer, frozen slowly in 5% DMSO and 30% FCS, and stored frozen in liquid nitrogen until use in expansion procedures.

Expansion of MSCs

The following procedures were used to expand MSCs, and are illustrated in FIG. 8, using donor 59R MSCs as an example. The cells were plated at a density of about 3 cells per square centimeter. For comparison of cells obtained from different sources (e.g., aspirates obtained from different donors and multiple aspirates obtained at the same time from the same donor), the cells were plated in 176 square centimeter culture dishes such that about 528 cells were plated per dish. The culture medium was changed, on average, every 3-4 days. The cells were harvested on days 10 and 14 after the initial plating.

The number of MSCs expanded in the first culture passage ("pass 1") increased by a factor of from 152 to about 350 in four different samples of bone marrow aspirates, as indicated in Table 2.

TABLE 2

Yields of Human MSCs

| Sample (Donor) | # nucleated cells in 20 ml aspirate | Number of MSCs Plated | Number of MSCs Recovered | Fold Increase | Total Yield of MSCs if all plated |
|---|---|---|---|---|---|
| 58R | $2.2 \times 10^7$ | All nucleated | $4.6 \times 10^5$ | | |
| 1st pass | | 528 | $8.0 \times 10^4$ | 152× | $7.0 \times 10^7$ |
| 2nd pass | | 528 | $1.1 \times 10^6$ | 2,084× | $1.5 \times 10^{11}$ |
| 3rd pass | | 528 | $2.3 \times 10^5$ | 432× | $6.5 \times 10^{13}$ |
| 58L | $1.7 \times 10^7$ | All nucleated | $6.6 \times 10^5$ | | |
| 1st pass | | 528 | $8.6 \times 10^4$ | 163× | $1.1 \times 10^9$ |
| 2nd pass | | 528 | $4.2 \times 10^4$ | 795× | $8.6 \times 10^{10}$ |
| 3rd pass | | 528 | $3.1 \times 10^5$ | 589× | $5.0 \times 10^{13}$ |
| 59R | $2.7 \times 10^7$ | All nucleated | $8.1 \times 10^5$ | | |
| 1st pass | | 528 | $1.9 \times 10^5$ | 350× | $2.8 \times 10^8$ |
| 2nd pass | | 528 | $2.4 \times 10^5$ | 455× | $1.3 \times 10^{11}$ |
| 3rd pass | | 528 | $7.5 \times 10^5$ | 1,420× | $1.8 \times 10^{14}$ |
| 59L | $1.2 \times 10^7$ | All nucleated | $9.2 \times 10^5$ | | |
| 1st pass | | 528 | $1.4 \times 10^5$ | 265× | $2.4 \times 10^8$ |
| 2nd pass | | 528 | $1.7 \times 10^5$ | 322× | $7.8 \times 10^{10}$ |
| 3rd pass | | 528 | $5.0 \times 10^5$ | 947× | $7.4 \times 10^{13}$ |
| 18 | | | | | |
| 2nd pass | | $1.8 \times 10^4$ | $6.4 \times 10^6$ | 330× | $7.8 \times 10^{10}$ |
| AVERAGE FOLD EXPANSION = | | | | 613× | $7.8 \times 10^{10}$ |

In order to expand the MSCs to a greater degree, MSCs expanded in the first culture passage were harvested using 0.25% trypsin and 1 millimolar EDTA as described in Example 1. Harvested cells were re-plated at an initial density of about 3 cells per square centimeter and re-cultured using the same conditions. MSCs expanded in number by a factor of about 322 to 2,084, relative to the number of re-cultured first pass cells, indicating that cells obtained from the first passage retained their expandability. MSCs harvested following the second culture passage were again re-cultured. In the third culture passage ("pass 3" in Table 2), the cells expanded in number by a factor of about 432 to 1,420, relative to the number of re-cultured second pass cells indicating that cells obtained from the second passage retained their expandability. If all of the MSCs obtained from the first and second passages had been plated, the final yield of cells would have been from about $5 \times 10^{13}$ to $1.8 \times 10^{14}$, depending on the source. Considering that the total number of cells in the body of an adult human is estimated to be approximately $10^{13}$ cells, this method clearly yields more than sufficient numbers of cells for numerous purposes, including therapeutic manipulations.

In addition, the MSCs from one donor (i.e., donor 18) were plated at the same density of about 3 cells per square centimeter but a higher number (i.e., about $1.8 \times 10^4$ cells) were plated at that density instead of only 528 cells. After 10 days, $6 \times 10^6$ MSCs were recovered, demonstrating that the method disclosed herein can be successfully expanded to obtain large number of multipotential stem cells.

Prior art techniques for expanding MSCs in culture teach plating the cells at a density of about 5,000 cells per square centimeter, and then growing the cells for about two weeks. This prior art methods yields only an approximately three-fold expansion of MSC cell number.

As shown in FIG. 1, the number of population doublings that can be obtained from any given sample of MSCs twice grown to confluence varies widely and ranges from about four to about seventeen population doublings. However, as the cells are passaged in culture under standard conditions, the efficiency of CFUs decreases, as indicated in FIG. 3. Furthermore, as the number of CFUs that are detectable in an MSC sample decreases (e.g., as the number of times the sample is passaged in culture), the potential of the cells to differentiate into osteoblasts or adipocytes also decreases, as indicated in FIG. 6.

Figure 9:
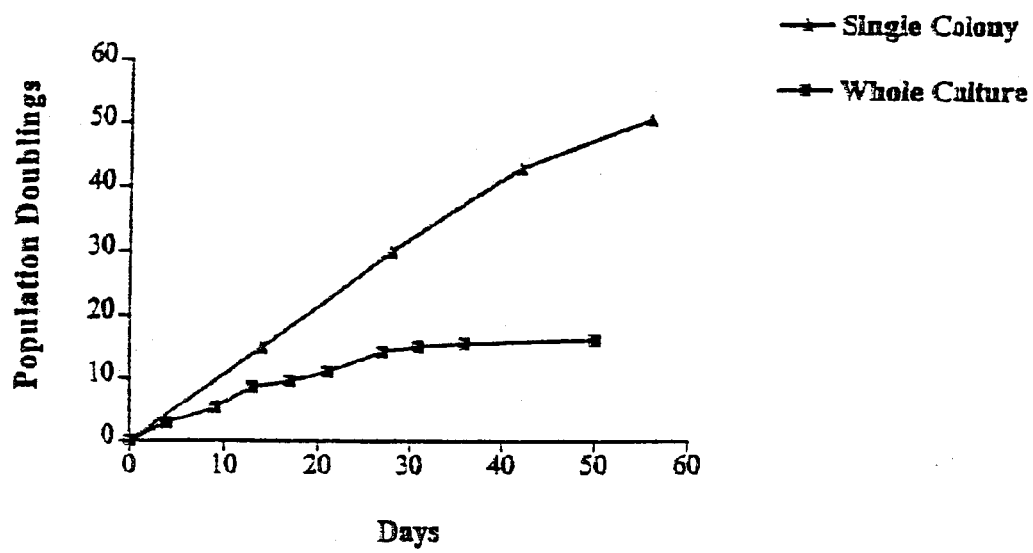
FIG. 9A is a graph depicting the expandability (in terms of population doublings) of MSCs in culture in which cells were propagated at high density ("whole culture") or at low density ("single colony"). For low density (single colony) expansion, one of the largest colonies obtained from the previous passage was isolated using a cloning ring, and the MSCs from that colony were used for plating the next passage.
FIG. 9B is a diagram which depicts how MSCs corresponding to the "single colony" MSCs in FIG. 9A were expanded.
Figure 10:
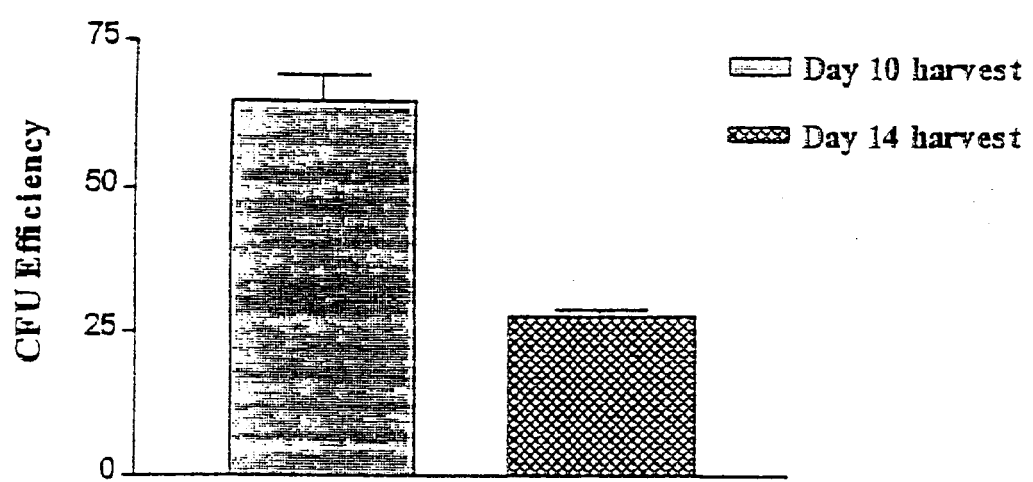
FIG. 10 is a bar graph depicting the CFU efficiency of cells obtained from early ("Day 10 harvest") and late ("Day 14 harvest") colonies. The results indicate that harvesting cells before the colonies stop expanding on day 14 may provide the best yield of early progenitor cells.

The method of culturing MSCs described in this Example permits the MSCs to be expanded in culture to a greater extent than prior art MSC expansion methods. For instance, the present invention allows the number of cells that grow from the colonies to increase by a factor of several hundred-fold during each passage, as indicated in FIG. 8. Moreover, the number of cell doublings is increased three-fold relative to prior art culture conditions, as indicated in FIG. 9. Therefore, the MSC culture/expansion method described in this example, allows a greater number of MSCs to be generated, and including a greater percentage of differentiable (i.e., multipotential) cells than do prior art culture methods. The enhanced expandability of MSCs generated using the method described in this example is evidenced by the fact that the number of CFUs detectable using the assay described in Example 1 remains high through several passages (especially if the cells are harvested after ten days, rather than after fourteen days, as indicated in FIG. 10).

Figure 11:
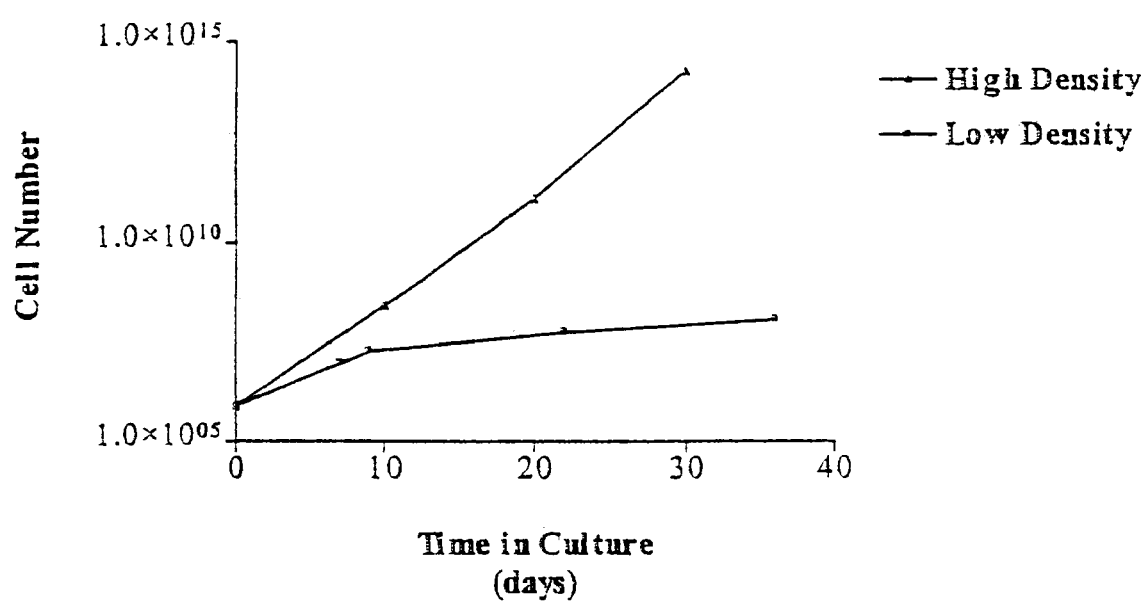
FIG. 11 is a graph depicting the expandability of MSCs isolated from a 20 milliliter bone marrow aspirate, in which cells were propagated either at high density (i.e. about 5,000 cells per square centimeter) or at low density (i.e. about 3 cells per square centimeter).

Culturing MSCs at an initially low density greatly increases the number of cells that can be obtained in a relatively short period of time, relative to culturing MSCs at an initially high density, as indicated in FIG. 11. Under appropriate conditions of low density subculture and using a sufficient quantity of growth surface and medium, up to about $10^{14}$ cells can be generated, a number that is approximately 10 times the number of cells present in the human body. However, producing such vast numbers of cells is presently impractical from a technical standpoint because of the large surface area necessary to culture the cells. It is recognized that devices having relatively large surface areas can be used including, for example, the series of intercommunicating culture flasks presently sold under the trademark Cell Factory™ (Nunc), which have surfaces areas of 6,000 to 25,000 square centimeters. Of course the form of the growth surface is not critical, and can include beads, fibers, sponges, and the like. Cell numbers as large as $10^{14}$ are not necessary for using MSCs as therapeutic agents, since much smaller numbers of cells are required for most therapeutic purposes (e.g., about $10^8$ MSCs are theoretically all that is required in neurotransplantation for treatment of Parkinson's disease). Also, the ability to extensively expand MSCs in culture makes it possible to carry out gene manipulations that are not otherwise possible. For example, endogenous genes in mammalian cells can be specifically replaced by similar exogenous genes by the mechanism of homologous recombination. However, homologous recombination requires cells that can be extensively expanded in culture and therefore subject to extensive selection for clones of cells that have undergone the rare event of homologous recombination of an exogenous gene with an endogenous gene. The present invention makes such manipulations of MSCs possible.

The effects of plating density on colony morphology are shown in FIGS. 12A-12E. Plating the cells at a density of between about 0.5 cells to about 3 cells per square centimeter allowed MSCs to grow as large colonies. At 6 cells per square centimeter, only small colonies were detected. The percentage of large colonies with respect to all colonies also decreased markedly among MSCs plated at 6 cells per square centimeter, relative to the percentage of large colonies detected among MSCs plated at lower densities. Also, the plating the MSCs at 3 cells per square centimeter, instead of at 12 cells per square centimeter, not only increases the number of large colonies detected, but also increases the total number of cells recovered from the culture dishes by about three-fold, as indicated in FIG. 13A (plated at 12 cells per square centimeter) and 13B (plated at 3 cells per square centimeter). MSCs were counted by incubating plated MSCs with crystal violet, washing the MSCs, and extracting the dye from MSCs using ethanol. Spectrophotometric assay of the ethanol dye extract indicated that the number of cells obtained by plating the cells at 3 cells per square centimeter was about three times the number of cells obtained by plating the cells at 12 cells per square centimeter (i.e., the optical density of the dye extract at 580 nanometers ($OD_{580\ nm}$) was 12.2 and 4.2 for cells plated at 3 and 12 cells per square centimeter, respectively). Therefore, plating MSCs at the lower density allows a greater total number of cells to be obtained. MSCs plated at the lower density also exhibit a greater CFU efficiency.

Example 3

MSCs Cultured at a Low Initial Cell Density Produce One or More Growth Factors

The data disclosed herein, for example in FIG. 12, disclose that the rate at which the MSCs grow after sparse plating (i.e., from about 0.5 to about 3 cells per square centimeter) is greatly influenced by at least one component which the MSCs secrete into the culture medium. In FIGS. 12A-12E, MSCs were plated at selected initial cell densities of 0.5-6 cells per square centimeter. The plates were incubated with complete medium for 12 days, and then washed using PBS. The cells on the plates were stained for 10 minutes with Crystal Violet and methanol in order to visualize colonies.

Figure 12A:
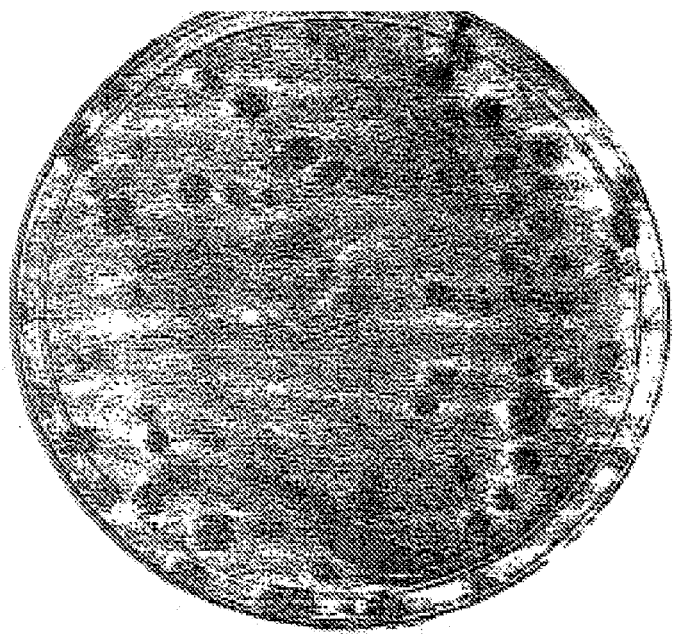
FIGS. 12A-12F is a series of image depicting culture plates on which MSCs (FIGS. 12A-12D) or fibroblasts (FIG. 12E) were cultured at selected cell densities, and a bar graph (FIG. 12F) which summarizes the presence of large colonies on the plates shown in FIGS. 12A-12C following 12 days of incubation. Initial cell densities at which the cells were plated were 3.0 (FIGS. 12A and 12E), 1.5 (FIG. 12B), 0.5 (FIG. 12C), and 6.0 (FIG. 12D) cells per square centimeter. Colony formation was not observed for the fibroblasts plated in FIG. 12E.
Figure 12B:
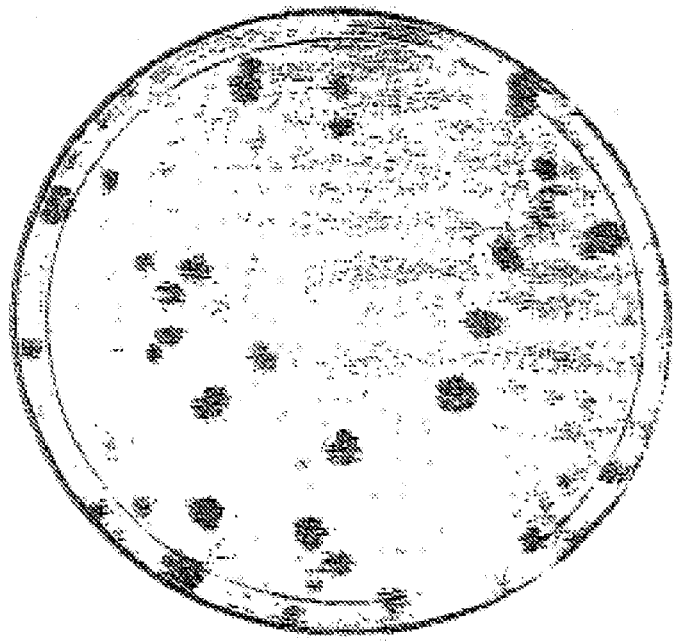
Figure 12C:
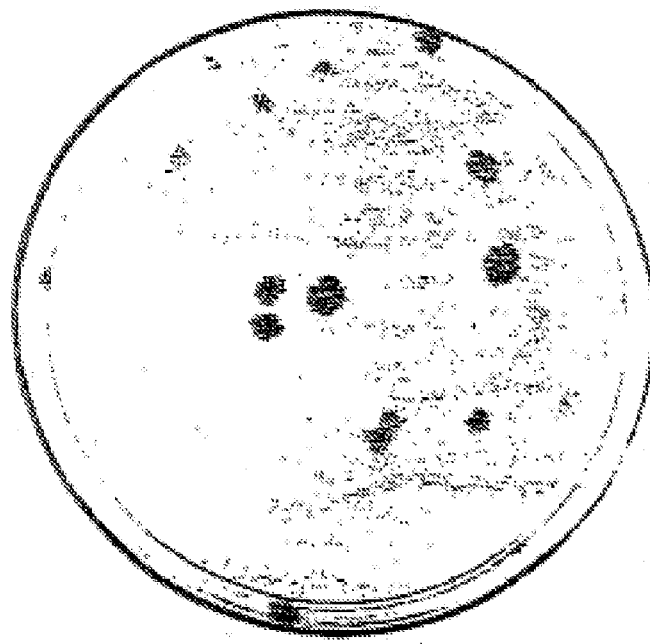
Figure 12D:
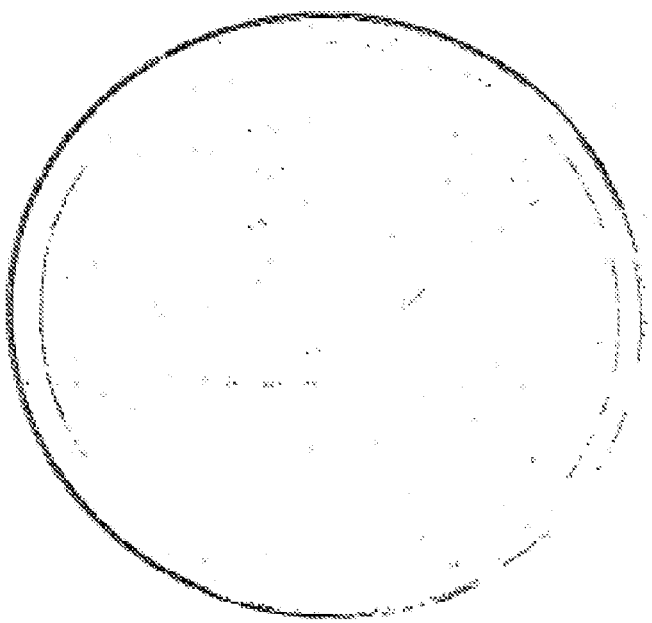
Figure 12E:
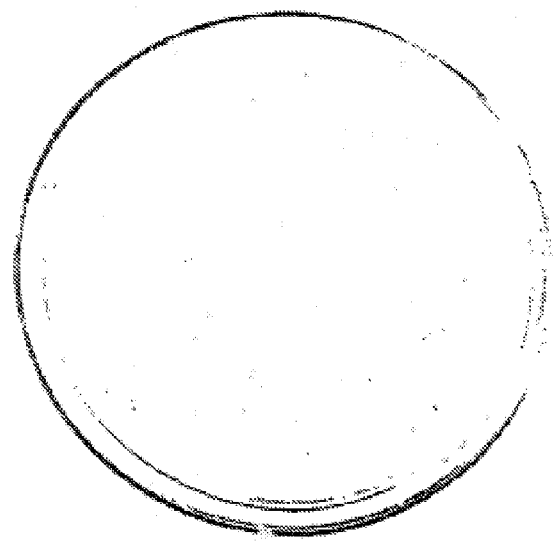
Figure 12F:
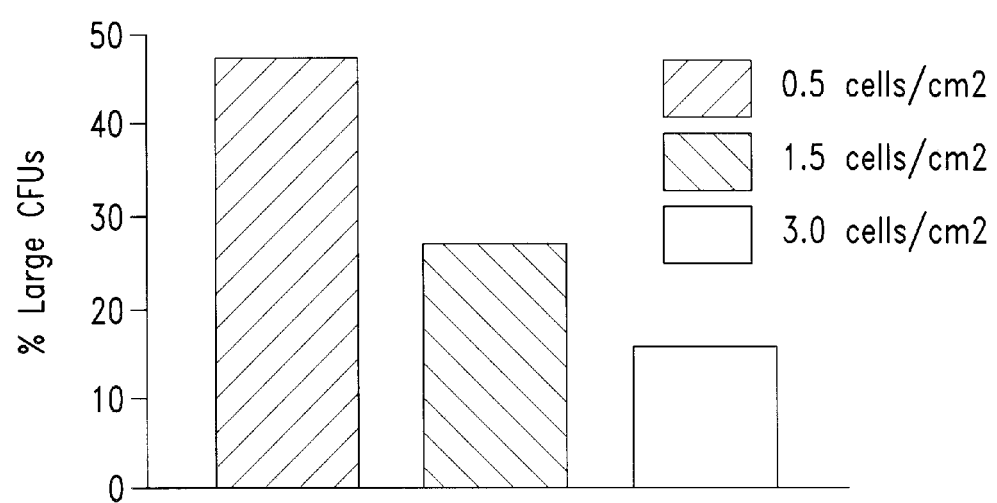
Figure 13A:
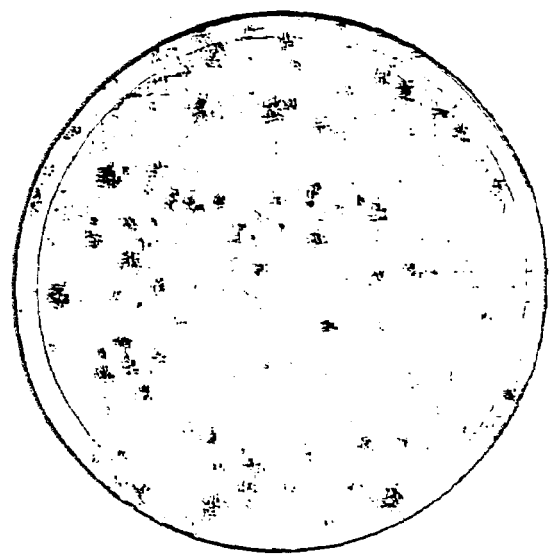
FIGS. 13A and 13B, is a pair of images of culture plates, depicting the effect of plating MSCs at an initial density of 12 (FIG. 13A) or 3 (FIG. 13B) cells per square centimeter on formation of large colonies and on cell numbers upon incubating the cells on growth medium.
Figure 13B:
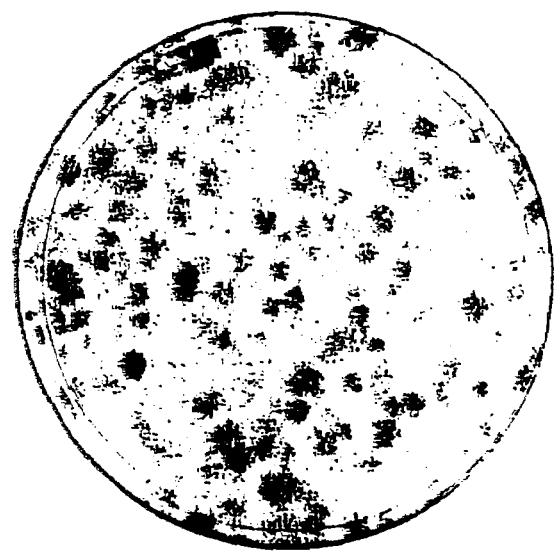

As indicated in FIGS. 12A-12C, MSCs plated at an initial density of 0.5-3 cells per square centimeter gave rise to numerous easily visualized colonies. When MSCs were plated at an initial cell density of 6 cells per square centimeter (i.e. as in FIG. 12D), MSC colonies were small (i.e. about 10-100 cells) and could not be easily visualized. MSCs isolated from colonies plated at an initial cell density of 6 cells per square centimeter could not be further expanded. In addition, as indicated in FIG. 12F, colony size was correlated with the initial cell plating density, the lowest density yielding the largest (in diameter) colonies. Without being bound by any particular theory of operation, it may be that one or more growth factors secreted by MSCs are mitogenic at low concentration, but can inhibit colony growth at greater concentration. Thus, it may be possible to induce expansion of MSCs in culture by diluting one or more of these growth factors during incubation.

It was observed that MSCs generated by expansion of MSCs plated at initial cell density of 3 cells per square centimeter or lower represent a sub-population of MSCs that are small and granular. This population of MSCs is absent in high density (e.g. 30% confluent) cultures of MSCs, and is significantly reduced among MSCs generated by expansion of MSCs plated at initial cell density of 6 cells per square centimeter or greater. This observation has been confirmed by fluorescence-assisted cell separation (FACS) analysis. In addition, it has been observed that tritiated thymidine uptake is inhibited in MSCs plated at an initial cell density of 6 cells per square centimeter or greater.

Two samples of MSCs were plated in a cell factory having a growth surface of about 6,000 square centimeters, one at an initial density of about 12 cells per square centimeter, and the other at an initial density of about 50 cells per square centimeter, and the cells of these two samples were allowed to expand in culture for seven days in the presence of 1 liter of complete medium containing 20% (v/v) FCS. Following the seventh day, the culture medium was removed from the cells, and the cells were rinsed extensively using phosphate-buffered saline to remove residual FCS and medium. The cells were grown for an additional 24 hours in serum-free Minimal Essential medium-alpha. This medium (hereinafter referred to as "conditioned medium") was harvested from the two samples, stored as separate aliquots at −20° C., and used in subsequent experiments.

Figure 14:
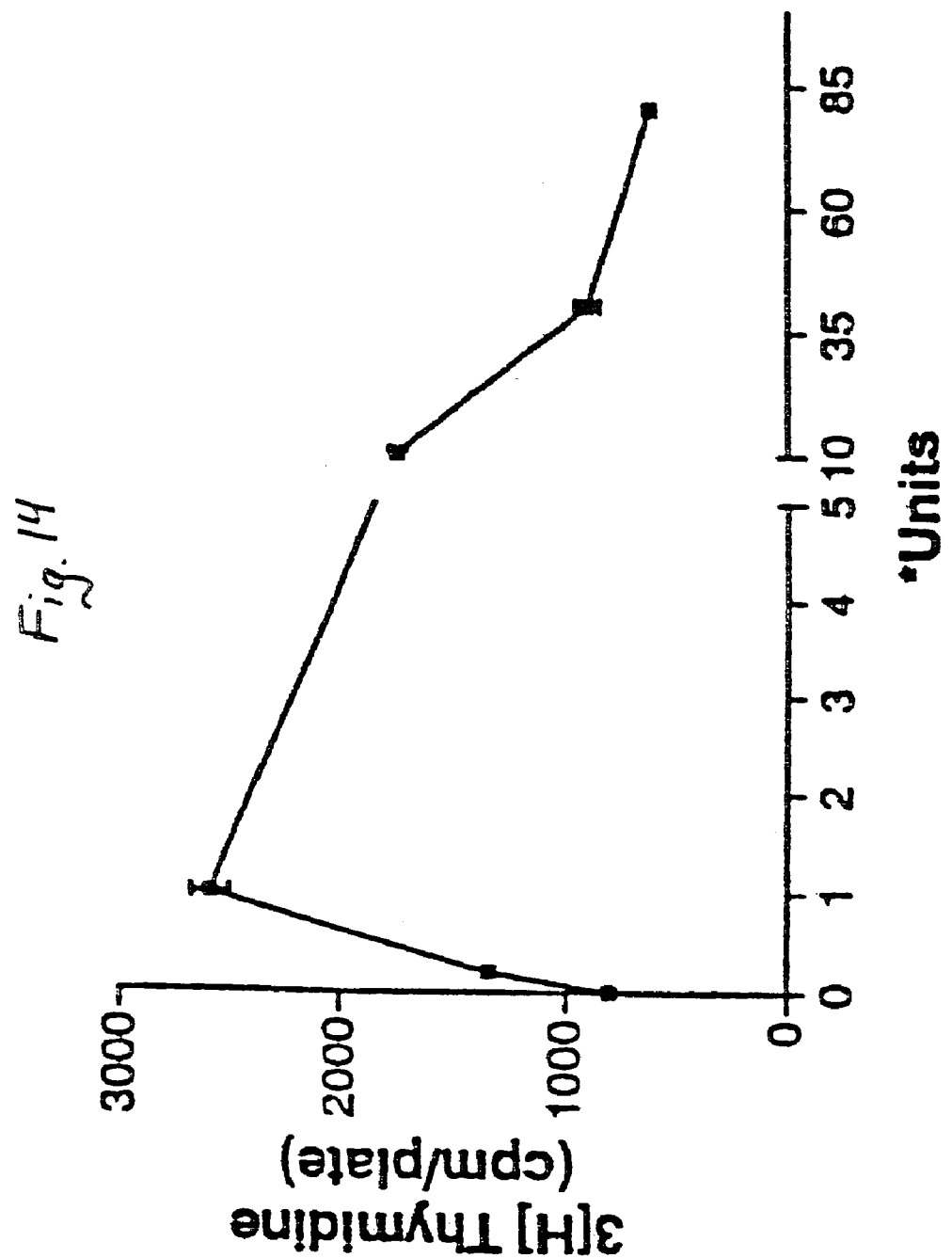
FIG. 14 is a graph depicting the effect of conditioned medium on the growth rate of MSCs, as assessed by incorporation of tritiated thymidine. Conditioned medium was obtained from cultures of MSCs, as described herein, and added to growth medium of MSCs plated at an initial cell density of about 3 cells per square centimeter, and rate of tritiated thymidine uptake was assessed. The results demonstrate that the conditioned medium exerts a bi-phasic effect on expansion of MSCs.

Conditioned medium from each of the two samples mediated a bi-phasic effect on growth of MSCs which had been plated at an initial cell density of 3 cells per square centimeter and which were incubated in the presence of 10 milliliters of complete medium supplemented with a selected amount of conditioned medium. One unit of conditioned medium was defined to be equal to 0.1 milliliter of conditioned medium. As indicated in FIG. 14, addition of 1 unit of conditioned medium to 10 milliliters of complete medium resulted in about a 3-fold increase in tritiated thymidine incorporation into MSCs. Because tritiated thymidine is primarily incorporated into newly-synthesized DNA, incorporation of tritiated thymidine during the 24 hour period directly reflects the rate at which MSCs were replicating in the culture. Addition of a greater amount of conditioned medium decreased the replication rate of the MSCs. Thus, one or more of the growth factors contained in the conditioned medium had a bi-phasic effect on growth of human MSCs.

Figure 16:
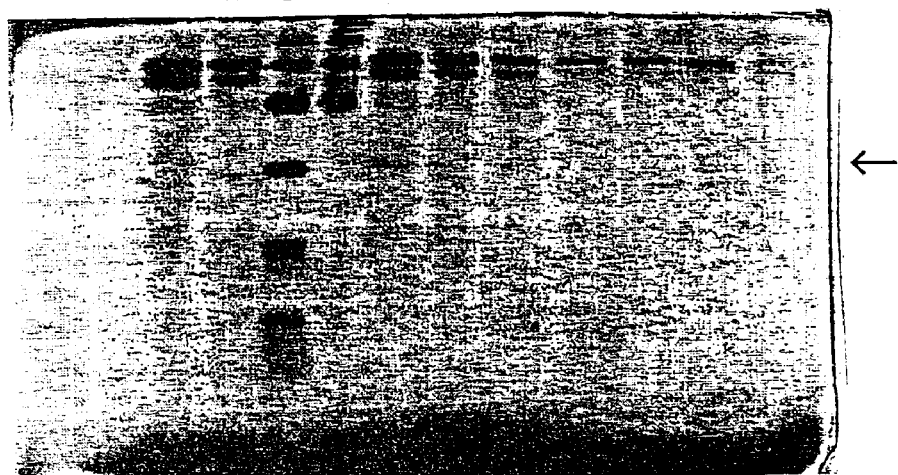
FIG. 16 is an image of the results of an SDS-PAGE separation of chromatographic fractions (lanes 2, 5, and 6) which contain a factor which enhances the growth rate of MSCs. Lanes 3 and 4 contain molecular weight markers. The arrow on the right of the image indicates the position corresponding to a weight of about 30,000.

As shown in FIG. 16, fractions from a chromatography column that exhibit the growth factor activity (i.e. lanes 2, 5, and 6 in FIG. 16) each contain a protein which exhibits a weight of about 30,000 when applied to an SDS-PAGE gel.

Without wishing to be bound by any particular theory of operation, it may be that a growth factor secreted by MSCs stimulates MSC proliferation at low concentrations, but inhibits proliferation at higher concentrations, possibly owing to down-regulation of the receptor for one or more of the factors at high factor concentrations, or to the presence of multiple factors in the conditioned medium.

To further characterize the growth factor present in the conditioned media, MSCs were cultured for 5 days at an initial cell density of 60 cells per square centimeter in medium containing Minimal Essential medium-alpha supplemented with FCS, as described above. After 5 days, this medium was removed from the cultured cells, and the MSCs were cultured for an additional 24 hours in the presence of serum-free medium to yield conditioned medium. This conditioned medium was fractionated by HPLC size exclusion chromatography.

Figure 15:
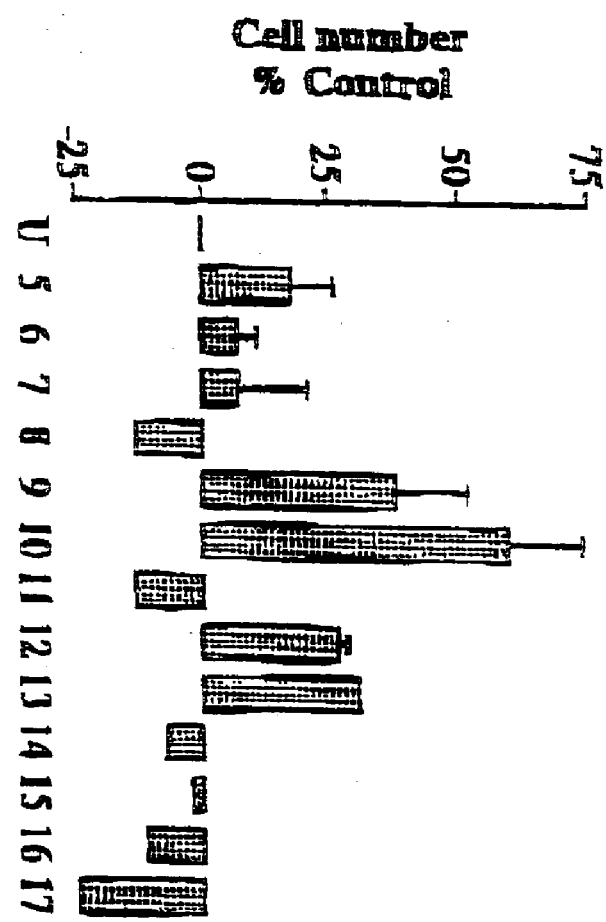
FIG. 15 is a bar graph depicting the relative effect of HPLC-fractionated (using a size exclusion chromatographic medium) human MSC conditioned media on MSCs plated at an initial density of 1.5 cells per square centimeter. The number beneath each bar indicates the HPLC fraction number. The approximate molecular weight corresponding to fraction 10 is 30,000. The approximate molecular weight corresponding to fraction 17 is 10,000.

Selected HPLC fractions were assessed for their ability to stimulate proliferation of MSCs on a test plate in which the cells were plated at an initial density of 1.5 cells per square centimeter. After 5 days, selected HPLC column fractions were added to the cultures, and the number of cells recovered 24 hours later was assessed. Fraction number 10 (containing molecules having an average molecular weight of about 30,000) greatest proliferation-stimulating activity. Fraction number 17 (containing molecules having an average molecular weight of about 10,000) inhibited growth of cells. The activities corresponding to various HPLC fractions are indicated in FIG. 15.

Without wishing to be bound by any particular theory of operation, it is believed that as MSCs grow in culture, they secrete one or more growth factors into the growth medium. At least one of these factors stimulates nearby MSCs to grow more rapidly. A stimulatory factor secreted in the medium has a molecular weight of about 30,000 Daltons.

Example 4

Rapid Expansion of Recycling Stem Cells in Cultures of Plastic-Adherent Cells from Human Bone Marrow Cultures of plastic-adherent cells obtained from bone marrow have attracted interest because of their ability to support growth of hematopoietic stem cells, their multipotentiality for differentiation, and their possible use for cell and gene therapy. In the experiments presented in this example, it was demonstrated that the cells grew most rapidly when they were initially plated at low densities (1.5 or 3.0 cells/cm$^2$) so as to generate single-cell derived colonies. The cultures displayed a lag phase of 5 days, a log phase of rapid growth of about 5 days, and then a stationary phase. FACS analysis demonstrated that stationary cultures contained a major population of large and moderately granular cells (mMSCs) and a minor population of small and agranular cells (RS-1 cells). During the lag phase, the RS-1 cells gave rise to a new population of small and densely granular cells (RS-2 cells). During the late log phase, the RS-2 cells decreased in number and regenerated the pool of RS-1 cells found in stationary cultures. In repeated passages in which the cells were plated at low density, the cells can be amplified about $10^9$-fold in 6 weeks. The cells retained their ability to generate single-cell derived colonies and, therefore, apparently retained their multipotentiality for differentiation.

In addition to stem cells for hematopoietic cells, bone marrow contains stem-like cells that are precursors of non-hematopoietic tissues (Friedenstein et al., 1976, Exper. Hematol. 4:267-274; Castro-Malaspina et al., 1980, Blood 56:289-301; Mets et al., 1981, Mech. Ageing. Dev. 16:81-89; Piersma et al., 1985, Exper. Hematol. 13:237-243; Howlett et al., 1986, Clin. Orthoped. Rel. Res. 213:251-263; Friedenstein et al., 1987, Cell & Tiss. Kinetics 20:263-272; Owen et al., 1988, In: Cell and Molecular Biology of Vertebrate Hard Tissues, Ciba Foundation Symp, Chichester, UK, pp. 42-60; Caplan, 1991, J. Orthoped. Res. 9:641-650; Prockop, 1997, Science 276:71-74). The precursors of non-hematopoietic tissues were initially referred to as plastic-adherent cells or colony-forming-units fibroblasts (Friedenstein et al., 1976, Exper. Hematol. 4:267-274; Howlett et al., 1986, Clin. Orthoped. Rel. Res. 213:251-263; Owen et al., 1988, In: Cell and Molecular Biology of Vertebrate Hard Tissues, Ciba Foundation Symp, Chichester, UK, pp. 42-60), and subsequently as either mesenchymal stem cells (Caplan, 1991, J. Orthoped. Res. 9:641-650) or marrow stromal cells (MSCs). The cells have attracted interest because of their ability to serve as a feeder layer for the growth of hematopoietic stem cells, their multi-potentiality for differentiation, and their possible use for both cell and gene therapy (see Caplan, 1991, J. Orthoped. Res. 9:641-650; Prockop, 1997, Science 276:71-74; Chiang, et al., 1999, Hum. Gene Ther. 10:61-76; Horwitz et al., 1999, Nature Med. 5:309-3138-11).

Friedenstein et al. (Friedenstein et al., 1976, Exper. Hematol. 4:267-274) initially isolated MSCs by their adherence to tissue culture surfaces and essentially the same protocol was used by many subsequent investigators (see Castro-Malaspina et al., 1980, Blood 56:289-301; Mets et al., 1981, Mech. Ageing. Dev. 16:81-89; Piersma et al., 1985, Exper. Hematol. 13:237-243; Howlett et al., 1986, Clin. Orthoped. Rel. Res. 213:251-263; Owen et al., 1988, In: Cell and Molecular Biology of Vertebrate Hard Tissues, Ciba Foundation Symp, Chichester, UK, pp. 42-60; Caplan, 1991, J. Orthoped. Res. 9:641-650; Anklesaria et al., 1987, Exper. Hematol. 15:636-644; Beresford et al., 1992, J. Cell Sci. 102:341-351; Cheng et al., 1994, Endocrinol. 134:277-286; Clark et al., 1995, Ann. N.Y. Acad. Sci. 770:70-78; Kuznetsov et al., 1997, Br. J. Haematol. 97:561-570; Kuznetsov et al., 1997, J. Bone Min. Res. 12:1335-1347; Bruder et al., 1997, J. Cell. Biochem. 64:278-294; Wakitani et al., 1995, Muscle Nerve 18: 1417-1426). The isolated cells were shown to be multipotential in that they differentiate in culture or after implantation in vivo into osteoblasts, chondrocytes, adipocytes, and myotubes. After systemic infusion of MSCs, progeny of the cells appeared in a variety of tissues, including bone (Pereira et al., 1995, Proc. Natl. Acad. Sci. USA 92:4857-4861; Pereira et al., 1998, Proc. Natl. Acad. Sci. USA 95:1142-1147; Hou et al., 1999, Proc. Natl. Acad. Sci. USA 96:7294-7299; Nilsson et al., 1997, Blood 89:4013-4020), cartilage (Pereira et al., 1995, Proc. Natl. Acad. Sci. USA 92:4857-4861; Pereira et al., 1998, Proc. Natl. Acad. Sci. USA 95:1142-1147), lung (Pereira et al., 1995, Proc. Natl. Acad. Sci. USA 92:4857-4861; Pereira et al., 1998, Proc. Natl. Acad. Sci. USA 95:1142-1147; Keating et al., 1996, Exper. Hematol. 24:1056, Abs. 180), spleen (Keating et al., 1996, Exper. Hematol. 24:1056, Abs. 180), and thymus (Keating et al., 1996, Exper. Hematol. 24:1056, Abs. 180). Also, engraftment of donor MSCs into repairing muscle was observed after either local injection or systemic injection (Ferrari et al., 1998, Science 279, 1456: 1528-1530). Engraftment into muscle of a dystrophin-deficient mouse was seen after systemic infusion of rare marrow cells defined as a "side population" or SP cells that may be precursors of MSCs (Goodell et al., 1997, Nat. Med. 12:1337-1345; Gussoni et al., 1999, Nature 401:390-393).

In addition, MSCs or related cells were shown to engraft into the central nervous system. The presence of donor derived astrocytes was observed after infusion of whole marrow into immuno-deficient mice (Eglitis et al., 1997, Proc. Natl. Acad. Sci. USA 94:4080-4085). After direct infusion into basal ganglia of rats, either rat or human MSCs integrated and migrated in a manner similar to paraventricular astrocytes that have many of the properties of marrow stem cells (Azizi et al., 1998, Proc. Natl. Acad. Sci. USA 95:3908-3913). After mouse MSCs were infused into the paraventricular region of newborn mice, some of the cells differentiated into astrocytes (Kopen et al., 1999, Proc. Natl. Acad. Sci. USA 96:10711-10716). Others appeared in large numbers in neuron-rich regions and probably differentiated into neurons (Kopen et al., 1999, Proc. Natl. Acad. Sci. USA 96:10711-10716). The potential for inter-convertibility of cells between bone marrow and the central nervous system was also emphasized by the observation (Bjornson et al., 1999, Science 283:534-537) that neural stem cells can reconstitute the hematopoietic system in mice that have undergone marrow ablation.

In spite of the great interest in MSCs, there is still no well-defined protocol for isolation and expansion of the cells in culture. Most experiments have been carried out with cultures of MSCs that are isolated primarily by their tight adherence to tissue culture dishes as described by Friedenstein et al. (Friedenstein et al., 1976, Exper. Hematol. 4:267-274; Friedenstein et al., 1987, Cell & Tiss. Kinetics 20:263-272). Several groups of investigators developed protocols to prepare more homogeneous populations (Long et al., 1995, J. Clin. Invest. 95:881-887; Simmons et al., 1991, Blood 78:55-62; Waller et al., 1995, Blood 85:2422-2435; Rickard et al., 1996, J. Bone Miner. Res. 11:312-324; Gronthos et al., 1996, J. Hematother. 5:15-23; Joyner et al., 1997, Bone 21:1-6; Stewart et al., 1999, J. Bone Miner. Res. 14:1345-1256), but none of these protocols has gained wide acceptance.

In the experiments presented in this example, a subpopulation of cells in cultures of MSCs is identified comprising MSCs that are small, proliferate rapidly, undergo cyclical renewal when the cells are re-plated, and are precursors of more mature cells in the same cultures. These cells are referred to herein as recycling stem cells (RS cells). In addition, conditions under which RS cells can be amplified about $10^9$-fold in six weeks are defined in this example.

The materials and methods used in the experiments presented in this example are now described.

Isolation and Culture of hMSCs

Human MSCs were obtained from 20 milliliter aspirates obtained from the iliac crest of normal donors ranging in age from 19 to 49 years, as described (DiGirolamo et al., 1999, Br. J. Haematol. 107:275-281). With several donors, duplicate samples were obtained on the same occasion from the right and left iliac crest. Each 20 milliliters of aspirate was diluted 1:1 with Hank's balanced salt (HBS; Gibco), and layered over about 10 milliliters of ficoll (Ficoll-Paque; Pharmacia). After centrifugation at 2500×g for 30 minutes, the mononuclear cell layer was removed from the interface and suspended in Hank's balanced salt. Cells were centrifuged at 1500×g for 15 minutes and re-suspended in complete medium (Minimum Essential Medium; alpha medium without deoxyribonucleotides or ribonucleotides, Gibco); 20% fetal calf serum lot-selected for rapid growth of MSCs (FCS, Atlanta Biologicals); 100 units per milliliter penicillin (Gibco), 100 micrograms per milliliter streptomycin (Gibco); and 2 millimolar L-glutamine (Gibco). All the cells were plated in about 25 milliliters of medium in a 176-square centimeter culture dish (Nunc) and incubated at 37° C. with 5% humidified $CO_2$. After 24 hours, non-adherent cells were discarded and the adherent cells were thoroughly washed twice with PBS. Fresh complete medium was added and replaced every three or four days for about 14 days.

The cells were harvested with 0.25% trypsin and 1 millimolar EDTA (Gibco) for 5 minutes at 37° C., re-plated in a 79-square centimeter plate, again cultured for about 14 days, and harvested. About 8 milliliters of complete medium was mixed with the trypsinized cells to inactivate the trypsin, and the cells were counted with an automated instrument (Coulter) or a hemacytometer. The cells were recovered by centrifugation and suspended at a concentration of 1–2×10$^6$ cells per milliliter in 5% DMSO and 30% FCS. Aliquots of about 1 milliliter each were slowly frozen, and stored in liquid nitrogen. One or two aliquots of each frozen stock was assayed (DiGirolamo et al., 1999, Br. J. Haematol. 107:275-281) for colony-forming-units (CFUs). The values for CFUs per 100 cells ranged from 12 to 42. To grow cultures at varying cell densities, a frozen stock of MSCs was thawed at 37° C., diluted with complete medium, and recovered by centrifugation to remove the DMSO. The cells were suspended in medium and plated at about 5,000 cells per square centimeter. After incubation for about 1 day, non-adherent cells were removed, the adherent cells were harvested with EDTA/trypsin, dissociated by passage through a narrowed Pasteur pipette, counted, and re-plated at the densities indicated in 10 milliliters of medium on 79-square centimeter plates.

FACS Analysis

Cultured MSCs were detached with EDTA/trypsin, suspended in 0.5 milliliters PBS at concentrations of 20,000 to 100,000 cells per milliliter, and assayed in a flow cytometer (FACsort; Becton Dickinson). To identify surface epitopes, large samples were prepared by plating about 18,000 MSCs at a density of 3 cells per square centimeter in 1 liter of medium in an interconnecting system of tissue culture flasks (6,000 square centimeters; Cell Factory, Nunc). The cells were cultured for 6 days and then harvested with EDTA/trypsin. The cells were washed by centrifugation in PBS and re-suspended in PBS at a concentration of about 100,000 cells per milliliter. The cells were fixed in 1% methanol or acetone at 4° C. for 10 minutes and washed with PBS. Non-specific antigens were blocked by incubating the cells at room temperature for 1 hour in 1% bovine serum albumin, 0.1% FCS, and 0.1% goat serum. The cells were washed by centrifugation in 3 volumes of PBS, and the cell pellet was suspended in 0.5 milliliters of a primary antibody solution containing 20 micrograms per milliliter of antibody, 1% bovine serum albumin and 0.1% goat serum. After incubation for 40 minutes at 4° C., the cells were washed in PBS. The primary antibodies were mouse anti-human and obtained from the following sources: CD90 (Chemicon); CD117 (Chemicon); CD11b (FITC-labeled; Chemicon); CD38 (Chemicon); Stro-1 (IgM Hybridoma Bank at the University of Iowa); CD45 (Pharmingen); CD31 (Biomeda); CD34 (Santa Cruz), and CD43. For an isotype control, nonspecific mouse immunoglobulin (DAKO) was substituted for the primary antibody. For antibodies that required a second antibody for detection, the cell pellet was incubated under the same conditions for 20 minutes with anti-mouse IgG labeled with FITC (Santa Cruz). The cells were then washed in PBS and suspended in 1 milliliter of PBS for FACS analysis.

The results of the experiments presented in this example are now described.

Effect of Plating Density on Expansion of MSCs

Figure 18A:
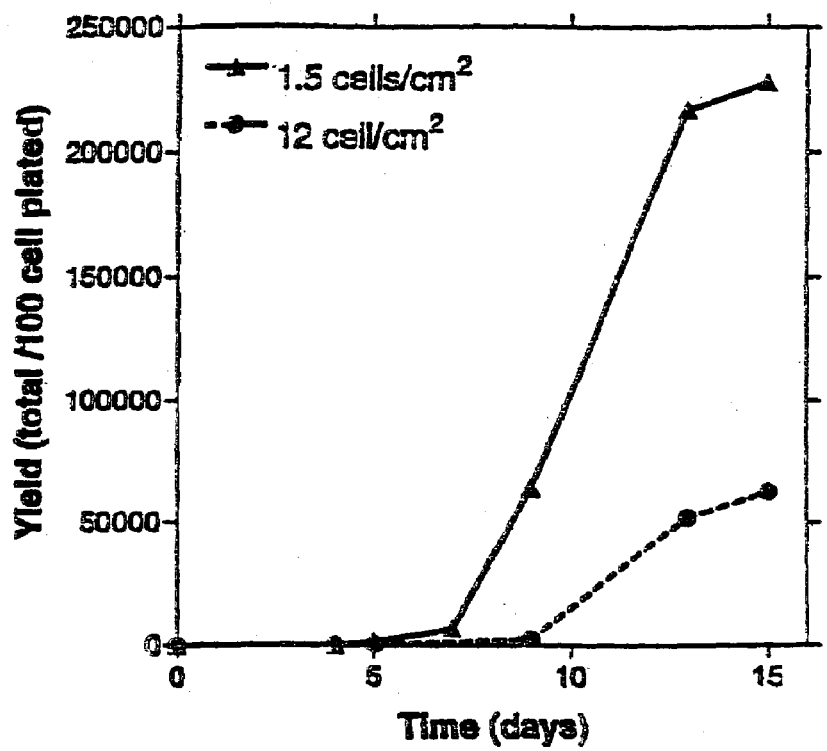
FIGS. 18A and 18B, is a pair of graphs which indicate the effect of plating density on yield of cells (FIG. 18A) and average doubling time (FIG. 18B). The cells were plated onto 79 square centimeter plates, and yield of cells was determined on the days indicated using a hemocytometer. The graph in FIG. 18A indicates the yield of cells per 100 cells plated, where cells were plated at an initial plating density of 1.5 (solid line) or 12.0 (broken line) cells per square centimeter. The graph in FIG. 18B indicates the average number of cell doublings per day when MSCs were plated at 1.5 (solid line) and 12.0 (broken line) cells per square centimeter. Values are 3-day averages from data presented in FIG. 18A.
Figure 18B:
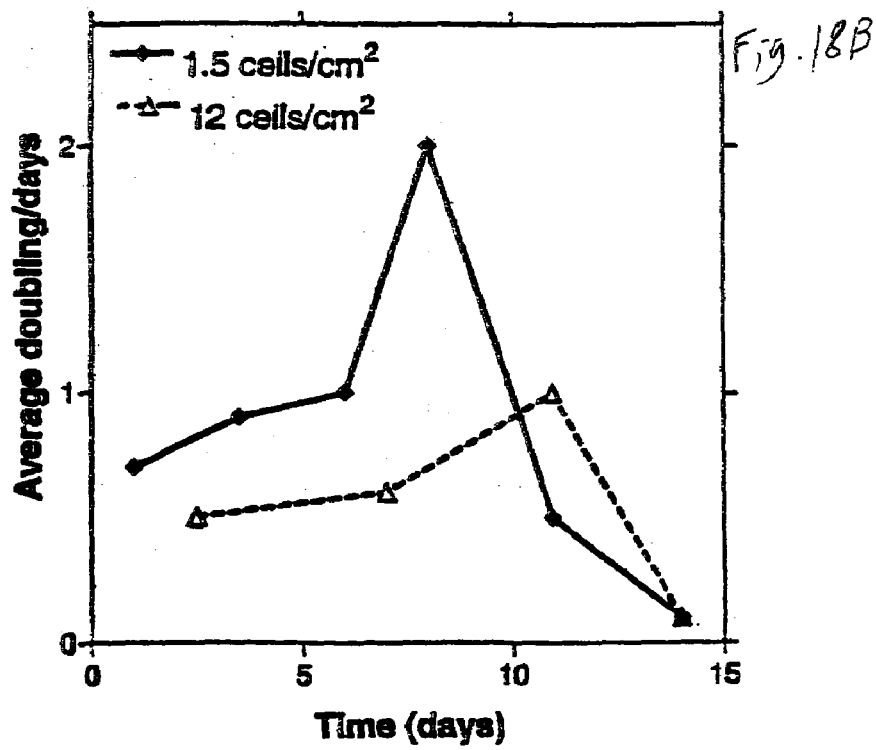

As noted (see, e.g., Example 3), human MSCs form single-cell derived colonies when plated at low density for CFUs. In the experiments presented in this example, it was observed that the number of colonies formed per 100 cells plated remained constant when we varied the density of plating from 0.5 to 12 cells per square centimeter. However, it was observed that the size of the colonies decreased markedly when the cells were plated at the higher densities. Colonies of maximal size were obtained when cells were plated at 1.5 or 3.0 cells per square centimeter with MSCs from most stock samples of bone marrow aspirates, as shown in FIG. 17. The colonies were smaller when plated at 6 or 12 cells per square centimeter. The colony size was not affected by exchanging the medium every other day or after 10 days. However, the yield of cells decreased as the size of the colonies decreased. When cells were plated at a low density of 1.5 or 3.0 cells per square centimeter, the cells expanded up to 2,000-fold over about 10 days, as indicated in FIG. 18A. In contrast, cells plated at 12 cells per square centimeter expanded only about 60-fold. When plated at low density, the cells typically exhibited three phases of growth: A lag phase, a log phase of rapid growth, and then a stationary phase (see FIG. 18A). During the log phase, the cells plated at low density doubled an average of about twice per 24 hours, i.e. doubling times of about 12 hours, as indicated in FIG. 18B. When cells were plated at 6 cells per square centimeter instead of 1.5 cells per square centimeter, the most rapid growth was at day 6 instead of day 8. If cells were plated at 12 cells per square centimeter, the doubling time was reduced to about 24 hours throughout the culture period, as indicated in FIG. 18B.

Identification of a Sub-Population of Progenitors

Cells obtained from stationary cultures of MSCs were assayed for size and granularity by forward light and side light scattering by FACS. Two populations of cells could be detected in stationary cultures, as indicated in FIG. 19A. Most of the cells were large and had a medium content of granules. However, there was a minor population of small and agranular cells. Staining with propidium iodide demonstrated that about 98% of the cells in both populations were viable. Staining with the cell-cycle specific antigen Ki-67 indicated that the small, agranular cells were not in cell cycle, whereas the larger cells were in cell cycle. A similar pattern of large and small cells was observed with cultures plated at 12 cells per square centimeter and examined after 5 days. However, a different pattern was seen with cultures that were plated at 1.5 or 3.0 cells per square centimeter and examined at 5 days. About 13% of these cells were small and agranular cells, but a new sub-population of small and granular cells accounted for about 30% of the total population, as indicated in FIG. 19B. Staining with Ki-67 demonstrated that the small and granular cells were in cell cycle. For convenience, we here refer to the small and agranular cells as recycling stem cells-1 (RS-1), the small and granular cells as recycling stem cells-2 (RS-2), and the large and moderately granular cells as mature MSCs (mMSCs).

Figure 20:
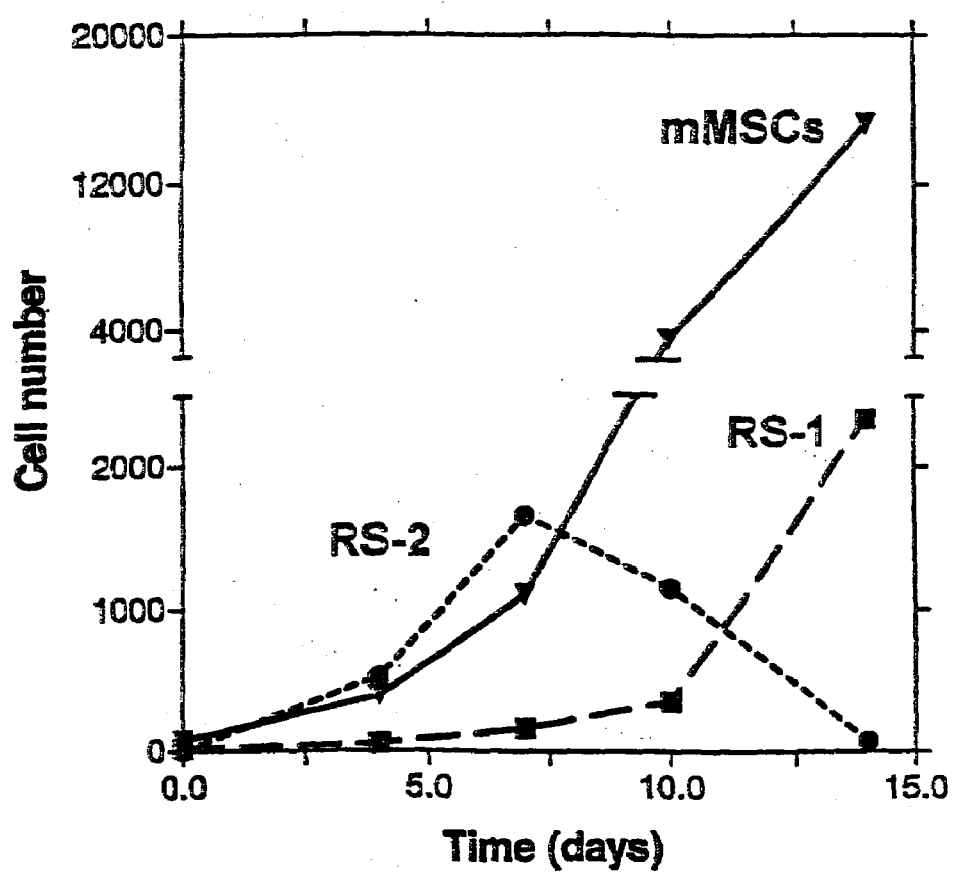
FIG. 20 is a graph which indicates the temporal dependence of the number of cells observed after initial plating of cells at 1.5 cells per square centimeter. Values are taken from the data presented in FIG. 19, adjusted for the total number of cells in the cultures.

Graphing of the data from the experiment for which results are presented in FIG. 19 indicated that RS-2 cells first appeared and expanded during the lag period, as indicated in FIG. 20. During the log phase of growth, the RS-2 cells decreased in number and the mMSCs rapidly expanded. During the late log phase, the RS-2 cells disappeared and the RS-1 cells expanded.

Correlation Between RS Cells and CFUs

Figure 21:
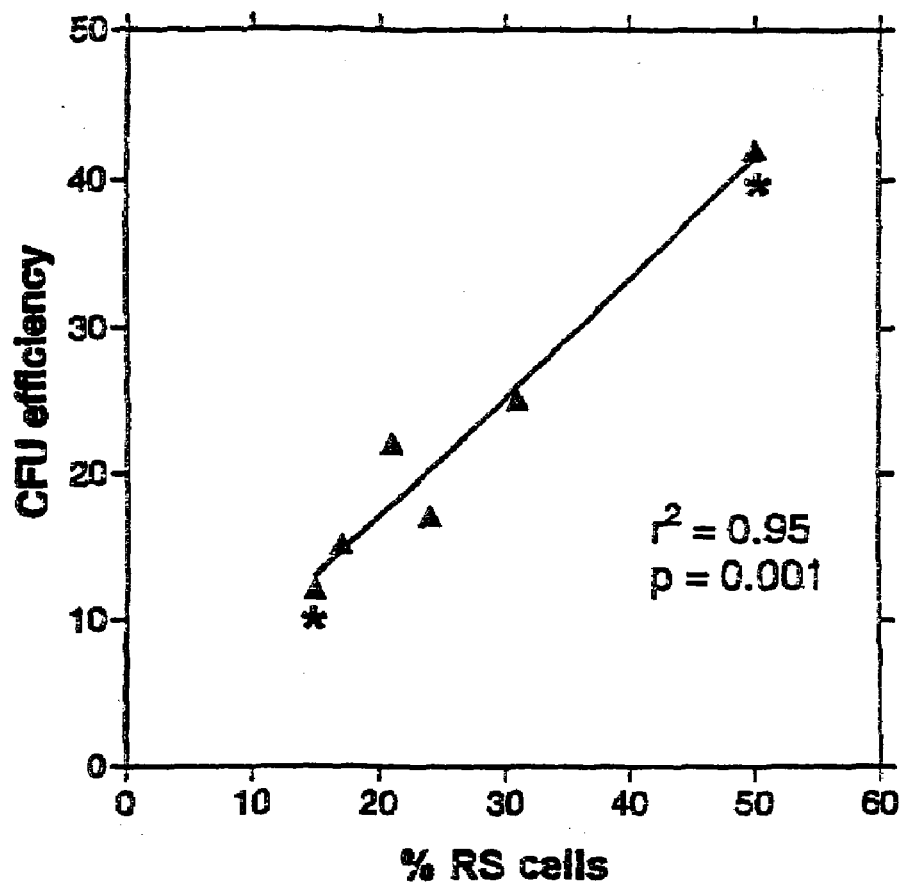
FIG. 21 is a graph which indicates proportionality between the percentage of RS cells and the percentage of CFUs in samples of MSCs. Filled triangles represent data obtained using samples taken from cultures that were plated at varying density and incubated for 14 days; asterisks represent data obtained using cultures from the same initial sample of MSCs incubated for 5 days (higher value) or for 14 days (lower value). "% RS" indicates the total percentage of RS-1 and RS-2 cells in the samples. "CFU efficiency" means the number of colonies observed per 100 cells plated.

The data in FIGS. 19 and 20 indicate that the earliest progenitors in the cultures are RS-1 and RS-2 cells. Therefore, the number of RS-1 and RS-2 cells in any sample of MSCs should reflect the number of cells that generate single-cell derived colonies in CFU assays. As indicated in FIG. 21, an approximately linear relationship was observed between the number of RS cells and CFU values obtained for a series of samples ($r^2$=0.95; p value=0.001). Moreover, the slope of the plot was 0.82±0.96 S.D. Therefore, the results indicated that each RS cell formed a colony with an average efficiency of about 82%. As also indicated in FIG. 21, the same relationship between CFUs and total RS cells (RS-1 plus RS-2) was observed using samples obtained from the same culture at different times after plating. For example, one culture was assayed on day 5 and day 12. On day 5, about 48 of every 100 cells was an RS cell and about 42 colonies were formed. On day 12, about 12 cells per 100 was an RS cell and about 12 colonies were formed. Since most of the RS cells on day 5 were RS-2 cells and most of the RS cells on day 12 were RS-1 cells, the results indicate that both populations generated single-cell derived colonies.

Epitope Profile of the Cell Cultures

All the cells in the cultures of MSCs were consistently negative for CD34, a marker for early hematopoietic stem cells, as indicated in Table 3. They were also negative for other markers for hematopoietic cells (CD11B, CD43, CD45). A small number (fewer than 10%) of all three cell types were dimly positive for the endothelial cell marker CD31. Also, a small number were also dimly positive for CD38, a marker for B lymphocytes, and some thymocytes, T lymphocytes, NK cells and macrophages. The mMSCs were dimly positive for the hematopoietic stem cell marker CD117 (c-Kit), but the RS-1 and RS-2 cells were negative. As reported previously (41), the mMSCs were moderately positive for Stro-1, an epitope for osteogenic MSCs (35). However, RS-1 and RS-2 cells were negative for Stro-1. One marked difference in the epitopes among the three subpopulations of cells was that the mMSCs were positive for CD90 (Thy-1), a marker for thymocytes and peripheral T lymphocytes. RS-1 cells were dimly positive but the RS-2 cells were negative.

TABLE 3

Epitope Profile of the Cells

| Epitope | RS-1 cells | RS-2 cells | mMSCs cells |
|---|---|---|---|
| CD34 | Negative | Negative | Negative |
| CD11B (Mac-I) | Negative | Negative | Negative |
| CD43 | Negative | Negative | Negative |
| CD45 | Negative | Negative | Negative |
| CD31 | Dim | Dim | Dim |
| CD38 | Dim | Dim | Dim |
| CD117 (c-Kit) | Negative | Negative | Dim |
| STRO-1 | Negative | Negative | Dim |
| CD90 (Thy-1) | Dim | Negative | Positive |

Extensive Expansion of the MSCs by Plating at Low Density

Figure 22:
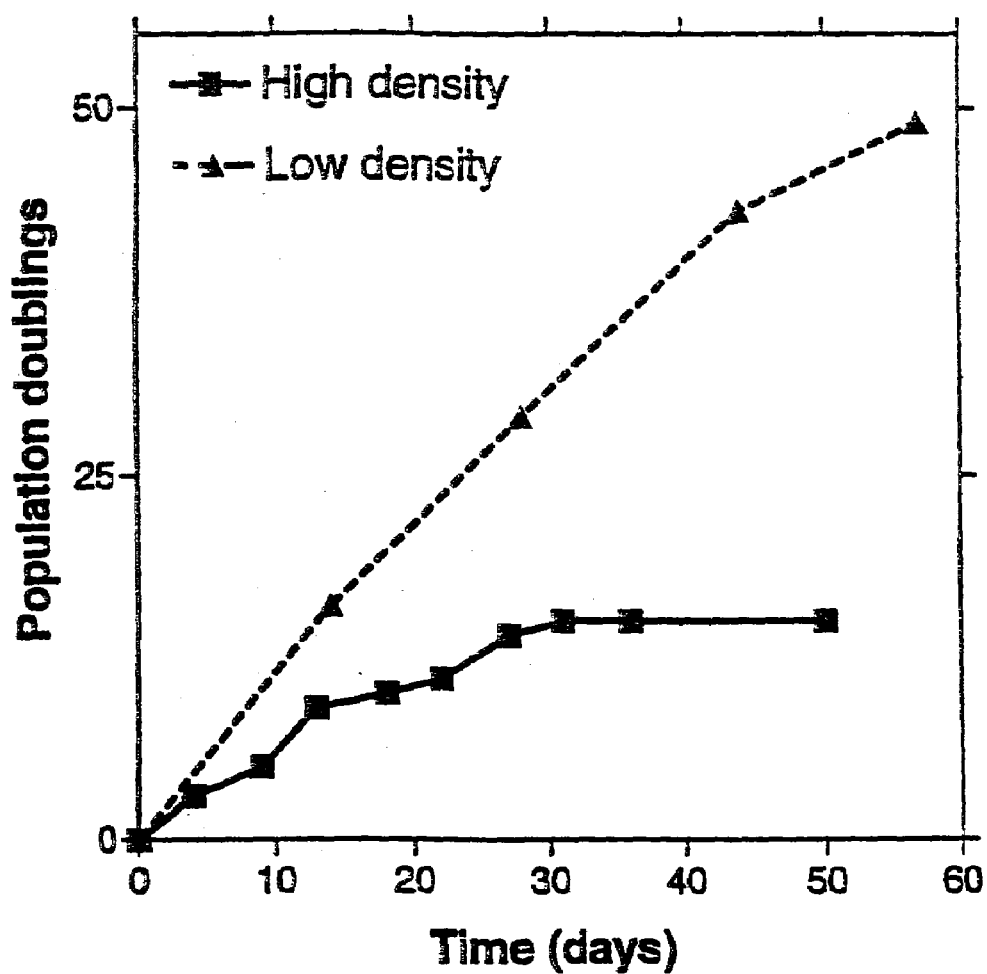
FIG. 22 is a graph which depicts the number of population doublings obtained when cells were plated at low density (broken line) and high density (solid line). Filled triangles represent data corresponding to cells that were plated at 1.5 cells per square centimeter, incubated for 10 to 14 days, and from which a large colony was then isolated by ring cloning for each subsequent passage under the same conditions; Filled squares represent data corresponding to MSCs from a sample with a comparable value for CFUs that was passed by plating at a high density of 5,000 cells per square centimeter, as described (41).

Because plating of MSCs at low density promoted rapid growth of the cultures, the extent to which the cells could be expanded in culture by repeated passage at low density was examined. In one experiment, the cells were plated at low density, a large colony was isolated from the plate with a cloning ring, and the cells in the colony were re-plated at low density. The procedure was repeated so that only the cells from the largest colonies were passed. The cells continued to grow through about 50 population doublings, as indicated in FIG. 22. In contrast, when a similar sample of MSCs was passed at high density, the cells stopped growing after about 15 doublings.

In a second series of experiments, several samples of MSCs were passed at low density with a more conventional protocol in which all the cells from a culture were harvested with EDTA/trypsin and an aliquot was re-plated at 3.0 cells per square centimeter for the next passage. The procedure was repeated for a total of three passages. The fold expansion of the cells varied from about 150-fold to over 2,000-fold during single passages of 14 days, as indicated in Table 4. With the four separate samples from two donors, the average fold expansion per passage was 600-fold, and therefore about $2 \times 10^9$-fold over three passages in six weeks. If all the cells from each passage had been plated, over $10^{13}$ MSCs would have been obtained from each 20 milliliter sample of aspirate. The average percent CFUs at the end of the third passage was about the same as the initial value for the samples (28% versus 33%). Therefore, calculated cumulated yield of CFU-cells was also about $10^{13}$.

TABLE 4

Expansion of Human MSCs in Culture

| Sample‡/ Passage^fi | Observed values for MSCs per 530 cells plated | Calculated cumulative totals‖ | |
|---|---|---|---|
| | | MSCs | CFUs |
| Donor 58R | | | |
| 1st | $8.0 \times 10^4$ | $7.0 \times 10^7$ | $2.2 \times 10^7$ |
| 2nd | $1.1 \times 10^6$ | $1.5 \times 10^{10}$ | $0.95 \times 10^{10}$ |
| 3rd | $2.3 \times 10^5$ | $6.5 \times 10^{13}$ | $1.40 \times 10^{13}$ |
| Donor 58L | | | |
| 1st | $8.6 \times 10^4$ | $1.1 \times 10^8$ | $0.25 \times 10^8$ |
| 2nd | $4.2 \times 10^5$ | $1.1 \times 10^{10}$ | $4.1 \times 10^{10}$ |
| 3rd | $3.1 \times 10^5$ | $5.0 \times 10^{13}$ | $1.5 \times 10^{13}$ |
| Donor 59R | | | |
| 1st | $1.9 \times 10^5$ | $2.8 \times 10^8$ | $1.1 \times 10^8$ |
| 2nd | $2.4 \times 10^5$ | $1.3 \times 10^{11}$ | $0.55 \times 10^{11}$ |
| 3rd | $7.5 \times 10^5$ | $1.8 \times 10^{14}$ | $0.52 \times 10^{14}$ |
| Donor 59L | | | |
| 1st | $1.4 \times 10^5$ | $2.4 \times 10^8$ | $0.91 \times 10^8$ |
| 2nd | $1.7 \times 10^5$ | $7.8 \times 10^{10}$ | $3.7 \times 10^{10}$ |
| 3rd | $5.0 \times 10^5$ | $7.4 \times 10^{13}$ | $2.2 \times 10^{13}$ |

Notes:
‡The samples were from bone marrow aspirates obtained at the same time from two normal volunteers (58 and 59), one from the right iliac crest (58R and 59R) and one from the left iliac crest (58L and 59L). Each of the aspirates was about 20 ml from which 1.2 to $2.7 \times 10^7$ nucleated cells were obtained. The nucleated cells were plated at high density to obtain frozen stocks of early passage MSCs (see text).
^fi For each passage, 530 MSCs were plated in 176-cm$^2$ plates for an average plating density of 3.0 cells per square centimeter. The cultures were incubated for 14 days, harvested with EDTA/trypsin, and then an aliquot of 530 cells re-plated at a density of 3.0 cells per square centimeter.
‖Calculated cumulative total of MSCs and CFUs if all the MSCs from the frozen stock and each passage had been re-plated at 3.0 cells per square centimeter.

Numerous previous reports demonstrated that MSCs are relatively easy to expand in culture by capitalizing on their tendency to adhere and proliferate on tissue culture surfaces (Friedenstein et al., 1976, Exper. Hematol. 4:267-274; Friedenstein et al., 1987, Cell & Tiss. Kinetics 20:263-272; Clark et al., 1995, Ann. N.Y. Acad. Sci. 770:70-78; Kuznetsov et al., 1997, Br. J. Haematol. 97:561-570; Kuznetsov et al., 1997, J. Bone Min. Res. 12:1335-1347; Bruder et al., 1997, J. Cell. Biochem. 64:278-294). Some species and strain-dependent variations are seen. In particular, murine MSCs from several strains can be difficult to propagate and are often contaminated by hematopoietic precursors (Clark et al., 1995, Ann. N.Y. Acad. Sci. 770:70-78; Phinney et al., 1999, J. Cell. Biochem. 72:570-585). In contrast, human MSCs are relatively easy to propagate and are largely free of hematopoietic precursors after two or three passages. In previous reports, however, human MSCs were passed by plating at relatively high densities of 5,000 cells per square centimeter and expanded three- to five-fold as the cells grew to confluence over about two weeks (Bruder et al., 1997, J. Cell. Biochem. 64:278-294). As demonstrated in this example, human MSCs propagate in a much more dramatic manner if they are plated at extremely low densities of 1.5 or 3.0 cells per square centimeter. At lower densities, the cultures expanded an average of 600-fold in two weeks. In some passages, up to 2,000-fold expansion in 12 days was observed.

Rapid expansion of the MSCs in culture was found to depend on the presence of a minor population of small cells. Previous reports made conflicting claims as to whether or not cultures of human MSCs are homogeneous. Some indicated that the cells are homogeneous by morphology and several other criteria such as surface epitopes (Pittenger et al., 1999, Science 284:143-147). Many, however, emphasized heterogeneity. In particular, Mets and Verdonk (Mets et al., 1981, Mech. Ageing. Dev. 16:81-89) emphasized the presence of large and flat cells that they referred to as type II cells and smaller spindle-shaped cells they referred to as type I cells. The type II cells propagated very slowly and the type I more rapidly. The FACS analyses here demonstrated that stationary cultures of MSCs contained a major population of large cells here referred to as mMSCs and a minor population of small and agranular cells (RS-1 cells). After re-plating the cultures at low density, a new population of small and granular RS-2 cells appeared. During the log phase growth, the population of mMSCs rapidly expanded, the RS-2 cells declined in number and the RS-1 cells increased. As noted by Mets and Verdonk (Mets et al., 1981, Mech. Ageing. Dev. 16:81-89) and other investigators (Prockop, 1997, Science 276:71-74), mMSCs are relatively mature cells that divide slowly and become the predominant cell as the cultures approach senescence (DiGirolamo et al., 1999, Br. J. Haematol. 107:275-281).

Figure 23:
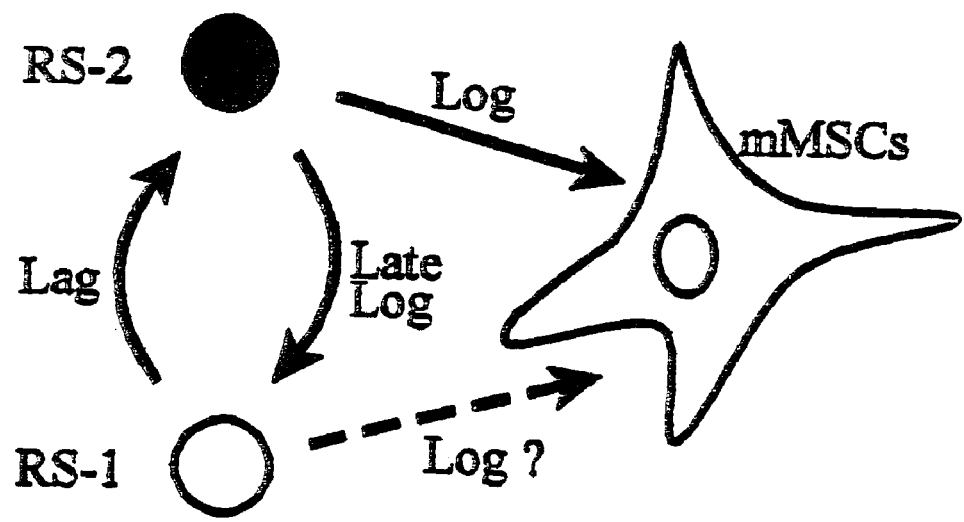
FIG. 23 is a diagram of a proposed scheme for the precursor-product relationships of cells in cultures of MSCs. Large mMSCs replicate poorly (2, 41). Therefore, RS-2 cells that appear during the lag phase must arise from RS-1 cells. During the early log phase of growth, RS-2 cells decline in number as mMSCs appear in large numbers. Therefore, RS-2 cells are probably precursors of mMSCs. However, the data do not exclude the possibility that RS-2 cells rapidly generate RS-1 cells, which give rise to mMSCs (dashed-arrow). Also, the earliest mMSCs can continue to replicate. During the late log phase, RS-2 cells decline in number and the RS-1 sub-population expands. Therefore, RS-2 cells can recycle into RS-1 cells.

The simplest explanation for the observations made herein is that cells referred to herein as RS-1 cells generate RS-2 cells during the lag phase, the RS-2 cells give rise to mMSCs during the log phase, and then the RS-2 cells regenerate RS-1 cells during the late log phase. This explanation is diagrammed in FIG. 23. While none of the observations or claims herein depend on the accuracy of this theory, this sequence of events is consistent with the time course in which the cells appear and disappear in the cultures, and the linear relationship between the number of RS cells and the number of cells in the same samples that can generate single-cell derived colonies.

The ease with which stem-like cells in cultures of human MSCs can be expanded presents a marked contrast to the difficulties that have been encountered in expanding hematopoietic stem cells (Glimm et al., 1999, Blood 97:2161-2168) and the relatively slow rate at which neural progenitor cells expand in culture (Carpenter et al., 1999, Exp. Neurol. 158:265-278). The ability to rapidly expand human MSCs in culture is important for using the cells for cell and gene therapy (Caplan, 1991, J. Orthoped. Res. 9:641-650; Prockop, 1997, Science 276:71-74). Under the conditions developed here, a single bone marrow aspirate obtained under local anesthesia can generate about $10^{13}$ cells, a number that approaches the total number of cells in the adult body. Of special importance was that after extensive expansion of the cells, the number of CFUs remained unchanged. The number of CFUs was previously shown to be closely correlated to the ability of the cells to differentiate into both osteoblasts or adipocytes (DiGirolamo et al., 1999, Br. J. Haematol. 107:275-281). Therefore, the results suggest that the expanded cells maintain their multipotentiality.

The following references are cited numerically in this example.

Example 5

Separation of RS Cells from Non-RS mMSCs

RS cells can be separated from non-RS mMSCs using at least two different methods. RS cells can be separated from non-RS mMSCs by elutriation using known methods. Alternatively, RS cells can be separated from other mMSCs by ultrafiltration. Because RS cells are smaller than non-RS mMSCs, they will pass through an ultrafiltration membrane having appropriately-sized pores. An example of such a membrane is a Millipore brand 10 micrometer isopore polycarbonate membrane. It is anticipated that substantially any other method of separating particles having a size not significantly greater than 10 micrometers from particles having a size significantly greater than 10 micrometers can be used to separate RS MSCs from non-RS MSCs. The results obtained by passing a preparation of MSCs through such an ultrafiltration membrane are shown in FIG. 24.

Figure 24:
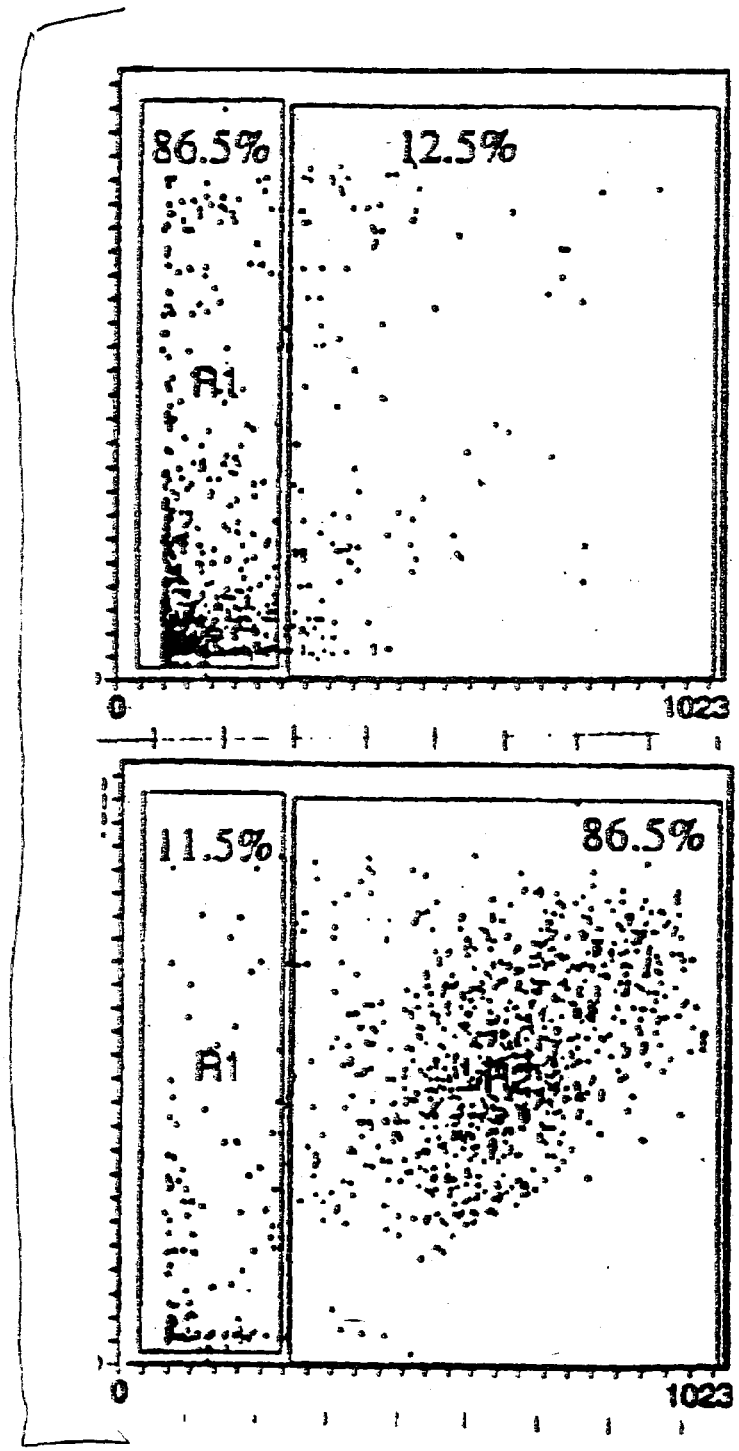
FIG. 24 is an pair of graphs which depict the cell content of MSC samples prepared by ultrafiltration. RS-1 cells are indicated in the boxes designated "R1"; all other MSCs were considered non-RSMSCs.

In the experiment for which the results are shown in FIG. 24, a frozen stock of MSCs was thawed at 37° C., diluted with complete medium, and recovered by centrifugation to remove DMSO. The cells were suspended in medium and plated at about 5,000 cells per square centimeter. After incubating the plated cells for about 1 day, non-adherent cells were removed, and the adherent cells were harvested using EDTA/trypsin. These cells were dissociated by passing them through a narrowed Pasteur pipette, and were then counted. The cells were plated in a cell factory apparatus at a density of about 3 cells per square centimeter, adjusted using values obtained from CFU assay to yield about 1 colony forming cell per square centimeter of cell factory surface. The cells were grown in 1 liter of complete medium, which was replaced every 3-4 days. The cells were harvested using 0.25% trypsin and 1 millimolar EDTA for 5 minutes at 37° C., and then washed by re-suspending them in 20% αMEM and centrifuging them. RS-1 and RS-2 cells were separated from other MSCs by re-suspending the cells in 20% αMEM at a concentration of about $10^6$ cells per milliliter. This cell suspension was ultrafiltered using a 10 micrometer isopore polycarbonate membrane filter (Millipore), and RS-1 and RS-2 cells were obtained in the filtrate. The filtrate was ultrafiltered a second time using the same type of membrane, and cells in the second filtrate were recovered by centrifugation. The homogeneity of the cells in the second filtrate and other samples was analyzed using FACS, and the results of this analysis are shown in FIG. 24. These results indicate that one sample (the upper panel of FIG. 24) consisted of about 86% RS-1 cells, and that another sample consisted of about 86% non-RS mMSCs. The overall recovery of cells was about 70%.

Example 6

Transfection of Human and Rat MSCs Using Exogenous Genes

Figure 25:
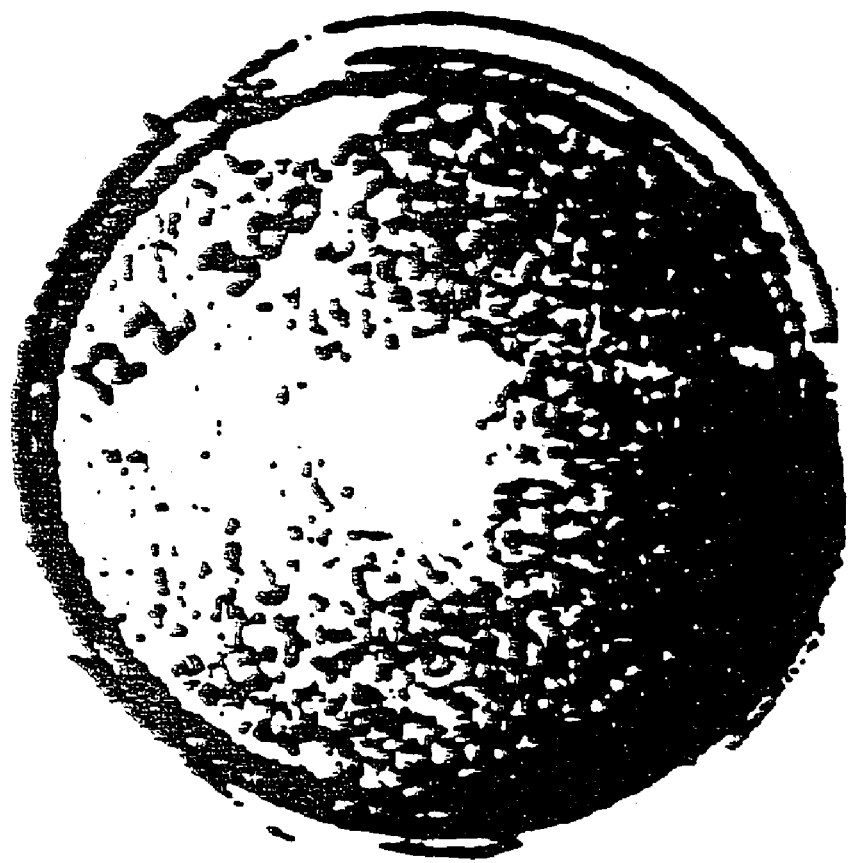
FIG. 25 is an image which depicts expression of lacZ in MSC cells which were electroporated in the presence of a vector comprising lacZ operably linked with the cytomegalovirus (CMV) promoter.
Figure 27A:
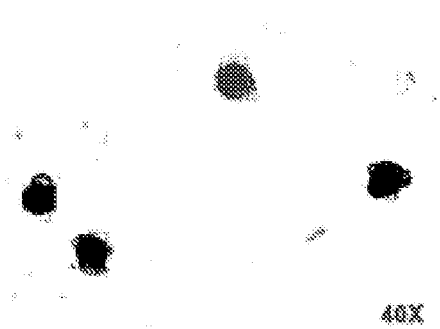
FIGS. 27A-F is a series of images of micrographs which define RS-1 cells and MSCs.
Figure 27B:
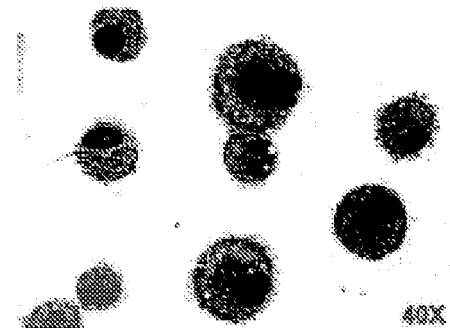
Figure 27C:
Figure 27D:
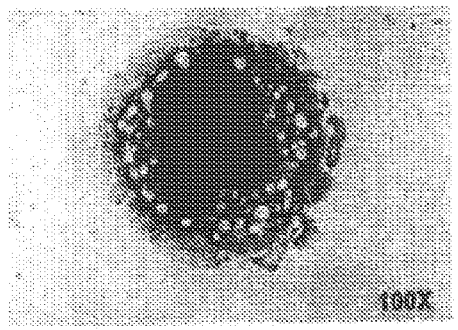
Figure 27E:
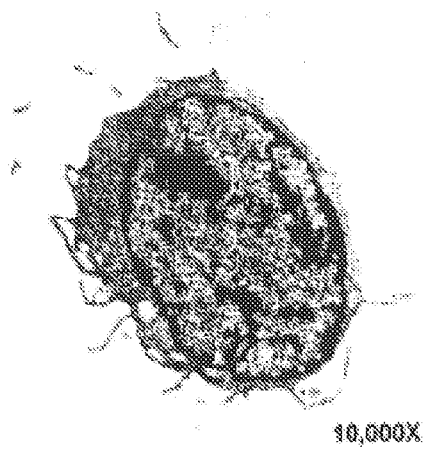
Figure 27F:
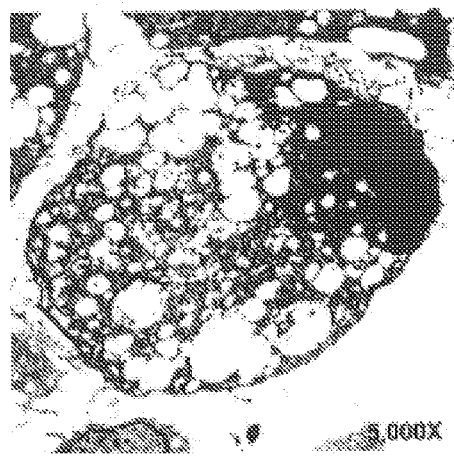

Using conditions slightly modified from those described (Matthews et al, 1995, Meth. Mol. Biol. 48:273-280), human MSCs were electroporated using a linearized DNA construct in which expression of the lacZ gene was driven by the CMV promoter (vector pCl-neo, obtained from Stratagene, into which the CMV-lacZ cassette of the ppGal-Control vector, obtained from Clontech, was cloned). About 10-20% of MSCs were transfected. More than 1 million stable G418-resistant cells which expressed lacZ were generated therefrom, as shown in FIG. 25.

These results demonstrate that electroporation can be used to introduce exogenous genes into MSCs. This procedure can thus be used as an alternative to transfection effected using virus vectors. Because MSCs can be so rapidly, readily, and extensively expanded, this result indicates that clones of MSCs electroporated with an exogenous gene (e.g. an exogenous normal gene to replace an aberrant copy of a gene which occurs in cells of a type which MSCs can become) can be used to generate cells in which a normal copy of a gene is inserted (i.e. by homologous recombination) in place of an aberrant copy of the same gene in cells of a patient. In essence, double selection can be used to isolate one or more MSCs that have undergone homologous recombination prior to providing those cells to a patient. Thus, use of viruses or virus vectors which integrate randomly into the genome (or do not insert into the genome at all) can be avoided. This represents a major advance in gene therapy methods. Vectors which do not integrate into the genome are generally lost over time. Random integration of a vector into the genome has the risk that normal genes or control mechanisms will be disrupted, leading to complications. Use of electroporated MSCs in which homologous recombination is detected avoids these drawbacks.

Example 7

Examples of Bioengineering Using MSCs

Because the methods described in this application can be used to produce so many MSCs rapidly and reliably, previously impractical or even impossible feats of bioengineering are now enabled. For example, large numbers of MSCs can be generated as described herein and differentiated (i.e. using any of a variety of known methods) to form cells which can replace microscopic or macroscopic tissue portions. By way of example, MSCs can be induced, using known methods, to become cartilage cells. Such cells, used alone or incorporated into any of a variety of known natural or artificial tissue scaffolding materials (e.g. collagen-based matrices), can be used to replace or repair cartilage tissue, in surgical procedures such as reconstructive surgery of the face (or other organs, using appropriately differentiated cells) or reconstruction or resurfacing of joints. Further by way of example, MSCs can be expanded in vitro, induced to become one or more types of bone cells (e.g. osteoblasts). The bone cells (optionally remaining mixed with a small or large fraction of MSCs, and also optionally mixed with a scaffolding material) can be provided to the site of a bone injury (e.g. a fracture site or a site from which bone has been surgically removed), in order to induce formation of new bone, thereby alleviating the bone injury. Such cells could also be implanted within a coating or within bores (or other cavities) within a bone-contacting prosthesis (e.g. a hip prosthesis). The presence of such cells within or connected to the prosthesis induces stronger bonding of patient bone to the prosthesis, improving the durability and acceptance of the device. By way of example, such cells can be incorporated onto or within cavities in the shaft of a hip prosthesis. Insertion of the shaft within the femur of a patient brings the cells into contact with the patient's femur. The presence of bone cells (and optionally MSCs induced to become bone cells) in the space bridging the patient's femur and the shaft of the prosthesis induces formation of bone that can bind with the shaft (i.e. by binding with an MSC-containing coating of the shaft) or formation of continuous bone that extends from the patient's femur to the interior of a cavity within the shaft. Such bone formation more securely and irreversibly binds the shaft to the femur, reducing the incidence of femur-prosthesis disattachment.

Example 8

Additional Methods for the Isolation and Characterization of RS Cells

RS cells isolated as described elsewhere herein were further characterized as follows.

Populations of RS cells and mature MSCs were assessed for their ability to react with a variety of antibodies as shown in FIG. 26. The data presented in FIG. 26 provides additional criteria for the characterization of RS cells. RS-1 cells and mature MSCs were also characterized microscopically, and the results are presented in FIGS. 27A-D, wherein the morphological identity of these cells is evident.

Further, proteins were extracted from cultures enriched for MSCs and were assessed in two dimensional gels. The results of this experiment are shown in FIGS. 28A and 28B wherein there is shown images of two dimensional gels of proteins obtained from cultures that are enriched for RS cells and cultures that have considerably fewer of the RS cells and more of the mature MSCs. In FIG. 28A there are shown proteins obtained from early lag phase cultures (5 days of incubation; 60% RS-1 and RS-2 cells) and in FIG. 28B there is shown proteins obtained from late lag phase cultures (12 days of incubation; 15% RS-1 cells). These data were further analyzed and in FIG. 29 there is shown a table depicting a protein analysis of the gels shown in FIG. 28A (early lag phase culture, identification number LB2D6-80-1), and FIG. 28B (late lag phase culture, identification number LB2D6-80-7) in which proteins unique to either culture were analyzed. A protein known as Lipocortin II (also known as Annexin II) has been found only in cultures expanded according to the methods of the invention described herein. Thus, the invention includes a method of using this protein to isolated and purify MSCs expanded in culture for use in therapy.

The disclosures of every patent, patent application, and publication cited herein are incorporated herein by reference.

While the invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of inducing proliferation of isolated human marrow stromal cells in vitro by plating and replating said cells at an initial density of 50 cells or less per square centimeter of growth surface wherein the method generates enhanced expandability of marrow stromal cells relative to results in a greater total number of cells to be obtained compared to the total number of cells obtained from plating and replating at an initial density of more than 50 cells or less per square centimeter of growth surface, the method comprising:

(1) providing the isolated human marrow stromal cells and a growth medium comprising a mammalian serum to a growth surface such that the initial density of the isolated human marrow stromal cells is 50 cells or less per square centimeter of growth surface, (2) incubating the growth surface of step (1) under growth-promoting conditions, whereby the human marrow stromal cells proliferate, and (3) replating the proliferated marrow stromal cells and a growth medium comprising a mammalian serum to a second growth surface at least one time such that the initial density of the replated isolated human marrow stromal cells is 50 cells or less per square centimeter of growth surface, wherein the replating allows the cells to expand by a factor of at least 10-fold.

2. The method of claim 1, wherein in step (1) the initial density of the isolated human marrow stromal cells is 25 or less cells per square centimeter of growth surface.

3. The method of claim 1, wherein in step (1) the initial density of the isolated human marrow stromal cells is 12 cells or less per square centimeter of growth surface.

4. The method of claim 1, wherein in step (1) the initial density of the isolated human marrow stromal cells is 10 cells or less per square centimeter of growth surface.

5. The method of claim 1, wherein in step (1) the initial density of the isolated human marrow stromal cells is 6 cells or less per square centimeter of growth surface.

6. The method of claim 1, wherein in step (1) the initial density of the isolated human marrow stromal cells is 3 cells or less per square centimeter of growth surface.

7. The method of claim 1, wherein in step (1) the initial density of the isolated human marrow stromal cells if 1.5 cells or less per square centimeter of growth surface.

8. The method of claim 1, wherein in step (1) the initial density of the isolated human marrow stromal cells is 1.0 cells or less per square of growth surface.

9. The method of claim 1, wherein in step (1) the initial density of the isolated human marrow stromal cells is about 0.5 cells or less per square centimeter of growth surface.

10. The method of claim 1, wherein after step (2) the human marrow stromal cells are harvested from the growth surface following not more than 14 days of incubation.

11. The method of claim 1, wherein after step (2) the human marrow stromal cells are harvested from the growth surface following not more than 10 days of incubation.

12. The method of claim 1, further wherein
  (4) the second growth surface is incubated under growth-promoting conditions, whereby the human marrow stromal cells on the second growth surface proliferate; and
  (5) the human marrow stromal cells on the second growth surface are harvested.

13. The method of claim 12, wherein in step (5) the human marrow stromal cells are harvested from the second growth surface following not more than 14 days of incubation.

14. The method of claim 12, wherein in step (5) the human marrow stromal cells are harvested from the second growth surface following not more than 10 days incubation.

15. The method of claim 12, further wherein
  (6) cells harvested from the second growth surface in step (5) and a growth medium are provided to a third growth surface such that the initial density of the human marrow stromal cells harvested from the second growth surface is 50 cells or less per square centimeter of the third growth surface and
  (7) the third growth surface is incubated under growth-promoting conditions, whereby the human marrow stromal cells on the third growth surface proliferate; and
  (8) the human marrow stromal cells on the third growth surface are harvested.

16. The method of claim 15, wherein in step (8) the human marrow stromal cells are harvested from the third growth surface following not more than 14 days of incubation.

17. The method of claim 15, wherein in step (8) the human marrow stromal cells are harvested following not more than 10 days of incubation.

18. The method of claim 15, wherein in step (6) the human marrow stromal cells are seeded on the third growth surface at an initial density of about 3 cells or less per square centimeter.

19. The method of claim 1, wherein the mammalian serum is fetal bovine serum.

20. The method of claim 1, further wherein in step (1) a growth factor is added to the growth medium.

21. The method of claim 20, wherein the growth factor is selected from the group consisting of fibroblast growth factor, platelet derived growth factor, insulin growth factor, and endothelial growth factor.

22. A method of enhancing in vitro proliferation of isolated human marrow stromal cells growing on a surface in the presence of a growth medium comprising a mammalian serum by plating said cells at an initial density of 50 cells or less per square centimeter of growth surface, the method comprising supplementing the growth medium with a conditioned medium, wherein the conditioned medium is obtained from a culture of producer human marrow stromal cells which are grown on a second surface at an initial density of at least 0.5 cells or less per square centimeter and which are incubated for at least 3 days, whereby the isolated human marrow stromal cells proliferate, and further wherein the proliferated isolated marrow stromal cells and a growth medium comprising a mammalian serum are replated at least one time to a third growth surface such that the initial density of the replated isolated human marrow stromal cells is 50 cells or less per square centimeter of growth surface, wherein the replating allows the cells to expand by a factor of at least 10-fold, wherein the method generates enhanced expandability of marrow stromal cells relative to plating and replating at an initial density of more than 50 cells per square centimeter of growth surface.

23. The method of claim 22, wherein the producer human marrow stromal cells are grown on the second surface at an initial density of at least 12 cells per square centimeter.

24. The method of claim 22, wherein the producer human marrow stromal cells are incubated for at least 6 days.

25. A method of inducing proliferation of human marrow stromal cells in vitro by plating said cells at an initial density of 50 cells or less per square centimeter of growth surface, the method comprising isolating mononuclear cells from a bone marrow sample, incubating the mononuclear cells to yield colonies, isolating an individual colony, and incubating human marrow stromal cells obtained from the isolated colony in a container having a growth surface, the container containing a growth medium comprising a mammalian serum and the cells at a density of 50 cells or less per square centimeter of growth surface, whereby the cells proliferate, and further wherein the proliferated isolated marrow stromal cells and a growth medium comprising a mammalian serum are replated at least one time to a second growth surface such that the initial density of the replated isolated human marrow stromal cells is 50 cells or less per square centimeter of growth surface, wherein the replating allows the cells to expand by a factor of at least 10-fold, wherein the method generates enhanced expandability of marrow stromal cells relative to plating and replating at an initial density of more than 50 cells or less per square centimeter of growth surface.

26. A method of assessing the expandability of isolated human marrow stromal cells in vitro by plating said cells at an initial density of 50 cells or less per square centimeter of growth surface, the method comprising incubating isolated human marrow stromal cells on a surface in the presence of a growth medium comprising a mammalian serum at an initial density of 50 cells or less per square centimeter of surface and assessing the colony forming efficiency of the human marrow stromal cells, whereby the expandability of the human marrow stromal cells is approximately proportional to the colony-forming efficiency of the human marrow stromal cells, and further wherein the expanded isolated marrow stromal cells and a growth medium comprising a mammalian serum are replated at least one time to a second growth surface such that the initial density of the replated isolated human marrow stromal cells is 50 cells or less per square centimeter of growth surface, wherein replating allows the cells to expand by a factor of at least 10-fold, wherein the method generates enhanced expandability of marrow stromal cells relative to plating and replating at an initial density of more than 50 cells or less per square centimeter of growth surface.

27. The method of claim 26, wherein the human marrow stromal cells are incubated for at least about 10 days.

28. The method of claim 26, wherein the colony-forming efficiency is compared with the colony-forming efficiency of another sample of human marrow stromal cells incubated in the same manner, wherein the expandability of the human marrow stromal cells of the other sample is known.

29. The method of claim 26, wherein the colony-forming efficiency is compared with a reference plot of colony-forming efficiency versus expandability.

* * * * *